United States Patent
Ji et al.

(10) Patent No.: US 7,309,699 B2
(45) Date of Patent: Dec. 18, 2007

(54) 3-QUINUCLIDINYL AMINO-SUBSTITUTED BIARYL DERIVATIVES

(75) Inventors: Jianguo Ji, Libertyville, IL (US); Tao Li, Grayslake, IL (US); Ying Wang, Lake Villa, IL (US)

(73) Assignee: Abbott Laboratories, Abbott Park, IL (US)

( * ) Notice: Subject to any disclaimer, the term of this patent is extended or adjusted under 35 U.S.C. 154(b) by 55 days.

(21) Appl. No.: 11/015,158

(22) Filed: Dec. 17, 2004

(65) Prior Publication Data

US 2005/0159597 A1 Jul. 21, 2005

Related U.S. Application Data

(60) Provisional application No. 60/531,877, filed on Dec. 22, 2003.

(51) Int. Cl.
C07D 453/02 (2006.01)
C07D 487/04 (2006.01)
(52) U.S. Cl. ............ 514/183; 514/252.04; 514/255.05; 514/256; 514/305; 540/557; 544/238; 544/333; 544/405; 546/133
(58) Field of Classification Search ................ 546/133; 544/239, 298, 336, 238, 333, 405; 540/557; 514/183, 252.04, 255.05, 256, 305
See application file for complete search history.

(56) References Cited

U.S. PATENT DOCUMENTS 4,447,607 A * 5/1984 Johnson ....................... 540/471
5,589,477 A * 12/1996 Chokai et al. ............... 514/256

FOREIGN PATENT DOCUMENTS

| EP | 0 709 381 | 5/1996 |
|----|-----------|--------|
| EP | 0 774 256 | 5/1997 |
| EP | 0773027 | 5/1997 |
| WO | 92/04333 | 3/1992 |
| WO | 94/18201 | 8/1994 |
| WO | 95/03302 | 2/1995 |
| WO | 96/12711 | 5/1996 |
| WO | 98/27983 | 7/1998 |
| WO | 2004/016608 | 2/2004 |
| WO | 2004/022556 | 3/2004 |
| WO | WO 2004022556 A1 * | 3/2004 |

OTHER PUBLICATIONS

Tsuneki et al, Alkaloids Indolizidine 235B', Quinolizidine 1-epi-207L, and the Tricyclic 205B are Potent and Selective Noncompetitive Inhibitors of Nicotinic Acetylcholine Receptors, MOL. PHARM., 66(4):1061-1069 (2004).*
Bundgaard, Design of Prodrugs (Elsevier Science Publishers 1985).*
Wermuth, The Practice of Medicinal Chemistry (Academic Press 1996).*
CAS Document Nos. 140:253750.*
CAS Document Nos. 143:78201.*
Adler et al, "Schizophrenia, sensory gating, and nicotinic receptors," Schizophrenia Bulletin 24(2): 189-202 (1998).
Cordero-Erausquin et al., "Tonic nicotinic modulation of serotoninergic transmission in the spinal cord," PNAS 98(5):2803-2807 (2001).
Friedman et al., "A double blind placebo controlled trial of donepezil adjunctive treatment to risperidone for the cognitive impairment of schizophrenia," Biol. Psychiatry 51:349-357 (2002).
Heeschen et al., "Nicotine stimulates angiogenesis and promotes tumor growth and athersclerosis," Nature Medicine 7(7):833-839 (2001).
Heeschen et al., "A novel angiogenic pathway mediated by non-neuronal nicotinic acetycholine receptors," Journal of Clinical Investigation 110(4):527-536 (2002).
Jonnala et al., "Relationship between the increased cell surface α7 nicotinic receptor expression and neuroprotection induced by several nicotinic receptor agonists," Journal of Neuroscience Research 66:565-572 (2001).
Kihara et al., "α7 Nicotinic receptor transduces signals to phosphatidylinositol 3-kinase to block A β-amyloid-induced neurotoxicity," Journal of Biological Chemistry 276(17):13541-13546 (2001).
Leonard et al., "Smoking and schizophrenia: abnormal nicotinic receptor expression," European Journal of Pharmacology 393:237-242 (2000).
Levin, "Nicotinic receptor subtypes and cognitive function," J. Neurobiol. 53:633-640 (2002).
Liu et al., "β-Amyloid peptide blocks the response of α7-containing nicotinic receptors on hippocampal neurons," PNAS 98(8):4734-4739 (2001).
Rowley et al., "Current and novel approaches to the drug treatment of schizophrenia," Journal of Medicinal Chemistry 44(4):477-501 (2001).
Shimoharna et al., "Nicotinic α7 receptors protect against glutamate neurotoxicity and neuronal ischemic damage," Brain Research 779:359-363 (1998).

(Continued)

Primary Examiner—Zinna N. Davis
(74) Attorney, Agent, or Firm—Portia Chen; Sreenivasarao Vepachedu

(57) ABSTRACT

Compounds of formula (I)

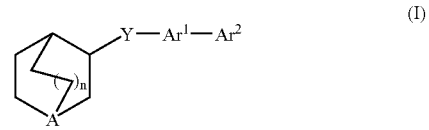

(I)

wherein A is N or N$^+$—O$^-$; n is 0, 1, or 2; Y is O, S, —NH—, and —N-alkyl-; Ar$^1$ is both 6-membered aromatic rings; Ar$^2$ is 5- or 6-membered aromatic rings with a —NR$^8$R$^9$ group, as defined herein. The compounds are useful in treating conditions or disorders prevented by or ameliorated by α7 nAChR ligands. Also disclosed are pharmaceutical compositions having compounds of formula (I) and methods for using such compounds and compositions.

6 Claims, No Drawings

OTHER PUBLICATIONS

Son et al., "Evidence suggesting that the mouse sperm acrosome reaction initiated by the zona pellucida involves an α7 nicotinic acetylcholine receptor," Biology of Reproduction 68:1348-1353 (2003).

Stevens et al., "Selective $\alpha_7$-nicotinic agonists normalized inhibition of auditory response in DBA mice," Psychopharmacology 136:320-327 (1998).

Torii et al., "A versatile cycloaddition for the generation of pyrrolidine derivatives *via* C-N-C 1,3-dipoles," Chemistry Letters 747:748 (1996).

Wang et al., "Nicotinic acetylcholine receptor α7 subunit is an essential regulator of inflammation," Nature 421:384-388 (2003).

* cited by examiner

3-QUINUCLIDINYL AMINO-SUBSTITUTED BIARYL DERIVATIVES

This application claims priority to U.S. Provisional Patent Application Ser. No. 60/531,877, filed Dec. 22, 2003, which is incorporated herein by reference.

TECHNICAL FIELD

The invention relates to 3-quinuclidinyl amino-substituted biaryl derivatives, compositions comprising such compounds, and methods of treating conditions and disorders using such compounds and compositions.

DESCRIPTION OF RELATED TECHNOLOGY

Nicotinic acetylcholine receptors (nAChRs) are widely distributed throughout the central (CNS) and peripheral (PNS) nervous systems. Such receptors play an important role in regulating CNS function, particularly by modulating release of a wide range of neurotransmitters, including, but not necessarily limited to acetylcholine, norepinephrine, dopamine, serotonin and GABA. Consequently, nicotinic receptors mediate a very wide range of physiological effects, and have been targeted for therapeutic treatment of disorders relating to cognitive function, learning and memory, neurodegeneration, pain and inflammation, psychosis and sensory gating, mood and emotion, among others.

Many subtypes of the nAChR exist in the CNS and periphery. Each subtype has a different effect on regulating the overall physiological function. Typically, nAChRs are ion channels that are constructed from a pentameric assembly of subunit proteins. At least 12 subunit proteins, $\alpha 2$-$\alpha 10$ and $\beta 2$-$\beta 4$, have been identified in neuronal tissue. These subunits provide for a great variety of homomeric and heteromeric combinations that account for the diverse receptor subtypes. For example, the predominant receptor that is responsible for high affinity binding of nicotine in brain tissue has composition $(\alpha 4)_2(\beta 2)_3$ (the $\alpha 4\beta 2$ subtype), while another major population of receptors is comprised of the homomeric $(\alpha 7)_5$ (the $\alpha 7$ subtype).

Certain compounds, like the plant alkaloid nicotine, interact with all subtypes of the nAChRs, accounting for the profound physiological effects of this compound. While nicotine has been demonstrated to have many beneficial properties, not all of the effects mediated by nicotine are desirable. For example, nicotine exerts gastrointestinal and cardiovascular side effects that interfere at therapeutic doses, and its addictive nature and acute toxicity are well-known. Ligands that are selective for interaction with only certain subtypes of the nAChR offer potential for achieving beneficial therapeutic effects with an improved margin for safety.

The $\alpha 7$ nAChRs have been shown to play a significant role in enhancing cognitive function, including aspects of learning, memory and attention (Levin, E. D., J. Neurobiol. 53: 633-640, 2002). For example, $\alpha 7$ nAChRs have been linked to conditions and disorders related to attention deficit disorder, attention deficit hyperactivity disorder (ADHD), Alzheimer's disease (AD), mild cognitive impairment, senile dementia, dementia associated with Lewy bodies, dementia associated with Down's syndrome, AIDS dementia, Pick's Disease, as well as cognitive deficits associated with schizophrenia, among other systemic activities. The activity at the $\alpha 7$ nAChRs can be modified or regulated by the administration of $\alpha 7$ nAChR ligands. The ligands can exhibit antagonist, agonist, partial agonist, or inverse agonist properties. Thus, $\alpha 7$ ligands have potential in treatment of various cognitive disorders.

Although various classes of compounds demonstrating $\alpha 7$ nAChR-modulating activity exist, it would be beneficial to provide additional compounds demonstrating activity at the $\alpha 7$ nAChRs that can be incorporated into pharmaceutical compositions useful for therapeutic methods. Specifically, it would be beneficial to provide compounds that interact selectively with $\alpha 7$-containing neuronal nAChRs compared to other subtypes.

SUMMARY OF THE INVENTION

The invention is directed to 3-quinuclidinyl amino-substituted biaryl derivative compounds as well as compositions comprising such compounds, and method of using the same. Compounds of the invention have the formula:

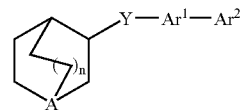

(I)

or a pharmaceutically acceptable salt, ester, amide, or prodrug thereof, wherein:

A is N or $N^+$—$O^-$;

n is 0, 1, or 2;

Y is selected from the group consisting of O, S, and —N($R^1$)—;

$Ar^1$ is a group of the formula:

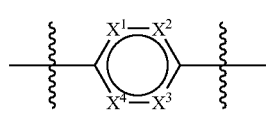

(a)

$Ar^2$ is a group of the formula:

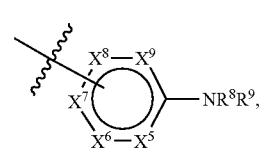

(b)

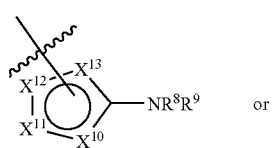

(c)

or

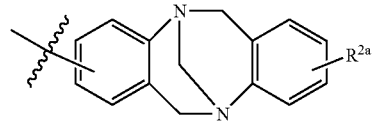

(d)

$X^1$, $X^2$, $X^3$, and $X^4$ are each independently selected from the group consisting of N and —C($R^2$);

one of $X^5$, $X^6$, $X^7$, $X^8$ and $X^9$ is —C and the others are each independently selected from the group consisting of N and —C($R^5$), and group (b) is attached to $Ar^1$ through one of $X^5$, $X^6$, $X^7$, $X^8$ and $X^9$ that is represented by C;

one of $X^{10}$, $X^{11}$, $X^{12}$, and $X^{13}$ is C and the others are each independently selected from the group consisting of N, —N($R^1$), O, S and —C($R^5$) and group (c) is attached to $Ar^1$ through one of $X^{10}$, $X^{11}$, $X^{12}$, and $X^{13}$ that is represented by C;

$R^1$ is hydrogen or alkyl;

$R^2$ at each occurrence is independently selected from the group consisting of hydrogen, halogen, alkyl, —$OR^3$, and —$NHR^4$;

$R^{2a}$ is halogen or alkyl;

$R^3$ and $R^4$ are each independently selected from the group consisting of hydrogen, alkyl, alkylcarbonyl, and arylcarbonyl;

$R^5$ is selected from the group consisting of hydrogen, halogen, nitro, alkyl, aryl, alkylcarbonyl, arylcarbonyl, —$OR^6$ and —$NR^8R^9$;

$R^6$ is independently selected from the group consisting of hydrogen, alkyl, alkylcarbonyl, and arylcarbonyl; and $R^8$ and $R^9$ are each independently selected from the group consisting of hydrogen, alkyl, aryl, arylalkyl, cycloalkylalkyl, alkylcarbonyl, —N=C(alkyl)(alkoxycarbonyl), alkoxycarbonyl, arylcarbonyl, aryloxycarbonyl, and alkylsulfonyl.

Another aspect of the invention relates to pharmaceutical compositions comprising compounds of the invention. Such compositions can be administered in accordance with a method of the invention, typically as part of a therapeutic regimen for treatment or prevention of conditions and disorders related to nAChR activity, and more particularly α7 nAChR activity.

Yet another aspect of the invention relates to a method of selectively modulating to nAChR activity, for example α7 nAChR activity. The method is useful for treating and/or preventing conditions and disorders related to α7 nAChR activity modulation in mammals. More particularly, the method is useful for conditions and disorders related to attention deficit disorder, attention deficit hyperactivity disorder (ADHD), Alzheimer's disease (AD), mild cognitive impairment, senile dementia, AIDS dementia, Pick's Disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammatory pain, neuropathic pain, infertility, need for new blood vessel growth associated with wound healing, need for new blood vessel growth associated with vascularization of skin grafts, and lack of circulation, more particularly circulation around a vascular occlusion, among other systemic activities.

The compounds, compositions comprising the compounds, and methods for treating or preventing conditions and disorders by administering the compounds are further described herein.

DETAILED DESCRIPTION OF THE INVENTION

Definition of Terms

Certain terms as used in the specification are intended to refer to the following definitions, as detailed below.

The term "acyl" as used herein, means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein, means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" means an alkoxy group, as defined herein, appended to the parent molecular moiety through a carbonyl group, represented by —C(O)—, as defined herein. Representative examples of alkoxycarbonyl include, but are not limited to, methoxycarbonyl, ethoxycarbonyl, and tert-butoxycarbonyl.

The term "alkoxyimino" as used herein, means an alkoxy group, as defined herein, appended to the parent molecular moiety through an imino group, as defined herein. Representative examples of alkoxyimino include, but are not limited to, ethoxy(imino)methyl and methoxy(imino)methyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl" means a straight or branched chain hydrocarbon containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amido" as used herein, means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "aryl" as used herein, means a monocyclic or bicyclic aromatic ring system. Representative examples of aryl include, but are not limited to, phenyl and naphthyl.

The aryl groups of this invention are substituted with 0, 1, 2, 3, 4, or 5 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, carboxy, cyano, formyl, haloalkoxy, haloalkyl, halo, hydroxy, hydroxyalkyl, mercapto, nitro, thioalkoxy, —NR$^A$R$^B$, (NR$^A$R$^B$)alkyl, (NR$^A$R$^B$)alkoxy, (NR$^A$R$^B$)carbonyl, and (NR$^A$R$^B$)sulfonyl. For example, substituted aryl groups can include, but are not limited to, tolyl.

The term "arylcarbonyl" as used herein, means an aryl group, as defined herein, appended to the parent molecular moiety through a carbonyl group, as defined herein. Representative examples of arylcarbonyl include, but are not limited to, phenylcarbonyl, (methylaminophenyl)carbonyl, (dimethylaminophenyl)carbonyl, and (naphthyl)carbonyl.

The term "aryloxycarbonyl", as used herein, means an aryl-O— group, wherein the aryl group of aryl-O— is as defined herein, or a benzyl-O— group appended to the parent molecular moiety through a carbonyl group, represented by —C(O)—, as defined herein. Representative examples of alkoxycarbonyl include, but are not limited to, phenoxycarbonyl and benzyloxycarbonyl.

The term "carbonyl" as used herein, means a —C(O)— group.

The term "carboxy" as used herein, means a —CO$_2$H group.

The term "cyano" as used herein, means a —CN group.

The term "cycloalkyl" as used herein, means a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

The cycloalkyl groups of the invention are substituted with 0, 1, 2, 3, or 4 substituents selected from acyl, acyloxy, alkenyl, alkoxy, alkoxyalkoxy, alkoxyalkyl, alkoxycarbonyl, alkoxyimino, alkyl, alkynyl, amido, carboxy, cyano, ethylenedioxy, formyl, haloalkoxy, haloalkyl, halogen, hydroxy, hydroxyalkyl, methylenedioxy, thioalkoxy, and —NR$_A$R$_B$.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "formyl" as used herein, means a —C(O)H group.

The term "halo" or "halogen" means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl" means an aromatic five- or six-membered ring containing 1, 2, 3, or 4 heteroatoms independently selected from nitrogen, oxygen, or sulfur. The heteroaryl groups are connected to the parent molecular moiety through a carbon or nitrogen atom. Representative examples of heteroaryl include, but are not limited to, furyl, imidazolyl, isoxazolyl, isothiazolyl, oxadiazolyl, oxazolyl, pyrazinyl, pyrazolyl, pyridazinyl, pyridinyl, pyrimidinyl, pyrrolyl, tetrazolyl, thiadiazolyl, thiazolyl, thienyl, triazinyl, and triazolyl.

The heteroaryl groups of the invention are substituted with 0, 1, 2, or 3 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halo, hydroxy, hydroxyalkyl, mercapto, nitro, —NR$_A$R$_B$, (NR$_A$R$_B$)alkyl, (NR$_A$R$_B$)alkoxy, (NR$_A$R$_B$)carbonyl, and (NR$_A$R$_B$)sulfonyl.

The term "bicyclic heteroaryl" refers to fused aromatic nine- and ten-membered bicyclic rings containing 1, 2, 3, or 4 heteroatoms independently selected from nitrogen, oxygen, or sulfur, or a tautomer thereof. The bicyclic heteroaryl groups are connected to the parent molecular moiety through a carbon or nitrogen atom. Representative examples of bicyclic heteroaryl rings include, but are not limited to, indolyl, benzothiazolyl, benzofuranyl, isoquinolinyl, and quinolinyl. Bicyclic heteroaryl groups of the invention are substituted with 0, 1, 2, or 3 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halo, hydroxy, hydroxyalkyl, mercapto, nitro, —NR$_A$R$_B$, (NR$_A$R$_B$)alkyl, (NR$_A$R$_B$)alkoxy, (NR$_A$R$_B$)carbonyl, and (NR$_A$R$_B$)sulfonyl.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —NO$_2$ group.

The term "—NR$^A$R$^B$" as used herein, means two groups, R$^A$ and R$^B$, which are appended to the parent molecular moiety through a nitrogen atom. R$^A$ and R$^B$ are each independently hydrogen, alkyl, alkylcarbonyl, or formyl. Representative examples of —NR$^A$R$^B$ include, but are not limited to, amino, methylamino, acetylamino, and acetylmethylamino.

The term "(NR$^A$R$^B$)alkyl" as used herein, means a —NR$^A$R$^B$ group, as defined herein, appended to the parent molecular moiety through an alkyl group, as defined herein. Representative examples of (NRARB)alkyl include, but are not limited to, (amino)methyl, (dimethylamino)methyl, and (ethylamino)methyl.

The term "(NR$^A$R$^B$)alkoxy" as used herein, means a —NR$^A$R$^B$ group, as defined herein, appended to the parent molecular moiety through an alkoxy group, as defined herein. Representative examples of (NR$^A$R$^B$)alkoxy include, but are not limited to, (amino)methoxy, (dimethylamino)methoxy, and (diethylamino)ethoxy.

The term "(NR$^A$R$^B$)carbonyl" as used herein, means a —NR$^A$R$^B$ group, as defined herein, appended to the parent molecular moiety through a carbonyl group, as defined herein. Representative examples of (NR$^A$R$^B$)carbonyl include, but are not limited to, aminocarbonyl, (methylamino)carbonyl, (dimethylamino)carbonyl, and (ethylmethylamino)carbonyl.

The term "(NR$^A$R$^B$)sulfonyl" as used herein, means a —NR$^A$R$^B$ group, as defined herein, appended to the parent molecular moiety through a sulfonyl group, as defined herein. Representative examples of (NR$^A$R$^B$)sulfonyl include, but are not limited to, aminosulfonyl, (methylamino)sulfonyl, (dimethylamino)sulfonyl, and (ethylmethylamino)sulfonyl.

The term "sulfonyl" as used herein means a —S(O)$_2$— group.

The term "thioalkoxy" as used herein means an alkyl group, as defined herein, appended to the parent molecular moiety through a sulfur atom. Representative examples of thioalkoxy include, but are no limited to, methylthio, ethylthio, and propylthio.

Although typically it may be recognized that an asterisk is used to indicate that the exact subunit composition of a receptor is uncertain, for example α3b4* indicates a receptor that contains the α3 and β4 proteins in combination with other subunits, the term α7 as used herein is intended to include receptors wherein the exact subunit composition is both certain and uncertain. For example, as used herein α7 includes homomeric (α7)$_5$ receptors and α7* receptors, which denote a nAChR containing at least one α7 subunit.

Compounds of the Invention

Compounds of the invention can have the formula (I) as described above. More particularly, compounds of formula (I) can include, but are not limited to, compounds wherein Ar$^1$ is a group of the formula:

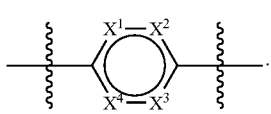
(a)

In a group of formula (a), X$^1$, X$^2$, X$^3$, and X$^4$ are each independently selected from the group consisting of N and —CR$^2$, wherein R$^2$ at each occurrence is independently selected from the group consisting of hydrogen, halogen, alkyl, —OR$^3$, and —NHR$^4$; and R$^3$ and R$^4$ are each independently selected from the group consisting of hydrogen, alkyl, alkylcarbonyl, and arylcarbonyl. Preferably, at least one of X$^1$, X$^2$, X$^3$, and X$^4$ is —CR$^2$, such that group of formula (a) contains 0, 1, 2, or 3 nitrogen atoms.

Specific examples of groups for Ar$^1$ are, for example,

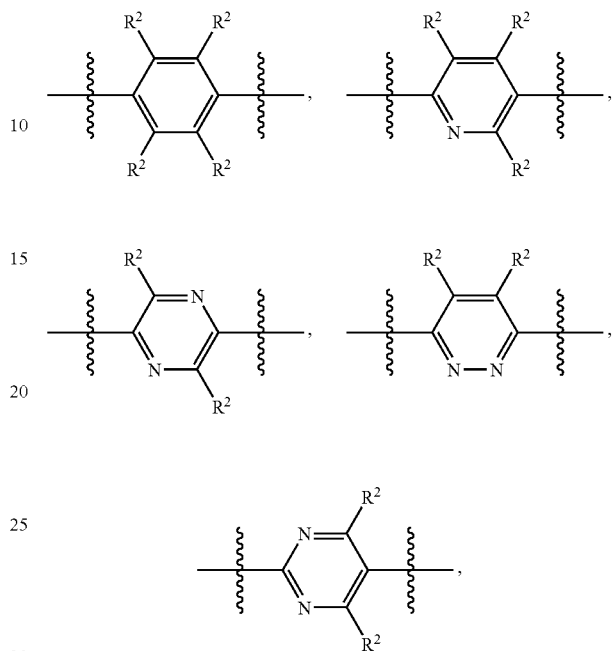

and the like, wherein R$^2$ is as previously defined for a group of formula (a).

Compounds of formula (I) can include, but are not limited to, compounds wherein Ar$^2$ is a group of the formula:

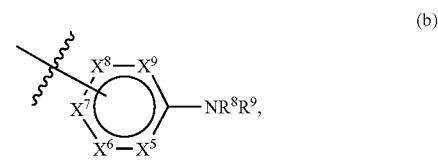
(b)

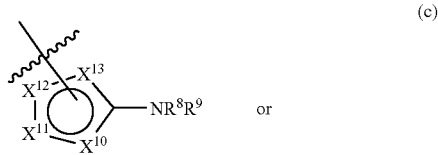
(c)

or

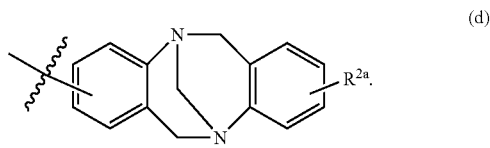
(d)

In a group of formula (b), X$^5$, X$^6$, X$^7$, X$^8$ and X$^9$ are each independently selected from the group consisting of N and —CR$^5$, wherein R$^5$ at each occurrence is as defined for a compound of formula (I), and preferably wherein R$^5$ is independently selected from the group consisting of hydrogen, halogen, nitro, alkyl, —OR$^6$, and —NHR$^7$; and R$^6$ and $R^7$ are each independently selected from the group consisting of hydrogen, alkyl, alkylcarbonyl, and arylcarbonyl. Preferably, at least one of $X^5$, $X^6$, $X^7$, $X^8$, and $X^9$ is —$CR^5$, such that group of formula (b) contains 0, 1, 2, or 3 nitrogen atoms. A group of formula (b) is attached through an atom represented by one of $X^5$, $X^6$, $X^7$, $X^8$ and $X^9$. The atom represented by $X^5$, $X^6$, $X^7$, $X^8$ and $X^9$ is carbon when it is attached to an atom from $Ar^1$.

In a group of formula (c), $X^{10}$, $X^{11}$, $X^{12}$, and $X^{13}$ are each independently selected from the group consisting of N, —$N(R^1)$, S, O and —$CR^5$, as previously defined for a formula (I), preferably wherein $R^5$ at each occurrence is independently selected from the group consisting of hydrogen, halogen, nitro, alkyl, —$OR^6$, and —$NHR^7$; and $R^6$ and $R^7$ are each independently selected from the group consisting of hydrogen, alkyl, alkylcarbonyl, and arylcarbonyl. Preferably, at least one of $X^{10}$, $X^{11}$, $X^{12}$, and $X^{13}$ is —$CR^5$, such that group of formula (c) contains 0, 1, 2, or 3 heteroatoms. A group of formula (c) is attached through an atom represented by one of $X^{10}$, $X^{11}$, $X^{12}$, and $X^{13}$. The atom represented by $X^{10}$, $X^{11}$, $X^{12}$, and $X^{13}$ is carbon when it is attached to the bond from $Ar^1$.

In a group of formula (d), $R^{2a}$ is a substituent as defined for compounds of formula (I), wherein $R^{2a}$ is hydrogen or alkyl. The substituent represented by $R^{2a}$ can be substituted on any carbon on the 6-carbon ring moiety of group (d).

The $NR^8R^9$ substituent in a group of formula (b) or (c) can be attached at any position, and preferably is attached at the 3- or 4-position as shown above. The groups represented by $R^8$ and $R^9$ are each independently selected from the group consisting of $R^8$ and $R^9$ are each independently selected from the group consisting of hydrogen, alkyl, aryl, arylalkyl, cycloalkylalkyl, alkylcarbonyl, —N=C(alkyl)(alkoxycarbonyl), alkoxycarbonyl, arylcarbonyl, aryloxycarbonyl, and alkylsulfonyl and, more preferably, hydrogen, alkyl, alkoxycarbonyl, and aryloxycarbonyl. More particularly, $R^8$ and $R^9$ are each independently selected from the group consisting of hydrogen, alkyl, benzyl, methanesulfonyl, phenyl, 4-methylphenyl, benzyloxycarbonyl, acetyl, cyclohexylmethyl, tert-butyloxycarbonyl, and —N=C(methyl)(ethoxycarbonyl). Even more particularly, $R^8$ preferably is selected from the group consisting of hydrogen and methyl, and $R^9$ preferably is selected from the group consisting of hydrogen, alkyl, benzyl, methanesulfonyl, phenyl, 4-methylphenyl, benzyloxycarbonyl, acetyl, cyclohexylmethyl, tert-butyloxycarbonyl, and —N=C(methyl)(ethoxycarbonyl).

Specific examples of groups for $Ar^2$ in a compound of formula (I) are, for example,

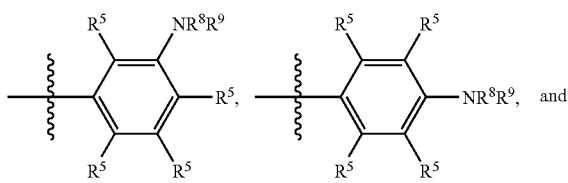

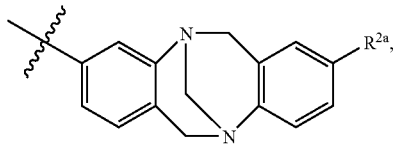

wherein $R^5$, $R^8$, and $R^9$ are as defined for formula (b) as previously described. More particularly, $R^5$ is selected from the group consisting of hydrogen, halogen, alkyl, aryl, alkylcarbonyl, arycarbonyl, $OR^6$ and $NR^8R^9$. $R^8$ and $R^9$ are each independently selected from the group consisting of hydrogen, alkyl, benzyl, methanesulfonyl, phenyl, benzyloxycarbonyl, acetyl, and butyloxycarbonyl. More specifically, $R^8$ can be selected from the group consisting of hydrogen and methyl, and $R^9$ can be selected from the group consisting of hydrogen, alkyl, benzyl, methanesulfonyl, phenyl, benzyloxycarbonyl, acetyl, and butyloxycarbonyl. $R^{2a}$ is as defined for a group of formula (d) as previously described and more, particularly, can be iodo or hydrogen.

Specific embodiments contemplated as part of the invention include, but are not limited to, compounds of formula (I), as defined, wherein:
4'-(1-azabicyclo[2.2.2]oct-3-yloxy)-1,1'-biphenyl-3-amine;
4'-[(3R)-1-azabicyclo[2.2.2]oct-3-yloxy]-1,1'-biphenyl-3-amine;
4'-(1-azabicyclo[2.2.2]oct-3-yloxy)-4-methyl-1,1'-biphenyl-3-amine;
4'-[(3R)-1-azabicyclo[2.2.2]oct-3-yloxy]-4-methyl-1,1'-biphenyl-3-amine;
4'-(1-azabicyclo[2.2.2]oct-3-yloxy)-1,1'-biphenyl-4-amine;
4'-[(3R)-1-azabicyclo[2.2.2]oct-3-yloxy]-1,1'-biphenyl-4-amine;
4'-[(3S)-1-azabicyclo[2.2.2]oct-3-yloxy]-1,1'-biphenyl-4-amine;
N-[4'-(1-azabicyclo[2.2.2]oct-3-yloxy)-1,1'-biphenyl-4-yl]-N-methylamine;
N-{4'-[(3R)-1-azabicyclo[2.2.2]oct-3-yloxy]-1,1'-biphenyl-4-yl}-N,N-dimethylamine;
N-[4'-(1-azabicyclo[2.2.2]oct-3-yloxy)-1,1'-biphenyl-4-yl]methanesulfonamide;
N-[4'-(1-azabicyclo[2.2.2]oct-3-yloxy)-1,1'-biphenyl-4-yl]-N-phenylamine;
3-[6-(1-azabicyclo[2.2.2]oct-3-yloxy)pyridin-3-yl]aniline;
4-[5-(1-azabicyclo[2.2.2]oct-3-yloxy)pyrazin-2-yl]aniline;
4-{5-[(3R)-1-azabicyclo[2.2.2]oct-3-yloxy]pyrazin-2-yl}aniline;
4-{5-[(3S)-1-azabicyclo[2.2.2]oct-3-yloxy]pyrazin-2-yl}aniline;
N-{4-[5-(1-azabicyclo[2.2.2]oct-3-yloxy)pyrazin-2-yl]phenyl}-N,N-dimethylamine;
N-{4-[5-(1-azabicyclo[2.2.2]oct-3-yloxy)pyrazin-2-yl]phenyl}acetamide;
4-[2-(1-azabicyclo[2.2.2]oct-3-yloxy)pyrimidin-5-yl]aniline;
4-{2-[(3R)-1-azabicyclo[2.2.2]oct-3-yloxy]pyrimidin-5-yl}aniline;
3-[2-(1-azabicyclo[2.2.2]oct-3-yloxy)pyrimidin-5-yl]aniline;

3-{2-[(3R)-1-azabicyclo[2.2.2]oct-3-yloxy]pyrimidin-5-yl}aniline;
3-{2-[(3S)-1-azabicyclo[2.2.2]oct-3-yloxy]pyrimidin-5-yl}aniline;
5-[2-(1-azabicyclo[2.2.2]oct-3-yloxy)pyrimidin-5-yl]-2-methylaniline;
N-1-azabicyclo[2.2.2]oct-3-yl-1,1'-biphenyl-4,4'-diamine;
4'-(1-oxy-1-aza-bicyclo[2.2.2]oct-3-yloxy)-biphenyl-3-ylamine;
[4'-(1-aza-bicyclo[2.2.2]oct-3-yloxy)-biphenyl-4-yl]-p-tolyl-amine;
[4'-(1-aza-bicyclo[2.2.2]oct-3-yloxy)-biphenyl-4-yl]-cyclohexylmethyl-amine;
2-[4-(1-aza-bicyclo[2.2.2]oct-3-yloxy)-phenyl]-8-iodo-6H,12H-5,11-methano-dibenzo[b,f][1,5]diazocine;
4-{6-[(3R)-1-aza-bicyclo[2.2.2]oct-3-yloxy]-pyridazin-3-yl}-phenylamine;
4{-6-[(3R)-1-aza-bicyclo[2.2.2]oct-3-yloxy]-pyridazin-3-yl}-2-bromo-phenylamine;
4-{6-[(3R)-1-aza-bicyclo[2.2.2]oct-3-yloxy]-pyridazin-3-yl}-2,6-dibromo-phenylamine;
2-({4-{6-[(3R)-1-aza-bicyclo[2.2.2]oct-3-yloxy]-pyridazin-3-yl}-phenyl]-hydrazono)-propionic acid ethyl ester;
(R)-N-{4-[6-(1-aza-bicyclo[2.2.2]oct-3-yloxy)-pyridazin-3-yl]-phenyl}-acetamide;
4-{6-[(3R)-1-aza-bicyclo[2.2.2]oct-3-yloxy]-pyridazin-3-yl}-2-nitro-phenylamine;
4-{6-[(3R)-1-aza-bicyclo[2.2.2]oct-3-yloxy]-pyridazin-3-yl}-benzene-1,2-diamine;
4-{2-[(3R)-1-aza-bicyclo[2.2.2]oct-3-yloxy]-pyrimidin-5-yl}-2-nitro-phenylamine; and
2-amino-4-{2-[(3R)-1-aza-bicyclo[2.2.2]oct-3-yloxy]-pyrimidin-5-yl]-phenol;

or pharmaceutically acceptable salts, esters, amides, and prodrugs thereof.

Compound names are assigned by using AUTONOM naming software, which is provided by MDL Information Systems GmbH (formerly known as Beilstein Informationssysteme) of Frankfurt, Germany, and is part of the CHEMDRAW® ULTRA v. 6.0.2 software suite.

Compounds of the invention may exist as stereoisomers wherein, asymmetric or chiral centers are present. These stereoisomers are "R" or "S" depending on the configuration of substituents around the chiral element. The terms "R" and "S" used herein are configurations as defined in IUPAC 1974 Recommendations for Section E, Fundamental Stereochemistry, Pure Appl. Chem., 1976, 45: 13-30. The invention contemplates various stereoisomers and mixtures thereof and are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Methods for Preparing Compounds of the Invention

As used in the descriptions of the schemes and the examples, certain abbreviations are intended to have the following meanings: Ac for acetyl; Bu for butyl; dba for dibenzylidine acetone; DEAD for diethyl azodicarboxylate; DMSO for dimethylsulfoxide; EtOAc for ethyl acetate; EtOH for ethanol; Et$_3$N for triethylamine; Et$_2$O for diethyl ether; HPLC for high pressure liquid chromatography; $^i$Pr for isopropyl; Me for methyl; MeOH for methanol; NBS for N-bromosuccinimide; OAc for acetoxy; o-tol. for o-toluene; Ph for phenyl; t-Bu for tert-butyl; and THF for tetrahydrofuran.

The reactions exemplified in the schemes are performed in a solvent appropriate to the reagents and materials employed and suitable for the transformations being effected. The described transformations may require modifying the order of the synthetic steps or selecting one particular process scheme over another in order to obtain a desired compound of the invention, depending on the functionality present on the molecule.

Nitrogen protecting groups can be used for protecting amine groups present in the described compounds. Such methods, and some suitable nitrogen protecting groups, are described in Greene and Wuts (Protective Groups In Organic Synthesis, Wiley and Sons, 1999). For example, suitable nitrogen protecting groups include, but are not limited to, tert-butoxycarbonyl (Boc), benzyloxycarbonyl (Cbz), benzyl (Bn), acetyl, and trifluoracetyl. More particularly, the Boc protecting group may be removed by treatment with an acid such as trifluoroacetic acid or hydrochloric acid. The Cbz and Bn protecting groups may be removed by catalytic hydrogenation. The acetyl and trifluoracetyl protecting groups may be removed by a hydroxide ion.

The methods described below can entail use of various isomers. Where the stereochemistry is shown in the Schemes, it is intended for illustrative purposes only.

Scheme 1

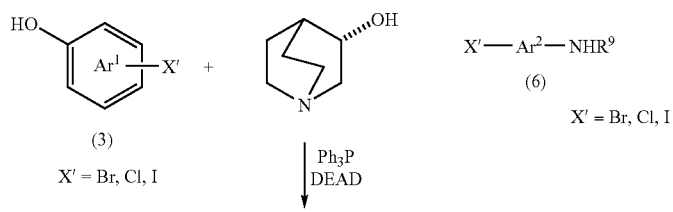

-continued

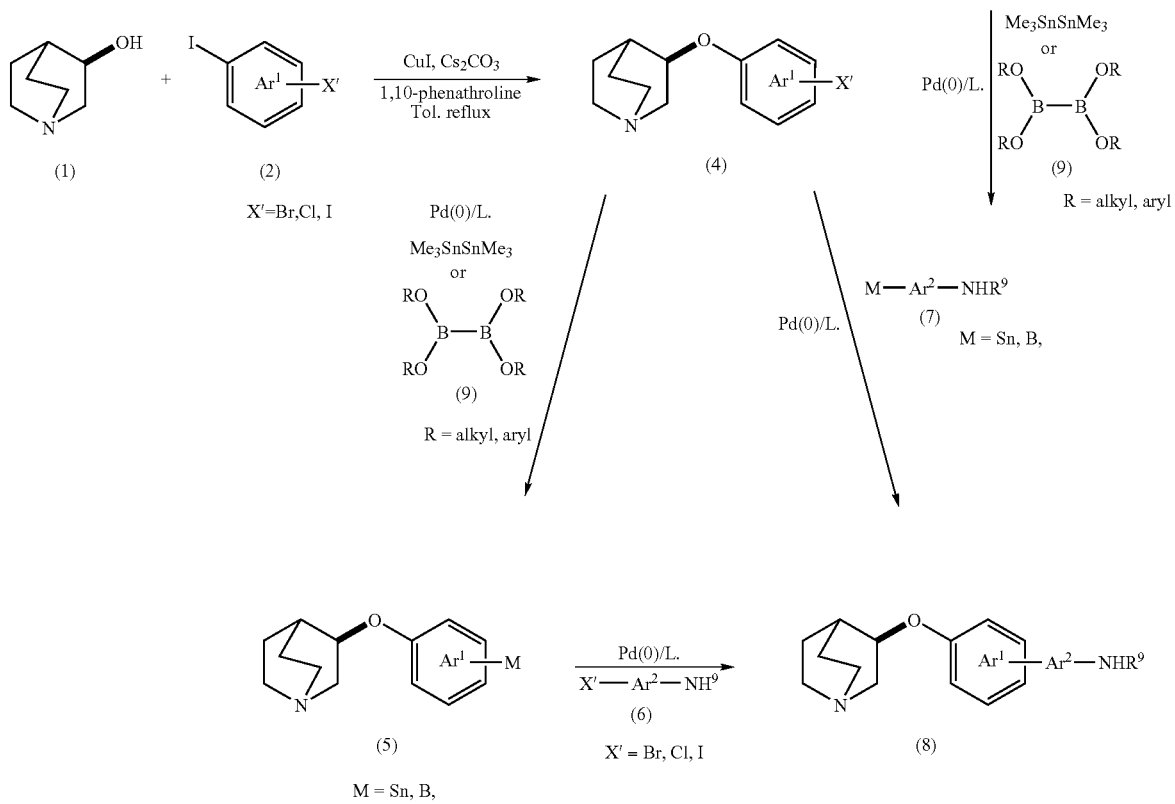

Quinuclidine ethers of general formula (8), wherein $Ar^1$, $Ar^2$, and $R^9$ are as defined in formula (I), can be prepared as described in Scheme 1. 3-Quinuclidinol of formula (1) is treated with a halophenyl iodide of formula (2), wherein X' is bromide, chloride, or iodide, with CuI and $Cs_2CO_3$ in 1,10-phenanthroline as described in Org. Lett., 2002, 4, 973, to obtain a halophenoxy quinuclidine of formula (4). Alternatively, a compound of formula can be obtained by treating 3-quinuclidinol with a halo phenyl alcohol of formula (3), wherein X' is bromide, chloride, or iodide, and diethyl azodicarboxylate in the presence of a phosphine, such as triphenylphosphine.

Compounds of formula (4) can be treated with a hexamethylditin or diboron reagent of fomula (9), such as bis (pinacolato)diboron and bis(catecholato)dibone, in the presence of a palladium catalyst to provide the corresponding tin or boron regent of formula (5), which is reacted with a desired halide of an amine-substituted aryl group represented by $Ar^2$—$NHR^9$ of formula (6), wherein X' is bromide, chloride, or iodide and $Ar^2$ and $NHR^9$ are as defined for a compound of formula (I) to provide compounds of formula (8). Alternatively, halides of a desired $Ar^2$ group can be treated with a hexamethylditin or diboron reagent of formula (9), such as bis(pinacolato)diboron and bis(catecholato) diboron, in the presence of a palladium catalyst to provide a corresponding tin or boronic acid reagent that is reacted with a compound of formula (4) in the presence of a palladium catalyst to provide a compound of formula (8).

Scheme 2

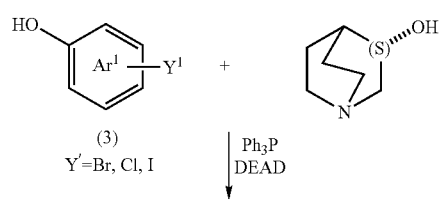

-continued

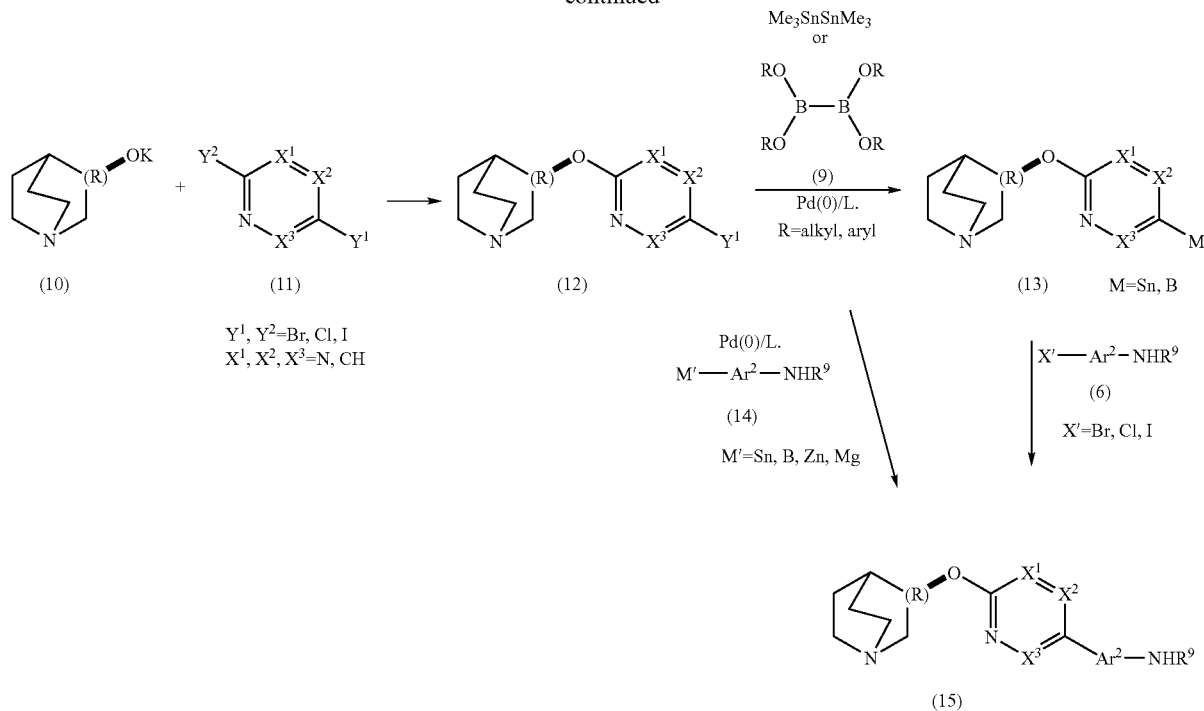

Quinuclidine ethers of formula (15), wherein Ar¹ is a nitrogen-containing heteroaryl, for example pyridazine, and Ar² and R⁹ are as defined for compounds of formula (I), can be prepared as shown in Scheme 2. Potassium quinuclidinoxide (10) can be reacted with a dihaloaromatic ring, for example, dichloropyridazine, of formula (11), wherein Y¹ and Y² are halides, for example bromide, chloride, or iodide, and X¹, X², and X³ are selected from N or CH, to obtain a quinuclidine ether of formula (12). The quinuclidine ether can be reacted with a tin, boron, zinc or Grignard reagent of a desired Ar² group substituted by —NHR⁹ of formula (14), wherein Ar² and R⁹ are as defined for a compound of formula (I), wherein M' is Sn, B, Zn, or Mg, to provide an amino-biaryl quinuclidine ether of formula (15). Alternatively, the quinuclidine ether of formula (12) can be treated with a hexamethylditin or diboron reagent of fomula (9), such as bis(pinacolato)diboron and bis(catecholato)diboron, to activate the aromatic group to provide (13), wherein M is tin or a boronic acid ester, and further treated with a halide of a desired Ar² substituted with —NHR⁹ in the presence of a palladium catalyst to provide compounds of formula (15).

Scheme 3

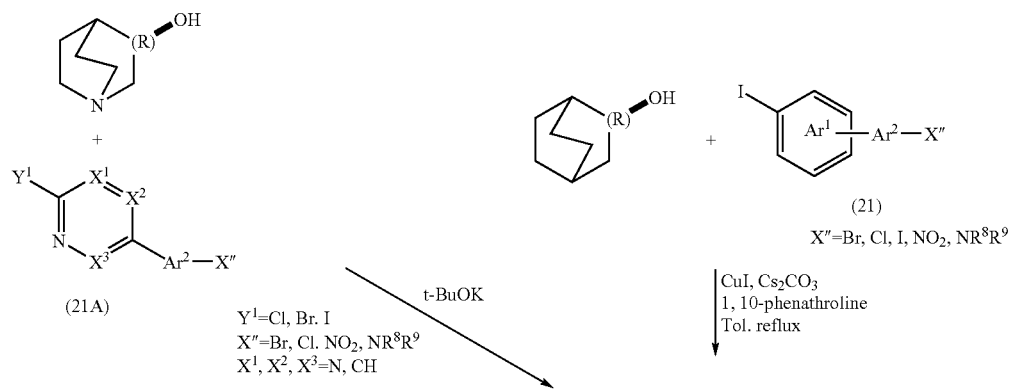

-continued

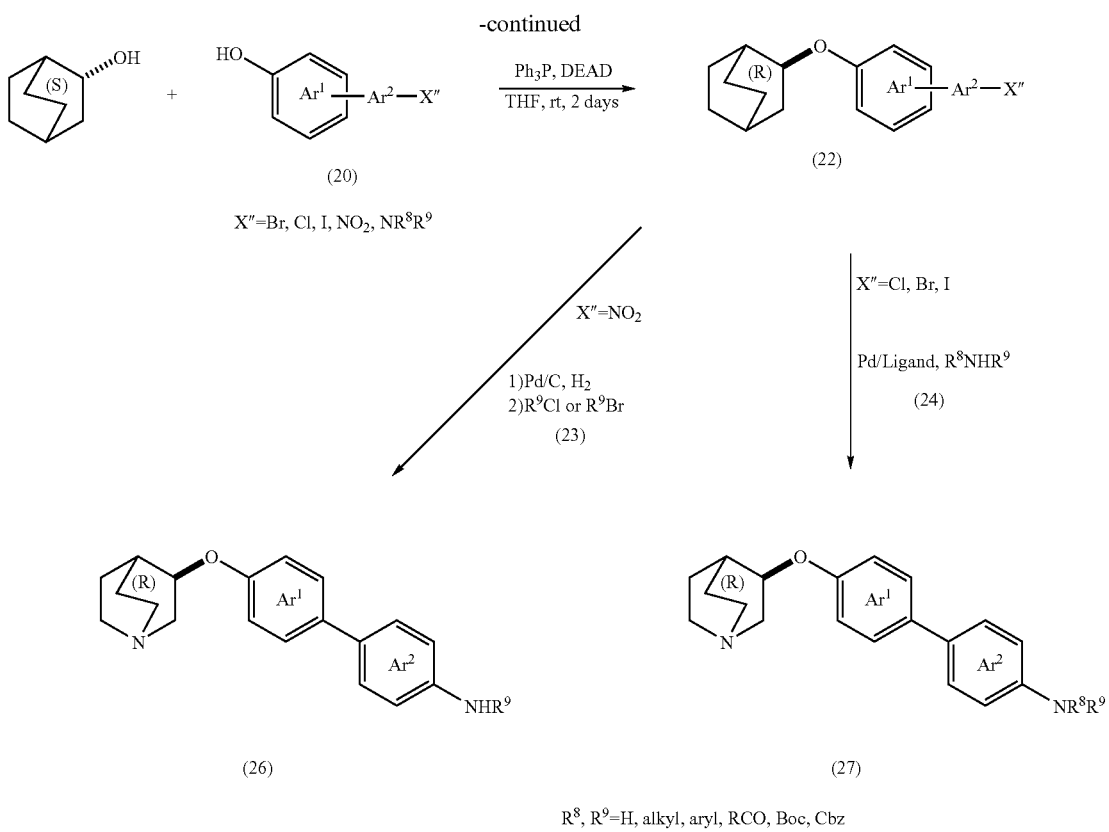

Quinuclidine ethers of formulas (26) and (27), wherein $Ar^1$, $Ar^2$, $R^8$, and $R^9$ are as defined for compounds of formula (I), can be obtained by the methods described in Scheme 3. Compounds of formula (20) can be treated with 3-quinuclidinol in the presence of a phosphine, for example triphenylphosphine, and diethyl azodicarboxylate to provide compounds of formula (22). Alternatively, compounds of formula (21), wherein X" is bromide, chloride, iodide, $NO_2$ or $NR^8R^9$ can be reacted with CuI, $Cs_2CO_3$ in 1,10-phenanthroline as described in Org. Lett. 2002, 4, 973, to provide a desired compound of formula (22). Compounds of formula (22) can also be obtained by coupling 3-quinuclidinol with coupounds of formula (21A) in the presence of t-BuOK. Compounds of formula (22), wherein X" is $NO_2$, can be reduced with hydrogen in the presence of a palladium catalyst and reacted with a chloride or bromide of a desired $R^9$ group of formula (23), wherein $R^9$ is hydrogen, alkyl, aryl, alkycarbonyl, alkoxycarbonyl, arylcarbonyl, or aryloxycarbonyl, to provide compounds of formula (26). Compounds of formula (22), wherein X" is bromide, chloride, or iodide, can be treated with a compound $R^8NHR^9$ of formula (24), wherein $R^8$ and $R^9$ are as previously described for $R^9$ in compounds of formula (23), to provide a corresponding compound of formula (27).

Scheme 4

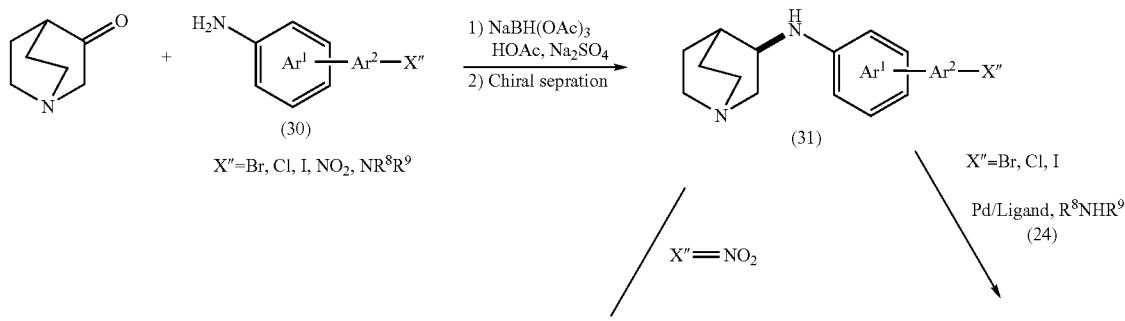

-continued

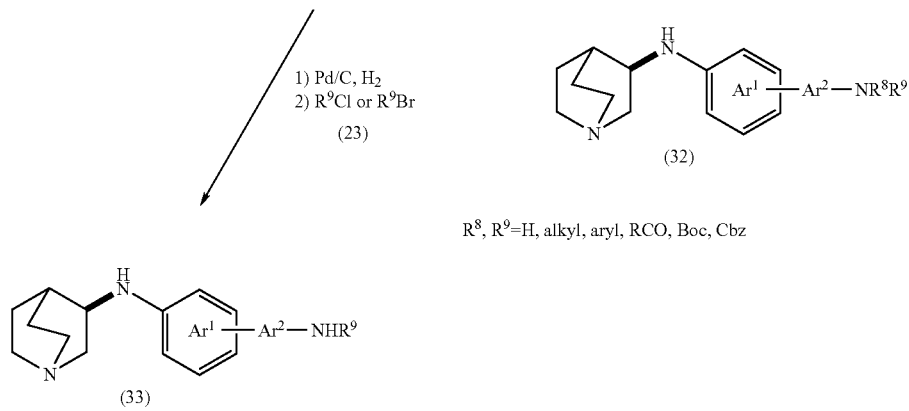

$R^8$, $R^9$=H, alkyl, aryl, RCO, Boc, Cbz

Compounds of formulas (32) and (33), wherein $Ar^1$, $Ar^2$, $R^8$, and $R^9$ are as defined for compounds of formula (I), can be prepared as shown in Scheme 4. 3-Quinuclidinone and a halobiarylamine of formula (30), wherein X" is bromide, chloride, iodide, $NO_2$ or $NR^8R^9$, can be treated with sodium triacetoxy borohydride and $Na_2SO_4$ in acetic acid to provide a racemic compound of formula (31) as described in Tetrahedron Lett. 1996, 37, 6045. The racemate of formula (31) can be resolved into its respective isomers by resolution with D-tartaric acid or via chiral HPLC chromatography on a Chiracel®-OD chromatography column using methods well-known in the art to provide the (R)- and (S)-isomers of formulas (31), respectively. Compounds of formula (31), wherein X" is bromide, chloride, or iodide, can be treated with a compound $R^8NHR^9$ of formula (24), wherein $R^8$ and $R^9$ are as previously described for $R^9$ in compounds of formula (23), to provide a corresponding compound of formula (32). Compounds of formula (31), wherein X" is $NO_2$, can be reduced with hydrogen in the presence of a palladium catalyst and reacted with a chloride or bromide of a desired $R^9$ group of formula (23), wherein $R^9$ is hydrogen, alkyl, aryl, alkycarbonyl, alkoxycarbonyl, arylcarbonyl, or aryloxycarbonyl, to provide compounds of formula (33).

Scheme 5

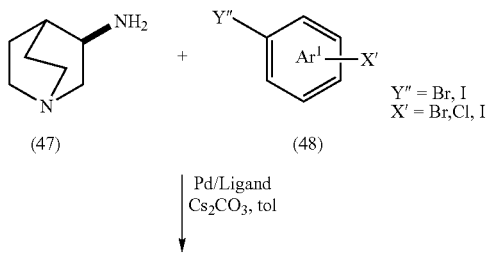

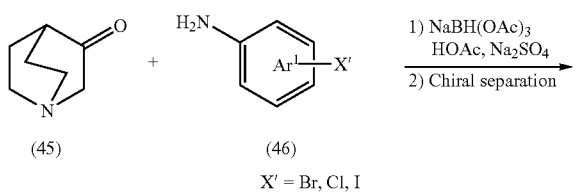

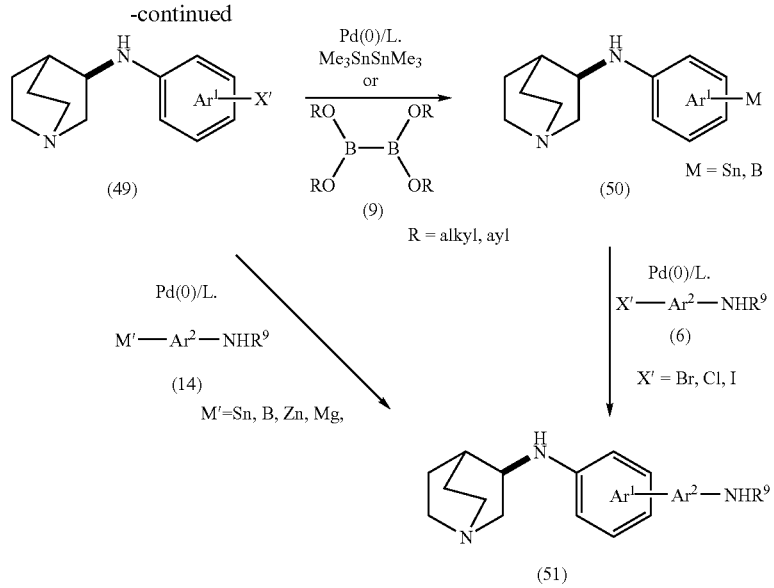

Compounds of formula (51), wherein Y is —NH— and Ar¹, Ar², R⁸, and R⁹ are as described for compounds of formula (I), can be prepared as shown in Scheme 5. 3-Quinuclidinone (45) and a haloarylamine of formula (46), wherein X' is bromide, chloride, or iodide, can be treated with sodium triacetoxy borohydride and Na₂SO₄ in acetic acid to provide a racemic compound of formula (49). The racemate of formula (49) can be resolved into its respective isomers by resolution with D-tartaric acid or via chiral HPLC chromatography on a Chiracel®-OD chromatography column using methods well-known in the art to provide the (R)- and (S)-isomers of formulas (49), respectively. Alternatively, a compound of formula (49) can be obtained by treating 3-aminoquinuclidine (47) with haloaromatic group as described in formula (48) with Cs₂CO₃ in the presence of palladium catalyst, preferably in toluene. A compound of formula (49) can be treated with a tin or boronic acid under conditions previously described to provide the corresponding tin or boronic acid reagent of formula (50), which can be reacted with the halide of a desired group represented by Ar² in a compound of formula (6) to provide a compound of formula (51). Alternatively, the compound of formula (49) is treated with a tin or boronic acid ester of the desired Ar² group in the presence of a palladium catalyst to provide a compound of formula (51).

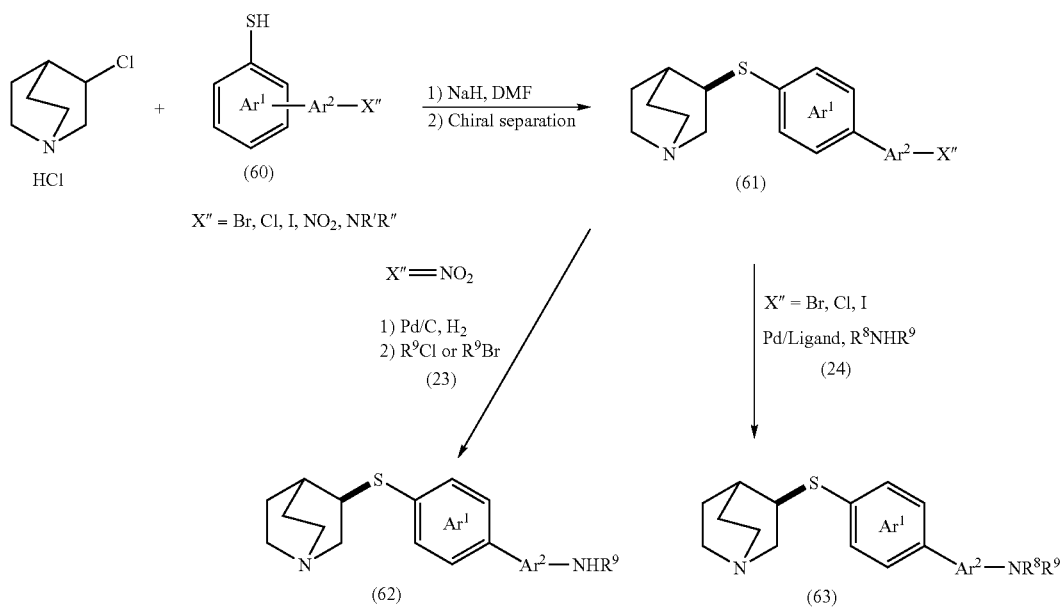

Quinuclidine biarylsulfides of formula (62) and (63), wherein Ar¹, Ar², R⁸, and R⁹ are as defined for formula (I), can be obtained by the methods described in Scheme 6. 3-Chloroquinuclidine can be reacted with a halobiarylthiol of formula (60), wherein X" is bromide, chloride, iodide, NO₂, or NR⁸R⁹, wherein R⁸ and R⁹ are as defined for a compound of formula (I), as described in J. Med. Chem. 1999, 42, 1306, to provide a racemic compound of formula (61). The racemate of formula (61) can be resolved into its respective isomers by resolution with D-tartaric acid or via chiral HPLC chromatography on a Chiracel®-OD chromatography column using methods well-known in the art to provide the (R)- and (S)-isomers of formulas (61), respectively. Compounds of formula (61), wherein X" is NO₂, can be reduced with hydrogen in the presence of a palladium catalyst and reacted with a chloride or bromide of a desired R⁹ group of formula (23), wherein R⁹ is hydrogen, alkyl, aryl, alkycarbonyl, alkoxycarbonyl, arylcarbonyl, or aryloxycarbonyl, to provide compounds of formula (62). Compounds of formula (61), wherein X" is bromide, chloride, or iodide, can be treated with a compound R⁸NHR⁹ of formula (24), wherein R⁸ and R⁹ are as previously described for R⁹ in compounds of formula (23), to provide a corresponding compound of formula (63).

X' is bromide, chloride, or iodide, to provide a racemic compound of formula (77). The racemate of formula (77) can be resolved into its respective isomers by resolution with D-tartaric acid or via chiral HPLC chromatography on a Chiracel®-OD chromatography column using methods well-known in the art to provide the (R)- and (S)-isomers of formulas (77), respectively. The compound of formula (77) can be treated with a tin, boron, zinc or Grignard reagent of a desired group for Ar², as defined for a compound of formula (I), to provide a compound of formula (79). Alternatively, the compound of formula (77) can be reacted with hexamethylditin or diboron of formula (9), such as bis (pinacolato)diboron and bis(catecholato)diboron, in the presence of a palladium catalyst to provide a compound of formula (78), which is reacted with the halide of a desired Ar² group in the presence of a palladium catalyst to provide a compound of formula (79).

Compounds of formula (I) wherein A is N can be converted to compounds of formula (I) wherein A is N⁺—O⁻ by treatment with an oxidizing agent. Examples of the oxidizing agent include, but not limited to, aqueous hydrogen peroxide and m-chloroperbenzoic acid. The reaction is generally performed in a solvent such as, but not limited to,

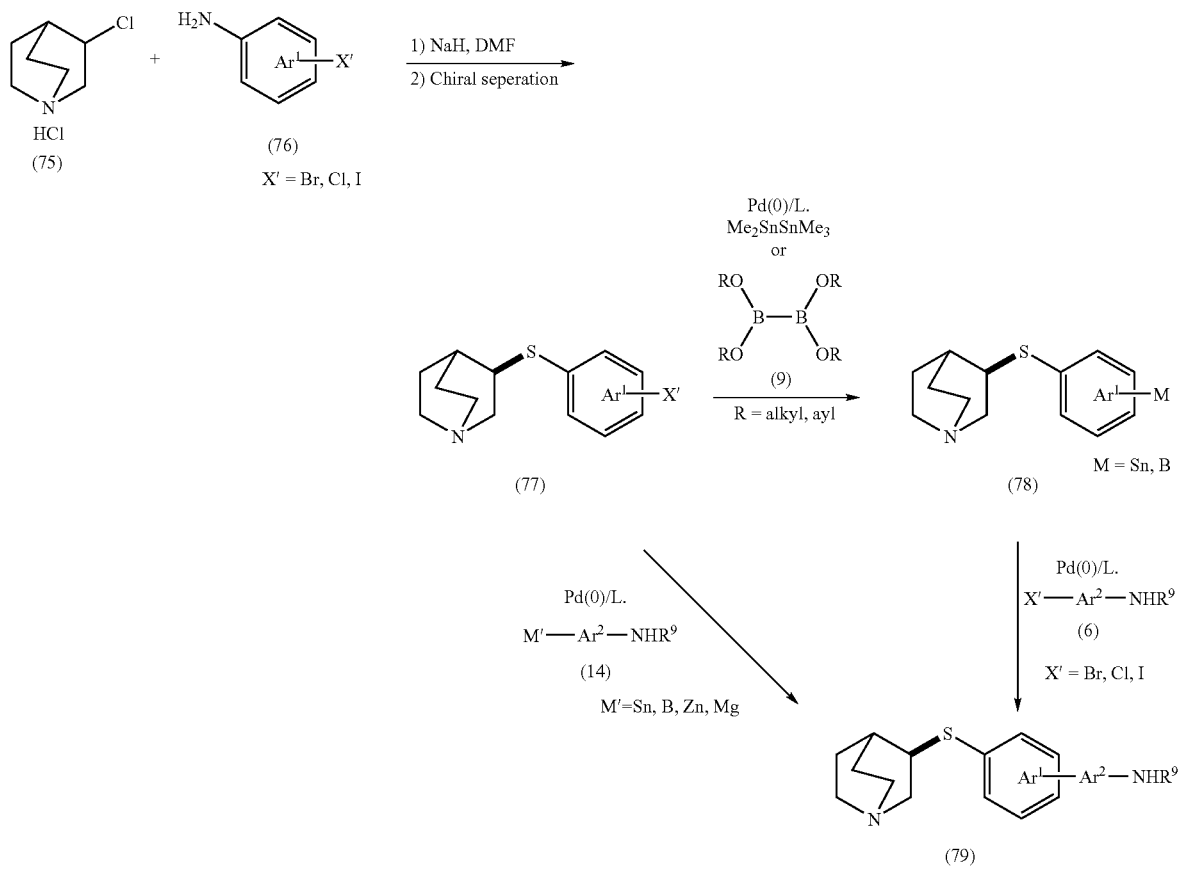

Compounds of formula (79), wherein Y is S and Ar¹, Ar², and R⁹ are as defined in a compound of formula (I), can be prepared as shown in Scheme 7. 3-Chloroquinuclidine (75) can be reacted with a haloarylthiol of formula (76), wherein acetonitrile, water, dichloromethane, acetone or mixture thereof, preferably a mixture of acetonitrile and water, at a temperature from about room temperature to about 80° C., for a period of about 1 hour to about 4 days.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, carbonic, fumaric, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof, vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or welting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts, esters, or amides derived from inorganic or organic acids. The term "pharmaceutically acceptable salts, esters and amides," as used herein, include salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also can be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds of formula (I).

Methods of the Invention

Compounds and compositions of the invention are useful for modulating the effects of nAChRs, and more particularly α7 nAChRs. In particular, the compounds and compositions of the invention can be used for treating and preventing disorders modulated by α7 nAChRs. Typically, such disorders can be ameliorated by selectively modulating the α7 nAChRs in a mammal, preferably by administering a compound or composition of the invention, either alone or in combination with another active agent, for example, as part of a therapeutic regimen.

The compounds of the invention, including but not limited to those specified in the examples, possess an affinity for nAChRs, and more particularly α7 nAChRs. As α7 nAChRs ligands, the compounds of the invention can be useful for the treatment and prevention of a number of α7 nAChR-mediated diseases or conditions.

For example, α7 nAChRs have been shown to play a significant role in enhancing cognitive function, including aspects of learning, memory and attention (Levin, E. D., J.

Neurobiol. 53: 633-640, 2002). As such, α7 ligands are suitable for the treatment of cognitive disorders including, for example, attention deficit disorder, attention deficit hyperactivity disorder (ADHD), Alzheimer's disease (AD), mild cognitive impairment, senile dementia, AIDS dementia, Pick's Disease, dementia associated with Lewy bodies, and dementia associated with Down's syndrome, as well as cognitive deficits associated with schizophrenia.

In addition, α7-containing nAChRs have been shown to be involved in the neuroprotective effects of nicotine both in vitro (Jonnala, R. B. and Buccafusco, J. J., J. Neurosci. Res. 66: 565-572, 2001) and in vivo (Shimohama, S. et al., Brain Res. 779: 359-363, 1998). More particularly, neurodegeneration underlies several progressive CNS disorders, including, but not limited to, Alzheimer's disease, Parkinson's disease, amyotrophic lateral sclerosis, Huntington's disease, dementia with Lewy bodies, as well as diminished CNS function resulting from traumatic brain injury. For example, the impaired function of α7 nAChRs by β-amyloid peptides linked to Alzheimer's disease has been implicated as a key factor in development of the cognitive deficits associated with the disease (Liu, Q.-S., Kawai, H., Berg, D. K., PNAS 98: 4734-4739, 2001). The activation of α7 nAChRs has been shown to block this neurotoxicity (Kihara, T. et al., J. Biol. Chem. 276: 13541-13546, 2001). As such, selective ligands that enhance α7 activity can counter the deficits of Alzheimer's and other neurodegenerative diseases.

Schizophrenia is a complex disease that is characterized by abnormalities in perception, cognition, and emotions. Significant evidence implicates the involvement of α7 nAChRs in this disease, including a measured deficit of these receptors in post-mortem patients (Leonard, S. Eur. J. Pharmacol. 393: 237-242, 2000). Deficits in sensory processing (gating) are one of the hallmarks of schizophrenia. These deficits can be normalized by nicotinic ligands that operate at the α7 nAChR (Adler L. E. et al., Schizophrenia Bull. 24: 189-202, 1998; Stevens, K. E. et al., Psychopharmacology 136: 320-327, 1998). Thus, α7 ligands demonstrate potential in the treatment schizophrenia.

Angiogenesis, a process involved in the growth of new blood vessels, is important in beneficial systemic functions, such as wound healing, vascularization of skin grafts, and enhancement of circulation, for example, increased circulation around a vascular occlusion. Non-selective nAChR agonists like nicotine have been shown to stimulate angiogenesis (Heeschen, C. et al., Nature Medicine 7: 833-839, 2001). Improved angiogenesis has been shown to involve activation of the α7 nAChR (Heeschen, C. et al, J. Clin. Invest. 110: 527-536, 2002). Therefore, nAChR ligands that are selective for the α7 subtype offer improved potential for stimulating angiogenesis with an improved side effect profile.

A population of α7 nAChRs in the spinal cord modulate serotonergic transmission that have been associated with the pain-relieving effects of nicotinic compounds (Cordero-Erausquin, M. and Changeux, J.-P. PNAS 98: 2803-2807, 2001). The α7 nAChR ligands demonstrate therapeutic potential for the treatment of pain states, including acute pain, post-surgical pain, as well as chronic pain states including inflammatory pain and neuropathic pain. Moreover, α7 nAChRs are expressed on the surface of primary macrophages that are involved in the inflammation response, and that activation of the α7 receptor inhibits release of TNF and other cytokines that trigger the inflammation response (Wang, H. et al Nature 421: 384-388, 2003). Therefore, selective α7 ligands demonstrate potential for treating conditions involving inflammation and pain.

The mammalian sperm acrosome reaction is an exocytosis process important in fertilization of the ovum by sperm. Activation of an α7 nAChR on the sperm cell has been shown to be essential for the acrosome reaction (Son, J.-H. and Meizel, S. Biol. Reproduct. 68: 1348-1353 2003). Consequently, selective α7 agents demonstrate utility for treating fertility disorders.

Compounds of the invention are particularly useful for treating and preventing a condition or disorder affecting cognition, neurodegeneration, and schizophrenia.

Cognitive impairment associated with schizophrenia often limits the ability of patients to function normally, a symptom not adequately treated by commonly available treatments, for example, treatment with an atypical antipsychotic. (Rowley, M. et al., J. Med. Chem. 44: 477-501, 2001). Such cognitive deficit has been linked to dysfunction of the nicotinic cholinergic system, in particular with decreased activity at α7 receptors. (Friedman, J. I. et al., Biol Psychiatry, 51: 349-357, 2002). Thus, activators of α7 receptors can provide useful treatment for enhancing cognitive function in schizophrenic patients who are being treated with atypical antipsychotics. Accordingly, the combination of an α7 nAChR ligand and an atypical antipsychotic would offer improved therapeutic utility. Specific examples of suitable atypical antipsychotics include, but are not limited to, clozapine, risperidone, olanzapine, quietapine, ziprasidone, zotepine, iloperidone, and the like.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.10 mg/kg body weight to about 1 g/kg body weight. More preferable doses can be in the range of from about 0.10 mg/kg body weight to about 100 mg/kg body weight. If desired, the effective daily dose can be divided into multiple doses for purposes of administration. Consequently, single dose compositions may contain such amounts or submultiples thereof to make up the daily dose.

The compounds and processes of the invention will be better understood by reference to the following examples and reference examples, which are intended as an illustration of and not a limitation upon the scope of the invention.

EXAMPLES

Example 1

4'-(1-azabicyclo[2.2.2]oct-3-yloxy)-1,1'-biphenyl-3-amine

Example 1A 3-(4-iodophenoxy)quinuclidine

3-Hydroxy quinuclidine (Aldrich, 2.54 g, 20 mmol) in toluene (anhydrous, Aldrich, 50 mL) was treated with 1,4-diiodobenzene (Aldrich, 7.9 g, 24 mmol), CuI (Strem Chemicals, 0.38 g, 2 mmol), and 1,10-phenanthroline (Aldrich, 0.72 g, 4 mmol) and heated at 110° C. for 40 hours. The reaction mixture was allowed to cool to room temperature, diluted with chloroform (100 mL), and washed with water (2×10 mL). The organic phase was concentrated and the title compound was purified by chromatography (SiO$_2$, CH$_2$Cl$_2$: MeOH:NH$_3$.H$_2$O, 90:10:1, R$_f$ 0.20) as an oil (3.7 g, yield, 56%). $^1$H NMR (MeOH-d$_4$, 300 MHz) δ 1.40-1.56 (m, 1H), 1.64-1.80 (m, 2H), 1.90-2.08 (m, 1H), 2.10-2.21 (m, 1H), 2.60-3.00 (m, 5H), 3.34-3.40 (m, 1H), 4.46 (m, 1H), 6.73 (d, J=8.8 Hz, 2H), 7.56 (d, J=8.8, Hz, 2H), ppm. MS (DCl/NH$_3$) m/z 330 (M+H)$^+$.

Example 1B

4'-(1-azabicyclo[2.2.2]oct-3-yloxy)-1,1'-biphenyl-3-amine

The product of Example 1A (330 mg, 1 mmol) in toluene (8 mL) was treated with 3-amino-phenylboronic acid (Lancaster, 276 mg, 2 mmol), Pd$_2$(dba)$_3$ (Strem Chemicals, 18.3 mg, 0.02 mmol), 1,3-bis(2,6-di-i-propylphenyl)imidazolium chloride, 95%, 26.9 mg, 0.06 mmol), and Na$_2$CO$_3$ (aqueous, 2M, 2 mL, 4 mmol) at 110° C. for 15 hours. The reaction mixture was allowed to cool to room temperature, diluted with ethyl acetate (20 mL), and washed with brine (2×5 mL). The organic phase was concentrated and the title compound was purified by chromatography (SiO$_2$, CH$_2$Cl$_2$:MeOH: NH$_3$.H$_2$O, 90:10:2, R$_f$ 0.10) as oil (230 mg, yield, 78%). $^1$H NMR (MeOH-d$_4$, 300 MHz) δ 1.40-1.53 (m, 1H), 1.62-1.85 (m, 2H), 1.96-2.20 (m, 2H), 2.80-2.94 (m, 5H), 3.28-3.40 (m, 1H), 4.52-4.60 (m, 1H), 6.66 (ddd, J=7.8, 2.3, 1.0 Hz, 1H), 6.89 (ddd, J=7.3, 1.6, 1.0 Hz, 1H), 6.92-6.96 (m, 3H), 7.13 (t, J=7.8, Hz, 1H), 7.48 (dt, J=8.8, 2.1 Hz, 2H) ppm. MS (DCl/NH$_3$) m/z 295 (M+H)$^+$.

Example 1C

4'-(1-azabicyclo[2.2.2]oct-3-yloxy)-1,1'-biphenyl-3-amine hydrochloride

The product of Example 1B (230 mg, 0.78 mmol) in ethyl acetate (5 mL) was treated with 4M HCl in 1,4-dioxane (0.5 mL, 2 mmol). The title compound was obtained as solid (210 mg, yield, 74%): $^1$H NMR (MeOH-d$_4$, 300 MHz) δ 1.82-2.21 (m, 3H), 2.30-2.42 (m, 1H), 2.55-2.62 (m, 1H), 3.35-3.50 (m, 5H), 3.82-3.96 (m, 1H), 4.95-5.02 (m, 1H), 7.11 (dt, J=8.8, 2.0 Hz, 2H), 7.34 (ddd, J=9.1, 2.3, 1.3 Hz, 1H), 7.57-7.66 (m, 4H), 7.72 (ddd, J=7.8, 1.6, 1.0 Hz, 1H) ppm. MS (DCl/NH$_3$) m/z 295 (M+H)$^+$. Anal. Calculated for C$_{19}$H$_{22}$N$_2$O.2.0HCl.0.2H$_2$O: C, 61.52; H, 6.63; N, 7.55. Found: C, 61.22; H, 6.44; N, 7.38.

Example 2

4'-[(3R)-1-azabicyclo[2.2.2]oct-3-yloxy]-1,1'-biphenyl-3-amine

Example 2A (3R)-3-(4-iodophenoxy)quinuclidine (3R)-Hydroxy quinuclidine (Aldrich, 0.64 g, 5 mmol) was treated with 1,4-diiodobenzene (Aldrich, 1.98 g, 6 mmol) according to the procedure of Example 1A. The title compound was purified by chromatography (SiO$_2$, CH$_2$Cl$_2$: MeOH:NH$_3$.H$_2$O, 90:10:1, R$_f$ 0.30) as a solid (0.50 g, yield, 30%). $^1$H NMR (MeOH-d$_4$, 300 MHz) δ 1.40-1.56 (m, 1H), 1.64-1.80 (m, 2H), 1.90-2.05 (m, 1H), 2.09-2.17 (m, 1H), 2.71-3.00 (m, 5H), 3.34-3.40 (m, 1H), 4.44-4.52 (m, 1H), 6.72 (d, J=8.8 Hz, 2H), 7.55 (d, J=8.8, Hz, 2H), ppm. MS (DCl/NH$_3$) m/z 330 (M+H)$^+$.

Example 2B

4'-[(3R)-1-azabicyclo[2.2.2]oct-3-yloxy]-1,1'-biphenyl-3-amine

The product of Example 1A (165 mg, 0.5 mmol) was treated with 3-amino-phenylboronic acid (Lancaster, 137 mg, 1 mmol) according to the procedure of Example 1B. The title compound was purified by chromatography (SiO$_2$, CH$_2$Cl$_2$:MeOH:NH$_3$.H$_2$O, 90:10:2, R$_f$ 0.25) as an oil (38 mg, yield, 26%). $^1$H NMR (MeOH-d$_4$, 300 MHz) δ 1.40-1.53 (m, 1H), 1.62-1.85 (m, 2H), 1.96-2.20 (m, 2H), 2.80-2.94 (m, 5H), 3.28-3.40 (m, 1H), 4.52-4.60 (m, 1H), 6.66 (ddd, J=7.8, 2.3, 1.0 Hz, 1H), 6.89 (ddd, J=7.3, 1.6, 1.0 Hz, 1H), 6.92-6.96 (m, 3H), 7.13 (t, J=7.8, Hz, 1H), 7.48 (dt, J=8.8, 2.1 Hz, 2H) ppm. MS (DCl/NH$_3$) m/z 295 (M+H)$^+$.

Example 2C

4'-[(3R)-1-azabicyclo[2.2.2]oct-3-yloxy]-1,1'-biphenyl-3-amine fumarate

The product of Example 2B (38 mg, 0.13 mmol) in ethyl acetate/methanol (3 mL, 10:1) was treated with fumaric acid (17 mg, 0.14 mmol) at ambient temperature overnight. The title compound was obtained as a solid (31 mg, yield, 55%): $^1$H NMR (MeOH-d$_4$, 300 MHz) δ 1.82-2.21 (m, 3H), 2.30-2.42 (m, 1H), 2.55-2.62 (m, 1H), 3.35-3.50 (m, 5H), 3.75-3.82 (m, 1H), 4.95-5.02 (m, 1H), 6.65-6.72 (m, 3H), 6.88 (ddd, J=7.8, 2.7, 1.0 Hz, 1H), 6.92 (t, J=2.0 Hz, 1H), 7.01 (dt, J=8.8, 2.1 Hz, 2H), 7.14 (t, J=7.8 Hz, 1H), 7.53 (dt, J=8.8, 2.5 Hz, 2H) ppm. MS (DCl/NH$_3$) m/z 295 (M+H)$^+$. Anal. Calculated for C$_{19}$H$_{22}$N$_2$O.1.19C$_4$H$_4$O$_4$: C, 65.98; H, 6.24; N, 6.48. Found: C, 66.00; H, 6.00; N, 6.38.

Example 3

4'-(1-azabicyclo[2.2.2]oct-3-yloxy)-4-methyl-1,1'-biphenyl-3-amine hydrochloride The product of Example 1A (330 mg, 1 mmol) was treated with 3-amino-4-methyl-phenylboronic acid (Lancaster, 302 mg, 2 mmol) according to the procedure of Example 1B. The free base of the title compound was purified by chromatography (SiO$_2$, CH$_2$Cl$_2$:MeOH:NH$_3$H$_2$O, 90:10:2, R$_f$ 0.10) as oil (230 mg, yield, 75%). The free base of the title compound (230 mg, 0.75 mmol) in ethyl acetate (5 mL) was treated with 4M HCl in 1,4-dioxane (0.5 mL, 2 mmol). The title compound was obtained as solid (180 mg, yield, 74%): $^1$H NMR (MeOH-d$_4$, 300 MHz) δ 1.85-2.19 (m, 3H), 2.28-2.38 (m, 1H), 2.43 (s, 3H), 2.51-2.57 (m, 1H), 3.31-3.45 (m, 5H), 3.82-3.89 (m, 1H), 4.93-4.99 (m, 1H), 7.13 (dt, J=8.8, 3.0 Hz, 2H), 7.44 (d, J=8.8 Hz, 1H), 7.56-7.66 (m, 4H) ppm. MS (DCl/NH$_3$) m/z 309 (M+H)$^+$. Anal. Calculated for C$_{19}$H$_{22}$N$_2$O.2.0HCl.0.1H$_2$O: C, 62.70; H, 6.89; N, 7.31. Found: C, 62.52; H, 6.59; N, 7.35.

Example 4

4'-[(3R)-1-azabicyclo[2.2.2]oct-3-yloxy]-4-methyl-1,1'-biphenyl-3-amine

Example 4A

4'-[(3R)-1-azabicyclo[2.2.2]oct-3-yloxy]-4-methyl-1,1'-biphenyl-3-amine

The product of Example 2A (165 mg, 0.5 mmol), was treated with 3-amino-4-methyl-phenylboronic acid (151 mg, 1 mmol) according to the procedure of Example 2B. The title product was purified by chromatography (SiO$_2$, CH$_2$Cl$_2$:MeOH:NH$_3$.H$_2$O, 90:10:1, R$_f$ 0.25) as a solid (104 mg, yield, 68%). $^1$H NMR (MeOH-d$_4$, 300 MHz) δ 1.45-1.58 (m, 1H), 1.64-1.89 (m, 2H), 2.00-2.13 (m, 1H), 2.15-2.23 (m, 4H), 2.76-3.02 (m, 5H), 3.30-3.40 (m, 1H), 4.51-4.59 (m, 1H), 6.6.84 (dd, J=7.8, 2.0 Hz, 1H), 6.90-6.97 (m, 3H), 7.02 (d, J=7.8 Hz, 1H), 7.47 (dt, J=8.8, 2.0 Hz, 2H) ppm. MS (DCl/NH$_3$) m/z 309 (M+H)$^+$.

Example 4B

4'-[(3R)-1-azabicyclo[2.2.2]oct-3-yloxy]-4-methyl-1,1'-biphenyl-3-amine fumarate The product of Example 4A in ethyl acetate/ethanol (v.1:1, 4 mL) was treated with fumaric acid (40 mg, 0.34 mmol) at ambient temperature for 15 hours. The title compound was obtained as a solid (115 mg, yield, 77%). $^1$H NMR (MeOH-d$_4$, 300 MHz) δ 1.79-2.16 (m, 3H), 2.18 (s, 3H), 2.24-2.39 (m, 1H), 2.46-2.54 (m, 1H), 3.20-3.42 (m, 5H), 3.71-3.81 (m, 1H), 6.68 (s, 2H), 6.83 (dd, J=7.8, 1.7 Hz, 1H), 6.94 (d, J=1.7 Hz, 1H), 6.97-7.06 (m, 3H), 7.51 (dt, J=8.5, 2.1 Hz, 2H) ppm. MS (Cl/NH$_3$): m/z 309 (M+H)$^+$. Anal. Calculated for C$_{20}$H$_{24}$N$_2$O.C$_4$H$_4$O$_4$: C, 67.91; H, 6.65; N, 6.60. Found: C, 67.62; H, 6.45; N, 6.43.

Example 5

4'-(1-azabicyclo[2.2.2]oct-3-yloxy)-1,1'-biphenyl-4-amine

Example 5A

3-[(4'-nitro-1,1'-biphenyl-4-yl)oxy]quinuclidine

3-Quinuclidinol (Aldrich, 254 mg, 2 mmol) in tetrahydrofuran (anhydrous, Aldrich, 10 mL) was treated with 4'-nitro-1,1'-biphenyl-4-ol (TCl, 215 mg, 1 mmol) with DIAD (di-isopropyl azadicarboxylate, Aldrich, 404 mg, 2 mmol) and triphenylphosphine (Aldrich, 522 mg, 2 mmol) at ambient temperature for two days. The reaction mixture was concentrated. The title product was purified by chromatography (SiO$_2$, CH$_2$Cl$_2$:MeOH:NH$_3$.H$_2$O, 90:10:1, R$_f$ 0.20) as a solid (200 mg, yield, 62%). $^1$H NMR (MeOH-d$_4$, 300 MHz) δ 1.45-1.57 (m, 1H), 1.63-1.91 (m, 2H), 1.97-2.12 (m, 1H), 2.17-2.24 (m, 1H), 2.66-3.00 (m, 5H), 3.30-3.41 (m, 1H), 4.56-4.64 (m, 1H), 7.05 (dt, J=8.8, 2.6 Hz, 2H), 7.68 (dt, J=9.2, 2.6 Hz, 2H), 7.82 (dt, J=8.8, 2.7 Hz, 2H), 8.28 (dt, J=8.8, 2.8 Hz, 2H) ppm. MS (DCl/NH$_3$) m/z 325 (M+H)$^+$.

Example 5B

3-[(4'-nitro-1,1'-biphenyl-4-yl)oxy]quinuclidine hemifumarate

The product of Example 5A (33 mg, 0.1 mmol) in ethyl acetate/ethanol (3 mL, 1:1) was treated with fumaric acid (12 mg, 0.1 mmol) at ambient temperature for 10 hours. The title compound was obtained as a solid (14 mg, yield, 36%). $^1$H NMR (MeOH-d$_4$, 300 MHz) δ 1.70-1.83 (m, 1H), 1.85-2.09 (m, 2H), 2.17-2.30 (m, 1H), 2.39-2.47 (m, 1H), 3.06-3.35 (m, 5H), 3.60-3.72 (m, 1H), 6.67 (s, 1H), 7.09 (dt, J=8.8, 2.5 Hz, 2H), 7.70 (dt, J=9.2, 2.3 Hz, 2H), 7.83 (dt, J=8.8, 2.4 Hz, 2H), 8.29 (dt, J=8.8, 2.3 Hz, 2H) ppm. MS (Cl/NH$_3$): m/z 325 (M+H)$^+$. Anal. Calculated for C$_{19}$H$_{20}$N$_2$O$_3$.0.5C$_4$H$_4$O$_4$.0.35H$_2$O: C, 64.89; H, 5.89; N, 7.21. Found: C, 64.82; H, 6.02; N, 6.95.

Example 5C

4'-(1-azabicyclo[2.2.2]oct-3-yloxy)-1,1'-biphenyl-4-amine

The product of Example 5A (150 mg, 0.46 mmol) in methanol (5 mL) was treated with Pd/C (Aldrich, wt. 10%, 20 mg) at ambient temperature for 30 minutes. The mixture was filtered and the filtrate was concentrated under reduced pressure to provide the title compound (89 mg, yield, 65%). $^1$H NMR (MeOH-d$_4$, 300 MHz) δ 1.44-1.58 (m, 1H), 1.63-1.89 (m, 2H), 1.99-2.13 (m, 1H), 2.15-2.23 (m, 1H), 2.72-3.04 (m, 5H), 3.29-3.39 (m, 1H), 4.50-4.58 (m, 1H), 6.77 (dt, J=8.8, 2.5 Hz, 2H), 6.91 (dt, J=8.8, 2.4 Hz, 2H), 7.32 (dt, J=8.5, 2.5 Hz, 2H), 7.43 (dt, J=9.2, 2.8 Hz, 2H) ppm. MS (DCl/NH$_3$) m/z 295 (M+H)$^+$.

Example 5D

4'-(1-azabicyclo[2.2.2]oct-3-yloxy)-1,1'-biphenyl-4-amine hemifumarate

The product of Example 5C (89 mg, 0.30 mmol) in ethyl acetate/ethanol (4.0 mL, 1:1) was treated with fumaric acid (35 mg, 0.30 mmol) at ambient temperature for 10 hours.

The title compound was obtained as a solid (67 mg, yield, 62%). $^1$H NMR (MeOH-d$_4$, 300 MHz) δ 1.70-1.83 (m, 1H), 1.85-2.09 (m, 2H), 2.18-2.32 (m, 1H), 2.38-2.45 (m, 1H), 3.12-3.38 (m, 5H), 3.60-3.71 (m, 1H), 4.74-4.81 (m, 1H), 6.68 (s, 1H), 6.77 (dt, J=8.8, 2.3 Hz, 2H), 6.97 (dt, J=8.8, 2.5 Hz, 2H), 7.32 (dt, J=8.5, 2.4 Hz, 2H), 7.47 (dt, J=8.8, 2.7 Hz, 2H) ppm. MS (DCl/NH$_3$): m/z 295 (M+H)$^+$. Anal. Calculated for C$_{19}$H$_{22}$N$_2$O.0.5C$_4$H$_4$O$_4$.0.3H$_2$O: C, 70.49; H, 6.93; N, 7.83. Found: C, 70.29; H, 6.88; N, 7.76.

Example 6

4'-[(3R)-1-azabicyclo[2.2.2]oct-3-yloxy]-1,1'-biphenyl-4-amine

Example 6A (3R)-1-azabicyclo[2.2.2]oct-3-yl benzoate (L)-tartrate (+/−)-1-azabicyclo[2.2.2]oct-3-yl benzoate (Sigma, 17.9 g, 77.5 mmol) in ethanol (80%, 222 mL) was treated with (L)-tartaric acid (Aldrich, 99% ee, 11.63 g, 77.5 mmol) at ambient temperature for 1 week. The mixture was filtered and the filter cake dried under reduced pressure to provide the title compound (6.5 g). in ~80% enantiomeric excess as determined by HPLC chiralpak AD column 25 cm×4 mm ID; ethanol:hexanes, 15:85; flow rate, 1 mL/minute; uv, 220 nm; Retention time: 13.3 minutes. The title compound was recrystallized from ethanol to provide the title compound in >98% enantiomeric excess. MS (DCl/NH$_3$) m/z 232 (M+H)$^+$.

Example 6B (3R)-quinuclidin-3-ol

The product of Example 6A (4.5 g, 11.8 mmol) in methanol (40 mL) was treated with NaOH (15%, 40 mL) at 50° C. for 10 hours. The methanol was removed under reduced pressure and the residue was extracted with chloroform (4×80 mL). The extracts were combined, dried over MgSO$_4$, dried, filtered, and the filtrate was concentrated to give the title product as a white solid (1.35 g, yield, 90%). MS (DCl/NH$_3$) m/z 128 (M+H)$^+$.

Example 6C (3S)-1-azabicyclo[2.2.2]oct-3-yl benzoate (D)-tartrate

The mother liquid of Example 6A was combined and concentrated under reduced pressure. The residue was treated with NaOH (1 N, 50 mL) at room temperature for 30 minutes and extracted with chloroform (3×mL) The extracts were combined, dried (MgSO$_4$), filtered, and the filtrate was concentrated to give crude 1-azabicyclo[2.2.2]oct-3-yl benzoate (15.25 g, 66 mmol). The crude in ethanol (80%, 190 ml) was treated with (D)-tartaric acid (Aldrich, 97% ee, 9.9 g, 66 mmol) at room temperature for 3 days according to the procedure of Example 1A to provide the title compound in 92.3% enantiomeric excess (7.0 g, yield, 28%).

Example 6D (3S)-quinuclidin-3-ol

The product of Example 6C (7.0 g, 18.4 mmol) was treated with NaOH (aqueous) according to the procedure of Example 1B. The title product was obtained as white a solid (2.0 g, yield, 86%). MS (DCl/NH$_3$) m/z 128 (M+H)$^+$.

Example 6E (3R)-3-[(4'-nitro-1,1'-biphenyl-4-yl)oxy]quinuclidine

The product of Example 6D (254 mg, 2 mmol) was treated with 4'-nitro-1,1'-biphenyl-4-ol (TCl, 215 mg, 1 mmol) according to the procedure of Example 5A. The title product was purified by chromatography (SiO$_2$, CH$_2$Cl$_2$: MeOH:NH$_3$.H$_2$O, 90:10:1, R$_f$, 0.20) as a solid (384 mg, yield, 59%). $^1$H NMR (MeOH-d$_4$, 300 MHz) δ 1.45-1.57 (m, 1H), 1.63-1.91 (m, 2H), 1.97-2.12 (m, 1H), 2.17-2.24 (m, 1H), 2.66-3.02 (m, 5H), 3.30-3.41 (m, 1H), 4.54-4.64 (m, 1H), 7.03 (dt, J=8.8, 2.6 Hz, 2H), 7.66 (dt, J=9.2, 2.6 Hz, 2H), 7.80 (dt, J=8.8, 2.7 Hz, 2H), 8.27 (dt, J=8.8, 2.8 Hz, 2H) ppm. MS (DCl/NH$_3$) m/z 325 (M+H)$^+$.

Example 6F

4'-[(3R)-1-azabicyclo[2.2.2]oct-3-yloxy]-1,1'-biphenyl-4-amine

The product of Example 6E (384 mg, 1.18 mmol) in methanol (5 mL) was treated with Pd/C (Aldrich, wt. 10%, 50 mg) under H$_2$ according to the procedure of Example 5C to provide the title compound (170 mg, yield, 49%). $^1$H NMR (MeOH-d$_4$, 300 MHz) δ 1.44-1.58 (m, 1H), 1.63-1.89 (m, 2H), 1.99-2.13 (m, 1H), 2.15-2.23 (m, 1H), 2.72-3.04 (m, 5H), 3.29-3.39 (m, 1H), 4.48-4.56 (m, 1H), 6.76 (dt, J=8.8, 2.5 Hz, 2H), 6.91 (dt, J=8.8, 2.4 Hz, 2H), 7.31 (dt, J=8.5, 2.5 Hz, 2H), 7.43 (dt, J=9.2, 2.8 Hz, 2H) ppm. MS (DCl/NH$_3$) m/z 295 (M+H)$^+$.

Example 6G

4'-[(3R)-1-azabicyclo[2.2.2]oct-3-yloxy]-1,1'-biphenyl-4-amine hemifumarate

The product of Example 6F (170 mg, 0.58 mmol) in ethyl acetate/ethanol (5.0 mL, 1:1) was treated with fumaric acid (70 mg, 0.60 mmol) at ambient temperature for 10 hours. The title compound was obtained as a solid (183 mg, yield, 48%). $^1$H NMR (MeOH-d$_4$, 300 MHz) δ 1.79-2.19 (m, 3H), 2.27-2.41 (m, 1H), 2.48-2.56 (m, 1H), 3.22-3.47 (m, 6H), 3.72-3.84 (m, 1H), 6.72 (s, 3.6H), 6.77 (dt, J=8.8, 2.3 Hz, 2H), 6.97 (dt, J=8.8, 2.5 Hz, 2H), 7.32 (dt, J=8.5, 2.4 Hz, 2H), 7.48 (dt, J=8.8, 2.7 Hz, 2H) ppm. MS (DCl/NH$_3$): m/z 295 (M+H)$^+$. Anal. Calculated for C$_{19}$H$_{22}$N$_2$O.1.8C$_4$H$_4$O$_4$: C, 62.52; H, 5.85; N, 5.57. Found: C, 62.53; H, 5.65; N, 5.69.

Example 7

4'-[(3S)-1-azabicyclo[2.2.2]oct-3-yloxy]-1,1'-biphenyl-4-amine

Example 7A (3S)-3-[(4'-nitro-1,1'-biphenyl-4-yl)oxy]quinuclidine

The product of Example 6B (508 mg, 4 mmol) was treated with 4'-nitro-biphenyl-4-ol (TCI, 430 mg, 2 mmol) according to the procedure of Example 5A. The title product was purified by chromatography (SiO$_2$, CH$_2$Cl$_2$:MeOH:NH$_3$.H$_2$O, 90:10:1, R$_f$, 0.20) as a solid (480 mg, yield, 74%). $^1$H NMR (MeOH-d$_4$, 300 MHz) δ 1.45-1.57 (m, 1H), 1.63-1.91 (m, 2H), 1.97-2.12 (m, 1H), 2.17-2.24 (m, 1H), 2.66-3.00 (m, 5H), 3.31-3.43 (m, 1H), 4.56-4.64 (m, 1H), 7.04 (dt, J=8.8, 2.6 Hz, 2H), 7.67 (dt, J=9.2, 2.6 Hz, 2H), 7.82 (dt, J=8.8, 2.7 Hz, 2H), 8.28 (dt, J=8.8, 2.8 Hz, 2H) ppm. MS (DCl/NH$_3$) m/z 325 (M+H)$^+$.

Example 7B

4'-(3-(S)-1-Aza-bicyclo[2.2.2]oct-3-yloxy)-biphenyl-4-ylamine

The product of Example 7A (480 mg, 1.48 mmol) in methanol (5 mL) was treated with Pd/C (Aldrich, wt. 10%, 50 mg) at ambient temperature for 30 minutes. The reaction mixture was filtered through a short column of diatomaceous earth and the filtrate was concentrated under reduced pressure to provide the title compound (350 mg, yield, 80%). $^1$H NMR (MeOH-d$_4$, 300 MHz) δ 1.44-1.58 (m, 1H), 1.63-1.89 (m, 2H), 1.99-2.13 (m, 1H), 2.15-2.23 (m, 1H), 2.72-3.04 (m, 5H), 3.58-3.68 (m, 1H), 4.50-4.58 (m, 1H), 6.76 (dt, J=8.8, 2.5 Hz, 2H), 6.91 (dt, J=8.8, 2.4 Hz, 2H), 7.31 (dt, J=8.5, 2.5 Hz, 2H), 7.43 (dt, J=9.2, 2.8 Hz, 2H) ppm. MS (DCl/NH$_3$) m/z 295 (M+H)$^+$.

Example 7C

4'-(3-(S)-1-Aza-bicyclo[2.2.2]oct-3-yloxy)-biphenyl-4-ylamine hemifumarate

The product of Example 7B (350 mg, 1.19 mmol) in ethyl acetate/ethanol (5.0 mL, 1:1) was treated with fumaric acid (140 mg, 1.20 mmol) at ambient temperature for 10 hours. The title compound was obtained as a solid (376 mg, yield, 89%). $^1$H NMR (MeOH-d$_4$, 300 MHz) δ 1.68-1.81 (m, 1H), 1.84-2.07 (m, 2H), 2.16-2.31 (m, 1H), 2.36-2.44 (m, 1H), 3.09-3.39 (m, 5H), 3.58-3.68 (m, 1H), 4.72-4.79 (m, 1H), 6.67 (s, 1H), 6.76 (dt, J=8.8, 2.3 Hz, 2H), 6.96 (dt, J=8.8, 2.5 Hz, 2H), 7.32 (dt, J=8.5, 2.4 Hz, 2H), 7.46 (dt, J=8.8, 2.7 Hz, 2H) ppm. MS (DCl/NH$_3$): m/z 295 (M+H)$^+$. Anal. Calculated for C$_{19}$H$_{22}$N$_2$O.1.8C$_4$H$_4$O$_4$:C$_{19}$H$_{22}$N$_2$O.0.55C$_4$H$_4$O$_4$: C, 71.08; H, 6.81; N, 7.82. Found: C, 71.07; H, 6.82; N, 7.60.

Example 8

N-[4'-(1-azabicyclo[2.2.2]oct-3-yloxy)-1,1'-biphenyl-4-yl]-N-methylamine

Example 8A

3-[(4'-iodo-1,1'-biphenyl-4-yl)oxy]quinuclidine

3-Hydroxy quinuclidine (Aldrich, 508 mg, 4 mmol) was coupled with 4'-iodo-1,1'-biphenyl-4-ol (Avacado, 592 mg, 2 mmol) according to the procedure of Example 5A. The title product was purified by chromatography (SiO$_2$, CH$_2$Cl$_2$:MeOH:NH$_3$.H$_2$O, 90:10:1, R$_f$, 0.30) as solid (480 mg, yield, 59%). $^1$H NMR (MeOH-d$_4$, 300 MHz) δ 1.43-1.57 (m, 1H), 1.62-1.88 (m, 2H), 1.97-2.12 (m, 1H), 2.14-2.21 (m, 1H), 2.72-3.00 (m, 5H), 3.31-3.43 (m, 1H), 4.51-4.60 (m, 1H), 6.98 (d, J=8.8 Hz, 2H), 7.35 (d, J=8.5 Hz, 2H), 7.53 (d, J=8.8 Hz, 2H), 7.74 (d, J=8.5 Hz, 2H) ppm. MS (DCl/NH$_3$) m/z 406 (M+H)$^+$.

Example 8B

N-[4'-(1-azabicyclo[2.2.2]oct-3-yloxy)-1,1'-biphenyl-4-yl]-N-benzyl-N-methylamine The product of Example 8A (405 mg, 1 mmol) in toluene (5 mL) was treated with benzyl(methyl)amine (Aldrich, 146 mg, 1.2 mmol), Pd$_2$(dba)$_3$ (Strem Chemicals, 24 mg, 0.025 mmol), ($^t$Bu$_3$P)$_2$Pd (Strem Chemicals, 26 mg, 0.05 mmol), $^t$BuONa (Aldrich, 105 mg 1.1 mmol) and heated at 110° C. under N$_2$ for 15 hours. The reaction mixture was allowed to cool to room temperature, diluted with ethyl acetate (20 mL), and washed with brine (2×5 mL). The organic phase was concentrated and the title compound was purified by chromatography (SiO$_2$, CH$_2$Cl$_2$:MeOH:NH$_3$.H$_2$O, 90:10:2, R$_f$, 0.35) as a solid (200 mg, yield, 50%). $^1$H NMR (MeOH-d$_4$, 300 MHz) showed a mixture of the title compound and 3-(biphenyl-4-yloxy)-1-aza-bicyclo[2.2.2]octane as solid (200 mg). MS (DCl/NH$_3$) m/z 399 (M+H)$^+$.

Example 8C

N-[4'-(1-azabicyclo[2.2.2]oct-3-yloxy)-1,1'-biphenyl-4-yl]-N-methylamine

The product of Example 8B (200 mg, 0.50 mmol) in methanol (10 mL) was treated with Pd/C (Aldrich, 10% wt., 50 mg) at 60° C. under H$_2$ for 10 hours. The mixture was allowed to cool to room temperature and was filtered through a short column of diatomaceous earth. The filtrate was concentrated under reduced pressure to provide the title compound (20 mg, yield, 13%). $^1$H NMR (MeOH-d$_4$, 300 MHz) δ 1.43-1.56 (m, 1H), 1.62-1.88 (m, 2H), 1.99-2.12 (m, 1H), 2.14-2.21 (m, 1H), 2.79 (s, 3H) 2.90-3.03 (m, 5H), 3.27-3.38 (m, 1H), 4.49-4.56 (m, 1H), 6.67 (d, J=8.8, 2.7 Hz, 2H), 6.91 (d, J=8.8, 2.9 Hz, 2H), 7.35 (d, J=8.8, 2.7 Hz, 2H), 7.43 (d, J=9.2, 2.7 Hz, 2H) ppm. MS (DCl/NH$_3$): m/z 309 (M+H)$^+$.

Example 8D

N-[4'-(1-azabicyclo[2.2.2]oct-3-yloxy)-1,1'-biphenyl-4-yl]-N-methylamine hydrochloride The product of Example 8C (20 mg, 0.07 mmol) in ethyl acetate (4 mL) was treated with 4M HCl in 1,4-dioxane (0.5 mL, 2 mmol) at ambient temperature for 10 hours. The title compound was obtained as a solid (17 mg, yield, 55%). $^1$H NMR (300 MHz, MeOH-$d_4$) δ 1.84-2.21 (m, 3H), 2.25-2.40 (m, 1H), 2.51-2.59 (m, 1H), 3.09 (s, 3H), 3.18-3.48 (m, 5H), 3.79-3.89 (m, 1H), 4.91-4.98 (m, 1H), 7.09 (d, J=8.8 Hz, 2H), 7.48 (d, J=8.8 Hz, 2H), 7.63 (d, J=8.8 Hz, 2H), 7.76 (d, J=8.8 Hz, 2H) ppm. MS (DCl/NH$_3$): m/z 309 (M+H)$^+$.

Example 9

N-{4'-[(3R)-1-azabicyclo[2.2.2]oct-3-yloxy]-1,1'-biphenyl-4-yl}-N,N-dimethylamine

Example 9A (R)-3-Quinuclidinol (R)-3-Quinuclidinol hydrochloride (Aldrich, 20 g, 12.2 mmol) was treated with NaOH aqueous solution (20%, 50 mL) at ambient temperature for 10 minutes and extracted with CHCO$_3$/isopropyl alcohol (10:1, 3×200 mL). The extracts were combine, washed with brine (50 mL), dried over MgSO$_4$, filtered, and the filtrate was concentrated under reduced pressure to give the title compound as a white solid (15. 5 g, yield, 99%). $^1$H NMR (300 MHz, MeOH-$d_4$) δ 1.36-1.50 (m, 1H), 1.52-1.60 (m, 1H), 1.76-1.85 (m, 2H), 1.90-2.05 (m, 1H), 2.50-2.95 (m, 5H), 3.10 (ddd, J=14.2, 8.4, 2.3 Hz, 1H), 3.82-3.88 (m, 1H) ppm. MS (DCl/NH$_3$): m/z 128 (M+H)$^+$.

Example 9B (3R)-3-(4-bromophenoxy)quinuclidine

The product of Example 9A (1.27 g, 10 mmol) was treated with 4-bromophenol (Aldrich, 2.83 g, 10 mol) according to the procedure of Example 1A. The title product was purified by chromatography (SiO$_2$, CH$_2$Cl$_2$:MeOH:NH$_3$.H$_2$O, 90:10:1, R$_f$ 0.30) as solid (400 mg, yield, 14%). $^1$H NMR (300 MHz, MeOH-$d_4$) δ 1.41-1.54 (m, 1H), 1.59-1.73 (m, 1H), 1.73-1.86 (m, 1H), 1.92-2.06 (m, 1H), 2.09-2.17 (m, 1H), 2.71-2.97 (m, 5H), 3.24-3.34 (m, 1H), 4.45-4.52 (m, 1H), 6.83 (dt, J=9.2, 2.6 Hz, 2H), 7.37 (dt, J=9.2, 2.7 Hz, 2H) ppm. MS (DCl/NH$_3$): m/z 282 (M+H)$^+$, 284 (M+H)$^+$.

Example 9C

N-{4'-[(3R)-1-azabicyclo[2.2.2]oct-3-yloxy]-1,1'-biphenyl-4-yl}-N,N-dimethylamine The product of Example 9B (282 mg, 1 mmol) was treated with N,N-dimethyl-4-amino-phenyl boronic acid (230 mg, 1.4 mmol) according to the procedure of Example 1B. The title product was purified by chromatography (SiO$_2$, CH$_2$Cl$_2$:MeOH:NH$_3$.H$_2$O, 90:10:1, R$_f$ 0.2) as a solid (118 mg, yield, 37%). $^1$H NMR (MeOH-$d_4$, 300 MHz) δ 1.41-1.56 (m, 1H), 1.61-1.88 (m, 2H), 1.98-2.12 (m, 1H), 2.14-2.22 (m, 1H), 2.72-3.01 (m, 11H), 3.22-3.34 (m, 1H), 4.48-4.57 (m, 1H), 6.83 (dt, J=8.8, 3.0 Hz, 2H), 6.92 (dt, J=8.8, 2.1 Hz, 2H), 7.39-7.49 (m, 4H) ppm. MS (DCl/NH$_3$) m/z 323 (M+H)$^+$.

Example 9C

N-[4'-[(3R)-1-azabicyclo[2.2.2]oct-3-yloxy]-1,1'-biphenyl-4-yl)-N,N-dimethylamine fumarate The product of Example 9B (118 mg, 0.37 mmol) in ethyl acetate:ethanol (5 mL, 1:1). was treated with fumaric acid (46 mg, 0.4 mmol). The title compound was obtained as a solid (128.8 mg, yield, 79%). $^1$H NMR (MeOH-$d_4$, 300 MHz) δ 1.41-2.15 (m, 3H), 2.24-2.37 (m, 1H), 2.44-2.52 (m, 1H), 2.95 (s, 6H), 3.16-3.43 (m, 6H), 3.68-3.79 (m, 1H), 6.68 (s, 2H), 6.83 (dt, J=9.2, 3.0 Hz, 2H), 6.99 (dt, J=8.8, 3.0 Hz, 2H), 7.43 (dt, J=8.8, 3.0 Hz, 2H), 7.50 (dt, J=8.5, 3.0 Hz, 2H) ppm. MS (DCl/NH$_3$) m/z 323 (M+H)$^+$. Anal. Calculated for C$_{21}$H$_{26}$N$_2$O.1.0C$_4$H$_4$O$_4$.0.1 ethyl acetate: C, 68.20; H, 6.94; N, 6.26. Found: C, 68.00; H, 7.15; N, 6.25.

Example 10

N-[4'-(1-azabicyclo[2.2.2]oct-3-yloxy)-1,1'-biphenyl-4-yl]methanesulfonamide

Example 10A

N-[4'-(1-azabicyclo[2.2.2]oct-3-yloxy)-1,1'-biphenyl-4-yl]methanesulfonamide

The product of Example 5C (148 mg, 0.5 mmol) was treated with methansulfonyl chloride (Aldrich, 68 mg, 0.6 mmol) and triethyl amine (303 mg, 3 mmol) in CH$_2$Cl$_2$ (5 ml) at 0° C. to room temperature for 3 h. The mixture was allowed to warm to room temperature and was concentrated under reduced pressure. The title product was purified by chromatography (SiO$_2$, CH$_2$Cl$_2$:MeOH:NH$_3$.H$_2$O, 90:10:1, R$_f$. 0.3) as oil (20 mg, yield, 11%). $^1$H NMR (MeOH-$d_4$, 300 MHz) δ 1.59-1.73 (m, 1H), 1.75-2.01 (m, 2H), 2.10-2.24 (m, 1H), 2.29-2.36 (m, 1H), 2.69 (s, 3H), 2.94-3.22 (m, 5H), 3.48-3.59 (m, 1H), 4.67-4.74 (m, 1H), 7.00 (d, J=8.8 Hz, 2H), 7.30 (d, J=8.5 Hz, 2H), 7.52-7.58 (m, 4H) ppm. MS (DCl/NH$_3$) m/z 373 (M+H)$^+$.

Example 10B

N-[4'-(1-azabicyclol2.2.2]oct-3-yloxy)-1.1'-biphenyl-4-yl]methanesulfonamide fumarate The product of Example 10A (20 mg, 0.05 mmol) in ethyl acetate/ethanol (3 mL, 1:1) was treated with fumaric acid (11 mg, 0.1 mmol) at ambient temperature for 10 hours. The title compound was obtained as a solid (16 mg, yield, 54%). $^1$H NMR (MeOH-$d_4$, 300 MHz) δ 1.78-2.16 (m, 3H), 2.23-2.37 (m, 1H), 2.46-2.53 (m, 1H), 2.97 (s, 3H), 3.16-3.43 (m, 5H), 3.70-3.81 (m, 1H), 6.68 (s, 2H), 7.04 (d, J=8.8 Hz, 2H), 7.31 (d, J=8.5 Hz, 2H), 7.53-7.60 (m, 4H) ppm. MS (DCl/NH$_3$) m/z 373 (M+H)$^+$. Anal. Calculated for C$_{20}$H$_{24}$N$_2$O$_3$S.1.4C$_4$H$_4$O$_4$.0.1 ethyl acetate: C, 57.43; H, 5.63; N, 5.15. Found: C, 57.10; H, 5.71; N, 5.26.

Example 11

N-[4'-(1-azabicyclo[2.2.2]oct-3-yloxy)-1,1'-biphenyl-4-yl]-N-phenylamine

Example 11A

N-[4'-(1-azabicyclo[2.2.2]oct-3-yloxy)-1,1'-biphenyl-4-yl]-N-phenylamine

The product of Example 8A (405 mg, 1 mmol) was treated with aniline (110 mg, 1.2 mmol) according to the procedure in Example 8B. The title compound was purified by chromatography (SiO$_2$, CH$_2$Cl$_2$:MeOH:NH$_3$.H$_2$O, 90:10:1, R$_f$, 0.25) as solid (200 mg, yield, 54%). $^1$H NMR (MeOH-d$_4$, 300 MHz) δ 1.42-1.56 (m, 1H), 1.62-1.88 (m, 2H), 1.99-2.12 (m, 1H), 2.14-2.22 (m, 1H), 2.73-3.02 (m, 5H), 3.27-3.38 (m, 1H), 4.51-4.59 (m, 1H), 6.80-6.87 (m, 1H), 6.94 (d, J=8.8 Hz, 2H), 7.06-7.15 (m, 4H), 7.18-7.26 (m, 2H), 7.44 (d, J=8.5 Hz, 2H), 7.49 (d, J=8.8 Hz, 2H) ppm. MS (DCl/NH$_3$) m/z 371 (M+H)$^+$.

Example 11B

N-[4'-(1-azabicyclo[2.2.2]oct-3-yloxy)-1,1'-biphenyl-4-yl]-N-phenylamine fumarate The product of Example 11A (200 mg, 0.54 mmol) in ethyl acetate:ethanol (5 mL, 1:1) was treated with fumaric acid (70 mg, 0.6 mmol). The title compound was obtained as a solid (197.8 mg, yield, 72%). $^1$H NMR (MeOH-d$_4$, 300 MHz) δ 1.81-2.20 (m, 3H), 2.27-2.42 (m, 1H), 2.50-2.58 (m, 1H), 3.17-3.48 (m, 5H), 3.75-3.87 (m, 1H), 4.85-4.93 (m, 1H), 6.71 (s, 2.5H), 6.81-6.89 (m, 1H), 7.02 (d, J=8.8 Hz, 2H), 7.07-7.17 (m, 4H), 7.18-7.27 (m, 2H), 7.45 (d, J=8.8 Hz, 2H), 7.54 (d, J=8.8 Hz, 2H) ppm. MS (DCl/NH$_3$) m/z 371 (M+H)$^+$. Anal. Calculated for C$_{25}$H$_{26}$N$_2$O.1.2C$_4$H$_4$O$_4$: C, 70.21; H, 6.09; N, 5.50. Found: C, 70.09; H, 6.17; N, 5.43.

Example 12

3-[6-(1-azabicyclo[2.2.2]oct-3-yloxy)pyridin-3-yl]aniline

Example 12A

3-[(5-bromopyridin-2-yl)oxy]quinuclidine

3-Hydroxy quinuclidine (Aldrich, 3.2 g, 25 mmol) in DMF (anhydrous, 30 mL) was treated with NaH (Aldrich, 99%, 1.2 g, 50 mmol) at ambient temperature for 1 hour. The mixture was then treated with 2-chloro-5-bromopyridine (7.1 g, 30 mmol) and stirred at 100° C. for 6 hours. The mixture reaction was treated with Na$_2$CO$_3$ (2M, 10 mL) at 10° C. and extracted with ethyl acetate (2×50 mL). The extracts were combined and concentrated under reduced pressure. The title compound was purified by chromatography (SiO$_2$, CH$_2$Cl$_2$:MeOH:NH$_3$.H$_2$O, 90:10:2, R$_f$ 0.20) as oil (5.3 g, yield, 75%). $^1$H NMR (MeOH-d$_4$, 300 MHz) δ 1.46-1.58 (m, 1H), 1.60-1.88 (m, 2H), 1.96-2.10 (m, 1H), 2.24-2.30 (m, 1H), 2.72-2.98 (m, 5H), 3.42-3.46 (m, 1H), 5.00-5.08 (m, 1H), 6.75 (d, J=8.8 Hz, 1H), 7.77 (dd, J=8.9, 2.4 Hz, 1H), 8.16 (d, J=2.7 Hz, 1H) ppm. MS (DCl/NH$_3$) m/z 283 (M+H)$^+$, 285 (M+H)$^+$.

Example 12B

3-[6-(1-azabicyclo[2.2.2]oct-3-yloxy)pyridin-3-yl]aniline

The product of Example 12A (283 mg, 1 mmol) was treated with 3-amino-phenylboronic acid (Lancaster, 274 mg, 2.0 mmol) according to the procedure of Example 1B. The title compound was purified by chromatography (SiO$_2$, CH$_2$Cl$_2$:MeOH:NH$_3$.H$_2$O, 90:10:1, R$_f$ 0.10) as solid (180 mg, yield, 61%). $^1$H NMR (MeOH-d$_4$, 300 MHz) δ 1.42-1.56 (m, 1H), 1.62-1.88 (m, 2H), 1.99-2.12 (m, 1H), 2.16-2.28 (m, 1H), 2.73-3.04 (m, 5H), 3.40-3.50 (m, 1H), 5.01-5.10 (m, 1H), 6.70 (ddd, J=7.8, 2.7, 0.7 Hz, 1H), 6.84-6.94 (m, 3H), 7.16 (t, J=7.8 Hz, 1H), 7.88 (dd, J=8.5, 2.4 Hz, 1H), 8.29 (d, J=2.6 Hz, 1H) ppm. MS (DCl/NH$_3$) m/z 296 (M+H)$^+$.

Example 12C

3-[6-(1-azabicyclo[2.2.2]oct-3-yloxy)pyridin-3-yl]aniline hydrochloride

The product of Example 12B (50 mg, 0.17 mmol) in ethyl acetate (5 mL) was treated with 4M HCl in 1,4-dioxane (0.2 mL, 0.8 mmol) at ambient temperature for 10 hours. The title compound was obtained as a solid (30 mg, yield, 44%). $^1$H NMR (MeOH-d$_4$, 300 MHz) δ 1.90-2.25 (m, 3H), 2.30-2.45 (m, 1H), 2.70-2.76 (m, 1H), 3.37-3.52 (m, 5H), 3.90-3.98 (m, 1H), 5.42-5.50 (m, 1H), 6.71 (s, 2.5H), 6.81-6.89 (m, 1H), 7.03 (d, J=8.9 Hz, 1H), 7.41 (ddd, J=7.8, 2.4, 1.0 Hz, 1H), 7.60-7.68 (m, 2H), 7.75 (dt, J=7.8, 1.0 Hz, 1H), 8.05 (dd, J=8.8, 2.7 Hz, 1H), 8.45 (d, J=2.7 Hz, 1H) ppm. MS (DCl/NH$_3$) m/z 296 (M+H)$^+$. Anal. Calculated for C$_{18}$H$_{21}$N$_3$O.3.3HCl.1.0H$_2$O: C, 49.85; H, 6.11; N, 9.69. Found: C, 49.93; H, 5.77; N, 9.51.

Example 13

4-[5-(1-azabicyclo[2.2.2]oct-3-yloxy)pyrazin-2-yl]aniline

Example 13A benzyl 4-[5-(1-azabicyclo[2.2.2]oct-3-yloxy)pyrazin-2-yl]phenylcarbamate 3-Quinuclidinol (Aldrich, 610 mg, 4.8 mmol) was treated with benzyl 4-(5-hydroxypyrazin-2-yl)phenylcarbamate (Ref. EP146282, 1.28 g, 4 mmol) according to the procedure of Example 5A. The title product was purified by chromatography (SiO$_2$, CH$_2$Cl$_2$:MeOH:NH$_3$.H$_2$O, 90:10:1, R$_f$ 0.30) as solid (0.68 g, yield, 40%). $^1$H NMR (MeOH-d$_4$, 300 MHz) δ 1.47-1.62 (m, 1H), 1.65-1.92 (m, 2H), 1.97-2.14 (m, 1H), 2.22-2.28 (m, 1H), 2.74-3.05 (m, 5H), 3.33-3.46 (m, 1H), 5.10-5.18 (m, 1H), 5.20 (s, 2H), 7.30-7.46 (m, 5H), 7.56 (d, J=8.8 Hz, 2H), 7.88 (d, J=8.8 Hz, 2H), 8.24 (d, J=1.4 Hz, 1H), 8.55 (d, J=1.4 Hz, 1H) ppm. MS (DCl/NH$_3$) m/z 431 (M+H)$^+$.

Example 13B

4-[5-(1-azabicyclo[2.2.2]oct-3-yloxy)pyrazin-2-yl]aniline

The product of Example 13A (0.68 g, 1.58 mmol) in ethanol (20 mL) was treated with Pd/C (Aldrich, 10% wt., 70 mg) under H$_2$ at ambient temperature for 4 hours. The mixture was filtered through a short column of diatomaceous earth and the filtrate was concentrated to give the title product as a solid (400 mg, yield, 86%). $^1$H NMR (MeOH-d$_4$, 300 MHz) δ 1.47-1.62 (m, 1H), 1.64-1.90 (m, 2H), 1.97-2.12 (m, 1H), 2.19-2.27 (m, 1H), 2.73-3.03 (m, 5H), 3.34-3.44 (m, 1H), 5.07-5.14 (m, 1H), 6.78 (dt, J=8.8, 2.7 Hz, 2H), 7.68 (dt, J=8.5, 2.7 Hz, 2H), 8.17 (d, J=1.4 Hz, 1H), 8.45 (d, J=1.4 Hz, 1H) ppm. MS (DCl/NH$_3$) m/z 297 (M+H)$^+$.

Example 13C

4-[5-(1-azabicyclo[2.2.2]oct-3-yloxy)pyrazin-2-yl]aniline hemifumarate

The product of Example 13B (100 mg, 0.34 mmol) in ethyl acetate/ethanol (5 mL, 1:1) was treated with fumaric acid (47 mg, 0.4 mmol) at ambient temperature for 10 hours. The title compound was obtained as a solid (109 mg, yield, 91%). $^1$H NMR (MeOH-d$_4$, 300 MHz) δ 1.73-2.10 (m, 3H), 2.17-2.33 (m, 1H), 2.41-2.50 (m, 1H), 3.05-3.44 (m, 5H), 3.64-3.76 (m, 1H), 5.24-5.32 (m, 1H), 6.67 (s, 1H), 6.78 (dt, J=8.8, 2.7 Hz, 2H), 7.69 (dt, J=8.5, 2.7 Hz, 2H), 8.22 (d, J=1.4 Hz, 1H), 8.46 (d, J=1.4 Hz, 1H) ppm. MS (DCl/NH$_3$) m/z 297 (M+H)$^+$. Anal. Calculated for C$_{17}$H$_{20}$N$_4$O.0.5C$_4$H$_4$O$_4$: C, 64.39; H, 6.26; N, 15.81. Found: C, 64.09; H, 6.21; N, 15.64.

Example 14

4-{5-[(3R)-1-azabicyclo[2.2.2]oct-3-yloxy]pyrazin-2-yl}aniline

Example 14A benzyl 4-{5-[(3R)-1-azabicyclo[2.2.2]oct-3-yloxy]pyrazin-2-yl}phenylcarbamate The product of Example 6D (155 mg, 1.2 mmol) was treated with benzyl 4-(5-hydroxypyrazin-2-yl)phenylcarbamate (Ref. EP146282A, 321 mg, 1 mmol) according to the procedure of Example 5A. The title compound was purified by chromatography (SiO$_2$, CH$_2$Cl$_2$:MeOH:NH$_3$.H$_2$O, 90:10:1, R$_f$, 0.3) as a solid (180 mg, yield, 42%). $^1$H NMR (MeOH-d$_4$, 300 MHz) δ 1.47-1.62 (m, 1H), 1.64-1.90 (m, 2H), 1.98-2.12 (m, 1H), 2.20-2.28 (m, 1H), 2.74-3.04 (m, 5H), 3.34-3.46 (m, 1H), 5.10-5.17 (m, 1H), 5.20 (s, 2H), 7.27-7.47 (m, 5H), 7.56 (d, J=8.8 Hz, 2H), 7.88 (d, J=8.8 Hz, 2H), 8.24 (d, J=1.4 Hz, 1H), 8.55 (d, J=1.4 Hz, 1H) ppm. MS (DCl/NH$_3$) m/z 431 (M+H)$^+$.

Example 14B

4-{5-[(3R)-1-azabicyclo[2.2.2]oct-3-yloxy]pyrazin-2-yl}aniline

The product of Example 15A (180 mg, 0.42 mmol) was treated with Pd/C (Aldrich, 10% wt., 20 mg) in EtOH (10 mL) under H$_2$ according to the procedure of Example 13B. THe title compound was obtained as oil (125 mg, yield, 99%). $^1$H NMR (MeOH-d$_4$, 300 MHz) δ 1.47-1.62 (m, 1H), 1.64-1.90 (m, 2H), 1.97-2.12 (m, 1H), 2.19-2.27 (m, 1H), 2.73-3.03 (m, 5H), 3.34-3.44 (m, 1H), 5.07-5.14 (m, 1H), 6.78 (dt, J=8.8, 2.7 Hz, 2H), 7.68 (dt, J=8.5, 2.7 Hz, 2H), 8.17 (d, J=1.4 Hz, 1H), 8.45 (d, J=1.4 Hz, 1H) ppm. MS (DCl/NH$_3$) m/z 297 (M+H)$^+$.

Example 14C

4-[5-[(3R)-1-azabicyclo[2.2.2]oct-3-yloxy]pyrazin-2-yl]aniline hemifumarate The product of Example 14B (125 mg, 0.42 mmol) was treated with fumaric acid (50 mg, 0.42 mmol) in ethyl acetate/EtOH (v. 1:1, 5 mL) at ambient temperature for 10 h. The title compound was obtained as solid (124.4 mg, yield, 81%). $^1$H NMR (MeOH-d$_4$, 300 MHz) δ 1.73-2.10 (m, 3H), 2.17-2.33 (m, 1H), 2.41-2.50 (m, 1H), 3.05-3.44 (m, 5H), 3.64-3.76 (m, 1H), 5.24-5.32 (m, 1H), 6.67 (s, 1H), 6.78 (dt, J=8.8, 2.7 Hz, 2H), 7.69 (dt, J=8.5, 2.7 Hz, 2H), 8.22 (d, J=1.4 Hz, 1H), 8.46 (d, J=1.4 Hz, 1H) ppm. MS (DCl/NH$_3$) m/z 297 (M+H)$^+$. Anal. Calculated for C$_{17}$H$_{20}$N$_4$O.0.6C$_4$H$_4$O$_4$: C, 63.66; H, 6.17; N, 15.31. Found: C, 63.80; H, 6.23; N, 15.49.

Example 15

4-{5-[(3S)-1-azabicyclo[2.2.2]oct-3-yloxy]pyrazin-2-yl}aniline

Example 15A

Benzyl{4-[5-(3-(S)-1-Aza-bicyclo[2.2.2]oct-3-yloxy)-pyrazin-2-yl]-phenyl}-carbamate The product of Example 9A (155 mg, 1.2 mmol) was treated with benzyl 4-(5-hydroxypyrazin-2-yl)phenylcarbamate (Ref. EP146282A, 321 mg, 1 mmol) according to the procedure of Example 5A. The title compound was purified by chromatography (SiO$_2$, CH$_2$Cl$_2$:MeOH:NH$_3$.H$_2$O, 90:10:1, R$_f$, 0.3) as solid (170 mg, yield, 40%). $^1$H NMR (MeOH-d$_4$, 300 MHz) δ 1.47-1.62 (m, 1H), 1.64-1.90 (m, 2H), 1.98-2.12 (m, 1H), 2.20-2.28 (m, 1H), 2.74-3.04 (m, 5H), 3.34-3.46 (m, 1H), 5.10-5.17 (m, 1H), 5.20 (s, 2H), 7.27-7.47 (m, 5H), 7.56 (d, J=8.8 Hz, 2H), 7.88 (d, J=8.8 Hz, 2H), 8.24 (d, J=1.4 Hz, 1H), 8.55 (d, J=1.4 Hz, 1H) ppm. MS (DCl/NH$_3$) m/z 431 (M+H)$^+$.

Example 15B

4-{5-[(3S)-1-azabicyclo[2.2.2]oct-3-yloxy]pyrazin-2-yl}aniline

The product of Example 15A (170 mg, 0.40 mmol) in ethanol (10 mL) was treated with Pd/C (Aldrich, 10% wt., 20 mg) under H$_2$ according to the procedure of Example 13B. The title compound was obtained as an oil (120 mg, yield, 99%). $^1$H NMR (MeOH-d$_4$, 300 MHz) δ 1.45-1.60 (m, 1H), 1.63-1.90 (m, 2H), 1.97-2.12 (m, 1H), 2.19-2.26 (m, 1H), 2.73-3.03 (m, 5H), 3.34-3.44 (m, 1H), 5.07-5.14 (m, 1H), 6.78 (dt, J=8.8, 2.7 Hz, 2H), 7.68 (dt, J=8.5, 2.7 Hz, 2H), 8.17 (d, J=1.4 Hz, 1H), 8.45 (d, J=1.4 Hz, 1H) ppm. MS (DCl/NH$_3$) m/z 297 (M+H)$^+$.

Example 15C

4-{5-[(3S)-1-azabicyclo[2.2.2]oct-3-yloxy]pyrazin-2-yl}aniline hemifumarate The product of Example 15B (120 mg, 0.42 mmol) in ethyl acetate/ethanol (5 mL, 1:1) was treated with fumaric acid (50 mg, 0.42 mmol) at ambient temperature for 10 hours. The title compound was obtained as solid (106 mg, yield, 73%). $^1$H NMR (MeOH-d$_4$, 300 MHz) δ 1.73-2.10

(m, 3H), 2.17-2.33 (m, 1H), 2.41-2.50 (m, 1H), 3.09-3.40 (m, 5H), 3.66-3.77 (m, 1H), 5.24-5.32 (m, 1H), 6.67 (s, 1H), 6.78 (dt, J=8.8, 2.7 Hz, 2H), 7.69 (dt, J=8.5, 2.7 Hz, 2H), 8.23 (d, J=1.4 Hz, 1H), 8.47 (d, J=1.4 Hz, 1H) ppm. MS (DCl/NH$_3$) m/z 297 (M+H)$^+$. Anal. Calculated for C$_{17}$H$_{20}$N$_4$O.0.58C$_4$H$_4$O$_4$: C, 63.80; H, 6.19; N, 15.40. Found: C, 63.83; H, 5.97; N, 15.50.

Example 16

N-{4-[5-(1-azabicyclo[2.2.2]oct-3-yloxy)pyrazin-2-yl]phenyl}-N,N-dimethylamine

Example 16A

N-{4-[5-(1-azabicyclo[2.2.2]oct-3-yloxy)pyrazin-2-yl]phenyl}-N,N-dimethylamine

The product of Example 13B (160 mg, 0.54 mmol) in acetonitrile (5 mL) was treated with formaldehyde (Aldrich, 37%, 1 mL, 12 mmol) and NaBH(OAc)$_3$ (Aldrich, 343 mg, 1.62 mmol) at ambient temperature for 6 hours. The mxiture treated with aqueous Na$_2$CO$_3$ (saturated 5 mL) and extracted with ethyl acetate (3×10 mL). The extracts were combined and concentrated under reduced pressure. The title compound was purified by chromatography (SiO$_2$, CH$_2$Cl$_2$:MeOH:NH$_3$.H$_2$O, 90:10:1, R$_f$ 0.20) as a solid (130 mg, yield, 74%). $^1$H NMR (MeOH-d$_4$, 300 MHz) δ 1.47-1.61 (m, 1H), 1.64-1.90 (m, 2H), 1.98-2.11 (m, 1H), 2.18-2.27 (m, 1H), 2.73-3.04 (m, 11H), 3.33-3.45 (m, 1H), 5.07-5.15 (m, 1H), 6.83 (d, J=8.8 Hz, 2H), 7.78 (d, J=8.8 Hz, 2H), 8.18 (d, J=1.4 Hz, 1H), 8.47 (d, J=1.4 Hz, 1H) ppm. MS (DCl/NH$_3$) m/z 325 (M+H)$^+$.

Example 16B

N-{4-[5-(1-azabicyclo[2.2.2]oct-3-yloxy)pyrazin-2-yl]phenyl}-N,N-dimethylamine hemifumarate The product of Example 16A (130 mg, 0.40 mmol) in ethyl acetate/ethanol (5 mL, 1:1) was treated with fumaric acid (47 mg, 0.4 mmol) at ambient temperature for 10 hours. The title compound was obtained as a solid (101 mg, yield, 63%). $^1$H NMR (MeOH-d$_4$, 300 MHz) δ 1.74-2.11 (m, 3H), 2.18-2.34 (m, 1H), 2.43-2.51 (m, 1H), 3.00 (s, 6H), 3.08-3.37 (m, 5H), 3.65-3.79 (m, 1H), 5.24-5.33 (m, 1H), 6.67 (s, 1.2H), 6.84 (d, J=8.8 Hz, 2H), 7.80 (d, J=9.2 Hz, 2H), 8.23 (d, J=1.4 Hz, 1H), 8.50 (d, J=1.4 Hz, 1H) ppm. MS (DCl/NH$_3$) m/z 325 (M+H)$^+$. Anal. Calculated for C$_{19}$H$_{24}$N$_4$O.0.6C$_4$H$_4$O$_4$.0.3H$_2$O: C, 64.34; H, 6.81; N, 14.03. Found: C, 64.45; H, 7.02; N, 13.86.

Example 17

N-{4-[5-(1-azabicyclo[2.2.2]oct-3-yloxy)pyrazin-2-yl]phenyl}acetamide

Example 17A

N-{4-[5-(1-azabicyclo[2.2.2]oct-3-yloxy)pyrazin-2-yl]phenyl}acetamide

The product of Example 13B (60 mg, 0.2 mmol) in dichloromethane (2 mL) was treated with acetic anhydride (Aldrich, 0.06 mL, 0.5 mmol) and triethyl amine (Aldrich, 0.25 mL, 1.8 mmol) at 0° C. to room temperature for 4 hours. The mixture was treated with aqueous Na$_2$CO$_3$ (2M, 5 mL) and extracted with ethyl acetate (3×15 mL). The extracts were combined and concentrated under reduced pressure. The title product was purified by chromatography (SiO$_2$, CH$_2$Cl$_2$:MeOH:NH$_3$.H$_2$O, 90:10:1, R$_f$ 0.35) as a solid (50 mg, yield, 74%). $^1$H NMR (MeOH-d$_4$, 300 MHz) δ 1.64-2.29 (m, 7H), 2.35-2.44 (m, 1H), 2.99-3.25 (m, 5H), 3.55-3.66 (m, 1H), 5.20-5.30 (m, 1H), 7.68 (d, J=8.8 Hz, 2H), 7.92 (d, J=8.8 Hz, 2H), 8.28 (d, J=1.4 Hz, 1H), 8.59 (d, J=1.4 Hz, 1H) ppm. MS (DCl/NH$_3$) m/z 339 (M+H)$^+$.

Example 17B

N-{4-[5-(1-azabicyclo[2.2.2]oct-3-yloxy)pyrazin-2-yl]phenyl}acetamide hemifumarate The product of Example 17A (50 mg, 0.15 mmol) in ethyl acetate/ethanol (3 mL, 1:1) was treated with fumaric acid (23 mg, 0.2 mmol) at ambient temperature for 10 hours. The title compound was obtained as a solid (40 mg, yield, 63%). $^1$H NMR (MeOH-d$_4$, 300 MHz) δ 1.77-2.17 (m, 6H), 2.21-2.37 (m, 1H), 2.47-2.56 (m, 1H), 3.13-3.40 (m, 5H), 3.71-3.83 (m, 1H), 5.31-5.38 (m, 1H), 6.68 (m, 1.2H), 7.68 (d, J=8.8 Hz, 2H), 7.92 (d, J=8.8 Hz, 2H), 8.31 (d, J=1.4 Hz, 1H), 8.59 (d, J=1.4 Hz, 1H) ppm. MS (DCl/NH$_3$) m/z 339 (M+H)$^+$. Anal. Calculated for C$_{19}$H$_{22}$N$_4$O$_2$.0.63C$_4$H$_4$O$_4$.0.7H$_2$O: C, 60.94; H, 6.16; N, 13.21. Found: C, 60.79; H, 6.18; N, 13.37.

Example 18

4-[2-(1-azabicyclo[2.2.2]oct-3-yloxy)pyrimidin-5-yl]aniline

Example 18A

3-[(5-bromopyrimidin-2-yl)oxy]quinuclidine

3-Quinuclidinol (Aldrich, 254 mg, 2 mmol) in tetrahydrofuran (Aldrich, anhydrous, 10 mL) was treated with potassium tert-butoxide (224 mg, 2 mmol) at ambient temperature for 1 hour. 2-Iodo-5-bromo-pyrimidine (Aldrich, 568 mg, 2 mmol) was then added. After stirring for 30 minutes, the mixture was treated with water (5 mL) and extracted with CHCl$_3$:isopropyl alcohol (10:1, 3×10 mL). The extracts were combined and concentrated under reduced pressure. The title compound was purified by flash chromatography (SiO$_2$, CH$_2$Cl$_2$:MeOH:NH$_3$.H$_2$O, 90:10:1, R$_f$ 0.15) as a solid (287 mg, yield, 50%). $^1$H NMR (300 MHz, MeOH-d$_4$) δ 1.52-1.65 (m, 1H), 1.66-1.93 (m, 2H), 2.00-2.15 (m, 1H), 2.22-2.31 (m, 1H), 2.79-3.09 (m, 5H), 3.38-3.49 (m, 1H), 5.06-5.15 (m, 1H), 8.64 (s, 2H) ppm. MS (DCl/NH$_3$) m/z 284 (M+H)$^+$ 286 (M+H)$^+$.

Example 18B tert-butyl 4-[2-(1-azabicyclo[2.2.2]oct-3-yloxy)pyrimidin-5-yl]phenylcarbamate The product of Example 18A (283 mg, 1 mmol) in tetrahydrofuran (anhydrous, 10 mL) was treated with t-butyl [4-(4,4,5,5-tetramethyl-[1,3,2]dioxaborolan-2-yl)-phenyl]-carbamate (Frontier, 319 mg, 1 mmol), Pd$_2$(dba)$_3$ (Strem Chemicals, 24 mg, 0.025 mmol), ($^t$Bu$_3$P)$_2$Pd (Strem Chemicals, 26 mg, 0.05 mmol), K$_2$CO$_3$ (Aldrich, 276 mg 2 mmol) and heated at 60° C. under N$_2$ for 15 hours. The resulting mixture was allowed to cool to room temperature, diluted with ethyl acetate (20 mL), and washed with brine (2×5 mL).

The organic phase was concentrated and the title product was purified by chromatography (SiO$_2$, CH$_2$Cl$_2$:MeOH: NH$_3$.H$_2$O, 90:10:1, R$_f$, 0.20) as a solid (340 mg, yield, 86%). $^1$H NMR (300 MHz, MeOH-d$_4$) δ 1.48-1.63 (m, 10H), 1.65-1.91 (m, 2H), 2.02-2.16 (m, 1H), 2.22-2.30 (m, 1H), 2.75-3.05 (m, 5H), 3.36-3.48 (m, 1H), 5.13-5.21 (m, 1H), 7.54 (s, 4H), 8.78 (s, 2H) ppm. MS (DCl/NH$_3$) m/z 397 (M+H)$^+$.

Example 18C

4-[2-(1-azabicyclo[2.2.2]oct-3-yloxy)pyrimidin-5-yl]aniline

The product of Example 18B (340 mg, 0.86 mmol) in CH$_2$Cl$_2$ (6 mL) was treated with trifluroacetic acid (Aldrich, 2 mL) at ambient temperature for 30 minutes and concentrated under reduced pressure. The title product was purified by chromatography (SiO$_2$, CH$_2$Cl$_2$:MeOH:NH$_3$.H$_2$O, 90:10:1, R$_f$ 0.07) as solid (150 mg, yield, 58%). $^1$H NMR (300 MHz, MeOH-d$_4$) δ 1.88-2.22 (m, 3H), 2.31-2.45 (m, 1H), 2.56-2.64 (m, 1H), 3.27-3.51 (m, 5H), 3.84-3.96 (m, 1H), 5.36-5.45 (m, 1H), 6.87 (d, J=8.5 Hz, 2H), 7.42 (d, J=8.5 Hz, 2H), 8.77 (s, 2H) ppm. MS (DCl/NH$_3$) m/z 297 (M+H)$^+$.

Example 18D

4-[2-(1-azabicyclo[2.2.2]oct-3-yloxy)pyrimidin-5-yl]aniline hemifumarate

The product of Example 18C (150 mg, 0.5 mmol) in ethyl acetate:ethanol (1:1, 5 mL) was treated with fumaric acid (58 mg, 0.5 mmol) at ambient temperature for 10 hours. The title compound was obtained as a solid (178.2 mg, yield, 98%). $^1$H NMR (300 MHz, MeOH-d$_4$) δ 1.74-2.11 (m, 3H), 2.20-2.36 (m, 1H), 2.44-2.53 (m, 1H), 3.13-3.40 (m, 5H), 3.68-3.79 (m, 1H), 5.27-5.35 (m, 1H), 6.68 (s, 1.2H), 6.81 (d, J=8.8 Hz, 2H), 7.37 (d, J=8.8 Hz, 2H), 8.74 (s, 2H) ppm. MS (DCl/NH$_3$) m/z 297 (M+H)$^+$. Anal. Calculated for C$_{17}$H$_{20}$N$_4$O.0.57C$_4$H$_4$O$_4$: C, 63.88; H, 6.19; N, 15.54. Found: C, 63.73; H, 6.21; N, 15.51.

Example 19

4-{2-[(3R)-1-azabicyclo[2.2.2]oct-3-yloxy]pyrimidin-5-yl}aniline

Example 19A (3R)-3-[(5-bromopyrimidin-2-yl)oxy]quinuclidine

The product of Example 9A (509 mg, 4 mmol) was treated with potassium tert-butoxide (448 mg, 4 mmol) and 2-iodo-5-bromo-pyrimidine (Aldrich, 1.14 g, 4 mmol) according to the procedure of Example 18A. The title compound was purified by flash chromatography (SiO$_2$, CH$_2$Cl$_2$:MeOH:NH$_3$—H$_2$O, 90:10:1, R$_f$ 0.15) as a solid (760 mg, yield, 67%). $^1$H NMR (300 MHz, MeOH-d$_4$) δ 1.52-1.65 (m, 1H), 1.66-1.93 (m, 2H), 2.03-2.15 (m, 1H), 2.22-2.31 (m, 1H), 2.79-3.09 (m, 5H), 3.41-3.52 (m, 1H), 5.06-5.15 (m, 1H), 8.64 (s, 2H) ppm. MS (DCl/NH$_3$) m/z 284 (M+H)$^+$ 286 (M+H)$^+$.

Example 19B tert-butyl 4-{2-[(3R)-1-azabicyclo[2.2.2]oct-3-yloxy]pyrimidin-5-yl}phenylcarbamate The product of Example 19A (160 mg, 0.57 mmol) was coupled with t-butyl [4-(4,4,5,5-tetramethyl-[1,3,2]dioxaborolan-2-yl)-phenyl]-carbamate (Frontier, 319 mg, 1 mmol) according to the procedure of Example 18B. The title product was purified by chromatography (SiO$_2$, CH$_2$Cl$_2$:MeOH:NH$_3$H$_2$O, 90:10:1, R$_f$ 0.20) as solid (150 mg, yield, 67%). $^1$H NMR (300 MHz, MeOH-d$_4$) δ 1.48-1.63 (m, 10H), 1.65-1.91 (m, 2H), 2.02-2.16 (m, 1H), 2.22-2.30 (m, 1H), 2.75-3.05 (m, 5H), 3.36-3.48 (m, 1H), 5.13-5.21 (m, 1H), 7.54 (s, 4H), 8.78 (s, 2H) ppm. MS (DCl/NH$_3$) m/z 397 (M+H)$^+$.

Example 19C

4-{2-[(3R)-1-azabicyclo[2.2.2]oct-3-yloxy]pyrimidin-5-yl}aniline

The product of Example 19B (150 mg, 0.38 mmol) was treated with trifluroacetic acid (2 mL) according to the procedure of Example 18C. The title compound was purified by chromatography (SiO$_2$, CH$_2$Cl$_2$:MeOH:NH$_3$.H$_2$O, 90:10:1, R$_f$ 0.07) as solid (30 mg, yield, 26%). $^1$H NMR (300 MHz, MeOH-d$_4$) δ 1.88-2.22 (m, 3H), 2.31-2.45 (m, 1H), 2.56-2.64 (m, 1H), 3.27-3.51 (m, 5H), 3.84-3.96 (m, 1H), 5.36-5.45 (m, 1H), 6.87 (d, J=8.5 Hz, 2H), 7.42 (d, J=8.5 Hz, 2H), 8.77 (s, 2H) ppm. MS (DCl/NH$_3$) m/z 297 (M+H)$^+$.

Example 19D

4-{2-[(3R)-1-azabicyclo[2.2.2]oct-3-yloxy]pyrimidin-5-yl}aniline hemifumarate

The product of Example 19C (30 mg, 0.1 mmol) in ethyl acetate/ethanol (1:1, 2 mL) was treated with fumaric acid (12 mg, 0.1 mmol) at ambient temperature for 10 hours. The title compound was obtained as a solid (13.6 mg, yield, 35%). $^1$H NMR (300 MHz, MeOH-d$_4$) δ 1.84-2.20 (m, 3H), 2.28-2.44 (m, 1H), 2.53-2.62 (m, 1H), 3.16-3.45 (m, 5H), 3.81-3.91 (m, 1H), 5.34-5.42 (m, 1H), 6.68 (s, 1.5H), 6.81 (d, J=8.1 Hz, 2H), 7.37 (d, J=8.5 Hz, 2H), 8.75 (s, 2H) ppm. MS (DCl/NH$_3$) m/z 297 (M+H)$^+$. Anal. Calculated for C$_{17}$H$_{20}$N$_4$O.0.7C$_4$H$_4$O$_4$.0.45H$_2$O: C, 61.65; H, 6.19; N, 14.52. Found: C, 61.41; H, 6.02; N, 14.80.

Example 20

3-[2-(1-azabicyclo[2.2.2]oct-3-yloxy)pyrimidin-5-yl]aniline

Example 20A

3-[2-(1-azabicyclo[2.2.2]oct-3-yloxy)pyrimidin-5-yl]aniline

The product of Example 18A (160 mg, 0.57 mmol) was coupled with 3-aminophenylboronic acid (Lancaster, 157 mg, 1.14 mmol) according to the procedure of Example 1B. The title product was purified by chromatography (SiO$_2$, CH$_2$Cl$_2$:MeOH:NH$_3$—H$_2$O, 90:10:1, R$_f$ 0.1) as solid (144 mg, yield, 86%). $^1$H NMR (300 MHz, MeOH-d$_4$) δ 1.48-1.62 (m, 1H), 1.65-1.90 (m, 2H), 2.01-2.15 (m, 1H), 2.21-

2.29 (m, 1H), 2.74-3.04 (m, 5H), 3.36-3.47 (m, 1H), 5.12-5.20 (m, 1H), 6.75 (ddd, J=8.2, 2.1, 1.0 Hz, 1H), 6.89 (ddd, J=7.4, 1.7, 1.0 Hz, 1H), 6.93 (t, J=1.8 Hz, 1H), 7.20 (t, J=7.8 Hz, 1H), 8.74 (s, 2H) ppm. MS (DCl/NH$_3$) m/z 297 (M+H)$^+$.

Example 20B

3-[2-(1-azabicyclo[2.2.2]oct-3-yloxy)pyrimidin-5-yl]aniline hemifumarate

The product of Example 20A (144 mg, 0.48 mmol) in ethyl acetate/ethanol (1:1, 5 mL) was treated with fumaric acid (58 mg, 0.5 mmol) at ambient temperature for 10 hours. The title compound was obtained as a solid (122 mg, yield, 62%). $^1$H NMR (300 MHz, MeOH-d$_4$) δ 1.78-2.13 (m, 3H), 2.22-2.38 (m, 1H), 2.48-2.55 (m, 1H), 3.12-3.39 (m, 5H), 3.71-3.83 (m, 1H), 5.31-5.39 (m, 1H), 6.67 (s, 1.8H), 6.76 (ddd, J=8.2, 2.1, 1.0 Hz, 1H), 6.90 (ddd, J=7.4, 1.7, 1.0 Hz, 1H) 6.94 (t, J=1.8 Hz, 1H), 7.21 (t, J=7.8 Hz, 1H), 8.74 (s, 2H) ppm. MS (DCl/NH$_3$) m/z 297 (M+H)$^+$. Anal. Calculated for C$_{17}$H$_{20}$N$_4$O.0.9C$_4$H$_4$O$_4$.0.6H$_2$O: C, 60.11; H, 6.07; N, 13.61. Found: C, 60.00; H, 5.88; N, 13.99.

Example 21

3-{2-[(3R)-1-azabicyclo[2.2.2]oct-3-yloxy]pyrimidin-5-yl}aniline

Example 21A

3-{2-[(3R)-1-azabicyclo[2.2.2]oct-3-yloxylpyrimidin-5-yl}aniline

The product of Example 19A (280 mg, 1.0 mmol) was coupled with 3-aminophenylboronic acid (Lancaster, 276 mg, 2.0 mmol) according to the procedure of Example 1B. The title product was purified by chromatography (SiO$_2$, CH$_2$Cl$_2$:MeOH:NH$_3$.H$_2$O, 90:10:1, R$_f$ 0.1) as a solid (230 mg, yield, 77%). $^1$H NMR (300 MHz, MeOH-d$_4$) δ 1.48-1.62 (m, 1H), 1.65-1.90 (m, 2H), 2.01-2.15 (m, 1H), 2.21-2.29 (m, 1H), 2.74-3.04 (m, 5H), 3.36-3.47 (m, 1H), 5.12-5.20 (m, 1H), 6.75 (ddd, J=8.2, 2.1, 1.0 Hz, 1H), 6.89 (ddd, J=7.4, 1.7, 1.0 Hz, 1H), 6.93 (t, J=1.8 Hz, 1H), 7.20 (t, J=7.8 Hz, 1H), 8.74 (s, 2H) ppm. MS (DCl/NH$_3$) m/z 297 (M+H)$^+$.

Example 21B

3-{2-[(3R)-1-azabicyclo[2.2.2]oct-3-yloxy]pyrimidin-5-yl}aniline fumarate

The product of Example 21A (230 mg, 0.77 mmol) in ethyl acetate:ethanol (1:1, 5 mL) was treated with fumaric acid (90 mg, 0.77 mmol) at ambient temperature for 10 hours. The title compound was obtained as a solid (244 mg, yield, 75%). $^1$H NMR (300 MHz, MeOH-d$_4$) δ 1.78-2.13 (m, 3H), 2.22-2.38 (m, 1H), 2.48-2.55 (m, 1H), 3.12-3.39 (m, 5H), 3.71-3.83 (m, 1H), 5.31-5.39 (m, 1H), 6.67 (s, 1.8H), 6.76 (ddd, J=8.2, 2.1, 1.0 Hz, 1H), 6.90 (ddd, J=7.4, 1.7, 1.0 Hz, 1H) 6.94 (t, J=1.8 Hz, 1H), 7.21 (t, J=7.8 Hz, 1H), 8.74 (s, 2H) ppm. MS (DCl/NH$_3$) m/z 297 (M+H)$^+$. Anal. Calculated for C$_{17}$H$_{20}$N$_4$O.1.07C$_4$H$_4$O$_4$: C, 60.77; H, 5.82; N, 13.32. Found: C, 60.61; H, 5.79; N, 13.36.

Example 22

3-{2-[(3S)-1-azabicyclo[2.2.2]oct-3-yloxy]pyrimidin-5-yl}aniline

Example 22A

(3S)-3-[(5-bromopyrimidin-2-yl)oxy]quinuclidine

The product of Example 6D (508 mg, 4 mmol) was treated with potassium tert-butoxide (448 mg, 4 mmol) and 2-iodo-5-bromo-pyrimidine (Aldrich, 1.14 g, 4 mmol) according to the procedure of Example 18A. The title compound was purified by flash chromatography (SiO$_2$, CH$_2$Cl$_2$:MeOH:NH$_3$.H$_2$O, 90:10:1, R$_f$ 0.15) as a solid (780 mg, yield, 69%). $^1$H NMR (300 MHz, MeOH-d$_4$) δ 1.52-1.65 (m, 1H), 1.66-1.93 (m, 2H), 2.03-2.15 (m, 1H), 2.22-2.31 (m, 1H), 2.79-3.09 (m, 5H), 3.41-3.52 (m, 1H), 5.06-5.15 (m, 1H), 8.64 (s, 2H) ppm. MS (DCl/NH$_3$) m/z 284 (M+H)$^+$ 286 (M+H)$^+$.

Example 22B

3-{2-[(3S)-1-azabicyclo[2.2.2]oct-3-yloxy]pyrimidin-5-yl}aniline

The product of Example 22A (284 mg, 1.0 mmol) was treated with 3-aminophenylboronic acid (Lancaster, 276 mg, 2.0 mmol) according to the procedure of Example 1B. The title product was purified by chromatography (SiO$_2$, CH$_2$Cl$_2$:MeOH:NH$_3$.H$_2$O, 90:10:1, R$_f$ 0.1) as solid (285 mg, yield, 96%). $^1$H NMR (300 MHz, MeOH-d$_4$) δ 1.48-1.62 (m, 1H), 1.61-1.91 (m, 2H), 2.01-2.16 (m, 1H), 2.22-2.30 (m, 1H), 2.74-3.05 (m, 5H), 3.36-3.47 (m, 1H), 5.12-5.20 (m, 1H), 6.75 (ddd, J=8.2, 2.1, 1.0 Hz, 1H), 6.89 (ddd, J=7.4, 1.7, 1.0 Hz, 1H), 6.93 (t, J=1.8 Hz, 1H), 7.20 (t, J=7.8 Hz, 1H), 8.74 (s, 2H) ppm. MS (DCl/NH$_3$) m/z 297 (M+H)$^+$.

Example 22C

3-{2-[(3S)-1-azabicyclo[2.2.2]oct-3-yloxy]pyrimidin-5-yl}aniline fumarate

The product of Example 22B (284 mg, 0.96 mmol) in ethyl acetate:ethanol (1:1, 10 mL) was treated with fumaric acid (116 mg, 1.0 mmol) at ambient temperature for 10 hours. The title compound was obtained as a solid (351 mg, yield, 87%). $^1$H NMR (300 MHz, MeOH-d$_4$) δ 1.78-2.13 (m, 3H), 2.22-2.38 (m, 1H), 2.48-2.55 (m, 1H), 3.12-3.39 (m, 5H), 3.71-3.83 (m, 1H), 5.31-5.39 (m, 1H), 6.67 (s, 1.8H), 6.76 (ddd, J=8.2, 2.1, 1.0 Hz, 1H), 6.90 (ddd, J=7.4, 1.7, 1.0 Hz, 1H) 6.94 (t, J=1.8 Hz, 1H), 7.21 (t, J=7.8 Hz, 1H), 8.79 (s, 2H) ppm. MS (DCl/NH$_3$) m/z 297 (M+H)$^+$. Anal. Calculated for C$_{17}$H$_{20}$N$_4$O.1.0C$_4$H$_4$O$_4$.0.25H$_2$O: C, 60.49; H, 5.92; N, 13.44. Found: C, 60.49; H, 5.94; N, 13.35.

Example 23

5-[2-(1-azabicyclo[2.2.2]oct-3-yloxy)pyrimidin-5-yl]-2-methylaniline

Example 23A

5-[2-(1-azabicyclo[2.2.2]oct-3-yloxy)pyrimidin-5-yl]-2-methylaniline

The product of Example 18A (160 mg, 0.57 mmol) was treated with 3-amino-4-methyl-phenylboronic acid (Lancaster, 302 mg, 2.0 mmol) according to the procedure of Example 1B. The title product was purified by chromatography (SiO$_2$, CH$_2$Cl$_2$:MeOH:NH$_3$.H$_2$O, 90:10:1, R$_f$, 0.1) as solid (45 mg, yield, 26%). $^1$H NMR (300 MHz, MeOH-d$_4$) δ 1.48-1.62 (m, 1H), 1.65-1.90 (m, 2H), 2.01-2.16 (m, 1H), 2.19 (s, 3H), 2.22-2.29 (m, 1H), 2.74-3.01 (m, 5H), 3.36-3.47 (m, 1H), 5.12-5.20 (m, 1H), 6.86 (dd, J=7.51.7 Hz, 1H), 6.95 (d, J=1.7 Hz, 1H), 7.10 (d, J=8.1 Hz, 1H), 8.73 (s, 2H) ppm. MS (DCl/NH$_3$) m/z 311 (M+H)$^+$.

Example 23B

5-[2-(1-azabicyclo[2.2.2]oct-3-yloxy)pyrimidin-5-yl]-2-methylaniline fumarate

The product of Example 23A (45 mg, 0.14 mmol) in ethyl acetate/ethanol (1:1, 3 mL) was treated with fumaric acid (23 mg, 0.2 mmol) at ambient temperature for 10 hours. The title compound was obtained as a solid (50 mg, yield, 78%). $^1$H NMR (300 MHz, MeOH-d$_4$) δ 1.85-2.24 (m, 6H), 2.30-2.44 (m, 1H), 2.55-2.62 (m, 1H), 3.23-3.46 (m, 5H), 3.82-3.92 (m, 1H), 5.36-5.44 (m, 1H), 6.69 (s, 2H), 6.87 (dd, J=2.0, 7.8 Hz, 1H), 6.96 (d, J=1.7 Hz, 1H), 7.12 (d, J=8.1 Hz, 1H), 8.78 (s, 2H). ppm. MS (DCl/NH$_3$) m/z 311 (M+H)$^+$. Anal. Calculated for C$_{18}$H$_{22}$N$_4$O.1.15C$_4$H$_4$O$_4$: C, 61.15; H, 6.04; N, 12.62. Found: C, 61.14; H, 6.08; N, 12.38.

Example 24

N-1-azabicyclo[2.2.2]oct-3-yl-1,1'-biphenyl-4,4'-diamine

Example 24A

N-1-azabicyclo[2.2.2]oct-3-yl-1,1'-biphenyl-4,4'-diamine

3-Quinuclidinone hydrochloride (Aldrich, 1.61 g, 10 mmol) in acetic acid (25 mL) was treated with biphenyl-4,4'-diamine (Aldrich, 0.92 g, 5.0 mmol), Na$_2$SO$_4$ (anhydrous, Aldrich, 7.40 g, 50 mmol) and NaBH(OAc)$_3$ (Aldrich, 3.16 g, 15 mmol) at ambient temperature for 15 hours. The reaction mixture was slowly poured into a flask containing 75 mL of saturated NaHCO$_3$, stirred for 20 minutes, and extracted with ethyl acetate (3×100 mL). The extracts were combined and washed with brine (2×20 mL). The organic phase was concentrated under reduced pressure and the title compound was purified by chromatography (SiO$_2$, CH$_2$Cl$_2$:MeOH:NH$_3$.H$_2$O, 80:20:4, R$_f$, 0.10) as a solid (0.98 g, yield, 67%). $^1$H NMR (MeOH-d$_4$, 300 MHz) δ 1.40-1.52 (m, 1H), 1.64-1.84 (m, 2H), 1.89-2.04 (m, 2H), 2.57 (ddd, J=13.9, 5.2, 2.1 Hz, 1H) 2.75-3.00 (m, 4H), 3.27-3.35 (m, 1H), 3.50-3.60 (m, 1H), 6.61-6.69 (m, 2H), 6.80-6.86 (m, 2H), 6.92-6.97 (m, 2H), 7.06-7.13 (m, 2H) ppm. MS (DCl/NH$_3$) m/z 294 (M+H)$^+$.

Example 24B

N-1-azabicyclo[2.2.2]oct-3-yl-1,1'-biphenyl-4,4'-diamine fumarate

The product of Example 24A (150 mg, 0.51 mmol) was treated with fumaric acid (Aldrich, 70 mg, 0.6 mmol) in ethyl acetate/methanol (10:1, 20 mL) at ambient temperature for 10 hours. The title compound was obtained as a solid (210 mg, yield, 99%): $^1$H NMR (MeOH-d$_4$, 300 MHz) δ 1.81-1.92 (m, 1H), 2.02-2.15 (m, 2H), 2.22-2.35 (m, 2H), 3.02 (ddd, J=12.5, 4.7, 1.7 Hz, 1H) 3.24-3.44 (m, 4H), 3.77 (ddd, J=12.9, 9.2, 2.4 Hz, 1H), 3.90-4.02 (m, 1H), 6.64-6.72 (m, 4H), 6.81-6.90(m, 2H), 6.96-7.01 (m, 2H), 7.08-7.14 (m, 2H) ppm. MS (DCl/NH$_3$) m/z 294 (M+H)$^+$. Anal. Calculated for C$_{19}$H$_{23}$N$_3$.1.2C$_4$H$_4$O$_4$.0.3H$_2$O: C, 65.25; H, 6.53; N, 9.59. Found: C, 65.20; H, 6.23; N, 9.28.

Example 25

4'-(1-Oxy-1-aza-bicyclo[2.2.2]oct-3-yloxy)-biphenyl-3-ylamine bis(hydrogen chloride)

Example 25A

4'-(1-Oxy-1-aza-bicyclo[2.2.2]oct-3-yloxy)-biphenyl-3-ylamine

The product of Example 1C (124 mg, 0.33 mmol) was treated with H$_2$O$_2$ (Aldrich, aq. 35%, 32 µL, 0.33 mmol) in acetonitrile (2 mL) and water (2 mL) at ambient temperature for 5 h. The mixture was quenched by Na$_2$SO$_3$ solution carefully till no more peroxide was noticed, and it was then concentrated under vacuum. The title product was purified by preparative HPLC (Xterra™, column, Xterra RP-18, 5 µm, 30×100 mm. Eluting Solvent, MeCN/H$_2$O (with 0.2% v. TFA), (v. 90/10 to 10/90 over 20 min.) Flow rate, 75 mL/min., uv, 250 nm) as solid (50 mg, yield, 49%). $^1$H NMR (MeOH-d$_4$, 300 MHz) δ 1.84-2.25 (m, 3H), 2.31-2.53 (m, 2H), 3.33-3.52 (m, 5H), 3.74-3.97 (m, 1H), 4.91-5.02 (m, 1H), 6.67 (dd, J=8.0, 2.2 Hz, 1H), 6.89 (d, J=7.5 Hz, 1H), 6.92-6.96 (m, 1H), 6.97-7.05 (m, 2H), 7.13 (t, J=7.8 Hz, 1H), 7.43-7.67 (m, 2H) ppm. MS (DCl/NH$_3$) m/z 311 (M+H)$^+$.

Example 25B

4'-(1-Oxy-1-aza-bicyclo[2.2.2]oct-3-yloxy)-biphenyl-3-ylamine bis(hydrogen chloride)

The product of Example 25A (50 mg, 0.16 mmol) was treated with HCl (Aldrich, 4 M in dioxane, 0.5 mL) in EtOAc (5 mL) at ambient temperature for 1 hour to give the title compound as yellow solid (50.0 mg, 40%). $^1$H NMR (MeOH-D$_4$, 300 MHz) δ 2.07-2.41 (m, 3H), 2.46-2.64 (m, 2H), 3.67-3.95 (m, 5H), 4.24-4.38 (m, 1H), 5.03-5.18 (m, 1H), 7.05-7.18 (m, 3H), 7.37 (s, 1H), 7.41-7.47 (m, 2H), 7.58-7.67 (m, 2H) ppm. MS (DCl/NH$_3$) m/z 311(M+H)$^+$. Anal. Calculated for C$_{19}$H$_{22}$N$_4$O$_2$.2.00HCl.0.50H$_2$O: C, 58.17; H, 6.42; N, 7.14. Found: C, 57.89; H, 6.56; N, 6.82.

Example 26

[4'-(1-Aza-bicyclo[2.2.2]oct-3-yloxy)-biphenyl-4-yl]-p-tolyl-amine trifluroacetic acid A Smith Process vessel (0.5-2 ml, Personal Chemistry) was charged with a stir bar. To the vessel was added the product of Example 1A (10 mg, 0.025 mmol) in toluene (0.8 mL) and 1,4-dioxane (0.4 mL). p-Toluidine (Aldrich, 4 mg, 0.038 mmol) and t-BuONa (Aldrich, 3.6 mg, 0.038 mmol,) were added to above solution. The Mixture was purged under N$_2$ followed by addition of Pd$_2$(dba)$_3$ (Aldrich, 1 mg, 0.001 mmol,) and Pd(t-Bu$_3$P)$_2$ (Strem Chemicals, 1.2 mg, 0.002 mmol). The reaction vessel was sealed and heated in microwave to 150° C. for 35 min in an Emry™ Optimizer microwave. After cooling, the reaction vessel was uncapped and filtered through a plug of silica, washed with MeOH.

The filtrate was collected and dried. The title compound was purified by preparative HPLC (Gilson, column, Symmetry® C-8 7 μm, 40×100 mm. Eluting Solvent, MeCN/H$_2$O (with 0.2% v. TFA) (v. 90/10 to 10/90 over 20 min.) Flow rate, 75 mL/min., uv, 254 nm) as solid (5.0 mg, yield, 40%). $^1$H NMR (300 MHz, DMSO-d$_6$) δ 1.76 (m, 1H), 1.92 (m, 2H), 2.10 (m, 1H), 2.24 (s, 3H), 2.40 (m, 1H), 3.23-3.30 (m, 5H), 3.77 (m, 1H), 4.86 (m, 1H), 6.99-7.09 (m, 8H), 7.47 (d, J=9 Hz, 2H), 7.56 (d, J=9 Hz, 2H), 8.10 (br, 1H) ppm; MS (DCl/NH$_3$) 385 (M+H)$^+$.

Example 27

[4'-(1-Aza-bicyclo[2.2.2]oct-3-yloxy)-biphenyl-4-yl]-cyclohexylmethyl-amine trifluroacetic acid The product of Example 1A (10 mg, 0.025 mmol) was coupled with C-cyclohexyl-methylamine (Aldrich, 4.3 mg, 0.038 mmol) according to the procedure of Example 26. The title compound was purified by preparative HPLC (Gilson, column, Symmetry® C-8 7 μm, 40×100 mm. Eluting Solvent, MeCN/H$_2$O (with 0.2% v. TFA) (v. 90/10 to 10/90 over 20 min.) Flow rate, 75 mL/min., uv, 254 nm) as solid (8.2 mg, yield, 65%). $^1$H NMR (300 MHz, DMSO-d$_6$) 6 (ppm) 1.53 (m, 4H), 1.68 (m, 3H), 1.91 (m, 4H), 2.09 (m, 1H), 2.39 (m, 1H), 3.23-3.30 (m, 5H), 3.77 (m, 7H), 6.71 (d, J=9 Hz, 2H), 6.99 (d, J=9 Hz, 2H), 7.39 (d, J=9 Hz, 2H), 7.51 (d, J=9 Hz, 2H), 9.58 (br, 1H); MS (DCl/NH$_3$) 391 (M+H)$^+$.

Example 28

2-[4-(1-Aza-bicyclo[2.2.2]oct-3-yloxy)-phenyl]-8-iodo-6H,12H-5,11-methano-dibenzo[b,f][1,5]diazocine fumarate Example 28A 2,8-Diiodo-6H,12H-5,11-methano-dibenzo[b,f][1,5]diazocine The mixture of 4-Iodo-phenylamine (Aldrich, 6.57 g, 30 mmol) and paraformaldehyde (Aldrich, 1.80 g, 60 mmol) in trifluoroacetic acid (Aldrich, 60 mL) was stirred at ambient temperature for 15 hour. It was then concentrated, dissolved in water (10 mL) and neutralized with NH$_3$.H$_2$O till pH=9. The mixture was extracted with EtOAc (3×50 mL). The extracts were combined and concentrated. The title compound was purified by chromatography (SiO$_2$, hexane: EtOAc, 50:50, R$_f$ 0.40) as solid (2.70 g, yield, 38%). $^1$H NMR (300 MHz, CDCl$_3$) δ 4.09 (d, J=17.0 Hz, 2H), 4.26 (s, 2H), 4.63 (d, J=16.6 Hz, 2H), 6.89 (d, J=8.5 Hz, 2H), 7.16-7.31 (m, 2H), 7.47 (dd, J=8.5, 2.0 Hz, 2H) ppm. MS (DCl/NH$_3$) 475 (M+H)$^+$.

Example 28B

3-[4-(trimethylstannyl)phenoxyl]quinuclidine

The product of Example 1A (330 mg, 1 mmol) was coupled with hexamethylditin (Aldrich, 654 mg, 2 mmol) under the catalysis of Pd(PPh$_3$)$_4$ (Aldrich, 116 mg, 0.1 mmol) in toluene (10 mL) at 110° C. under N$_2$ for 2 hours. After the reaction was complete, it was cooled down to room temperature, diluted with EtOAc (50 mL) and washed with brine (2×5 mL). The organic solution was concentrated under reduced pressure and the title compound was purified by flash chromatography (SiO$_2$, CH$_2$Cl$_2$:MeOH:NH$_3$—H$_2$O, 90:10:1, R$_f$ 0.35) as solid (300 mg, yield, 82%). $^1$H NMR (300 MHz, MeOH-D$_4$) δ 0.25 (s, 9H), 1.79-2.16 (m, 3H), 2.23-2.36 (m, 1H), 2.45-2.52 (m, 1H), 3.17-3.43 (m, 5H), 3.73-3.83 (m, 1H), 4.84-4.92 (m, 1H), 6.96 (d, J=8.5 Hz, 2H), 7.41 (d, J=8.5 Hz, 2H) ppm. MS (DCl/NH$_3$): m/z 364 (M+H)$^+$, 366 (M+H)$^+$, 368 (M+H)$^+$.

Example 28C

2-[4-(1-Aza-bicyclo[2.2.2]oct-3-yloxy)-phenyl]-8-iodo-6H,12H-5,11-methano-dibenzo[b,f][1,5]diazocine fumarate The product of Example 28B (300 mg, 0.8 mmol) was coupled with the product of Example 28A (450 mg, 0.95 mmol) under the catalysis of Pd$_2$(dba)$_3$ (Aldrich, 30 mg, 0.033 mmol) and P(o-tolyl)$_3$ (Aldrich, 30 mg, 0.1 mmol) in dry DMF (Aldrich, 4 mL) at 80° C. for 3 hours. It was then concentrated under reduced pressure and the free base of the title compound was purified by preparative HPLC (Xterra™, column, Xterra RP-18 5 μm, 30×100 mm. Eluting Solvent, MeCN/H$_2$O(NH$_4$HCO$_3$, 0.1 M, pH=10) (v. 90/10 to 10/90 over 20 min.) Flow rate, 75 mL/min., uv, 250 nm) (60 mg, yield, 14%). The free base was treated with fumaric acid (Aldrich, 17 mg, 0.15 mmol) in EtOAc/MeOH (v.10:1, 5 mL) at ambient temperature for 10 hours to give the title compound (56 mg, 74%). $^1$H NMR (300 MHz, MeOH-D4) δ ppm 1.77-2.18 (m, 3H) 2.22-2.36 (m, 1H) 2.45-2.54 (m, 1H), 3.15-3.43 (m, 5H), 3.71-3.82 (m, J=14.9 Hz, 1H), 4.14-4.41 (m, 3H), 4.61-4.93 (m, 3H), 6.69 (s, 2H), 6.91-7.04 (m, 3H), 7.12-7.22 (m, J=8.8 Hz, 2H), 7.31-7.42 (m, 2H), 7.44-7.54 (m, 3H) ppm. MS (DCl/NH$_3$) m/z 550 (M+H)$^+$. Anal. Calculated for C$_{28}$H$_{28}$N$_3$OI.1.15 C$_4$H$_4$O$_4$: C, 57.33; H, 4.81; N, 6.15. Found: C, 57.13; H, 4.42; N, 6.22.

Example 29

4-{6-[(3R)-1-Aza-bicyclo[2.2.2]oct-3-ylox]-pyridazin-3-yl}-phenylamine tri(hydrogen chloride)

Example 29A 6-(4-Bromo-phenyl)-4,5-dihydro-2H-pyridazin-3-one 4-(4-Bromo-phenyl)-4-oxo-butyric acid (Aldrich, 25.0 g, 97.3 mmol) was treated with NH$_2$NH$_2$—H$_2$O (Aldrich, 55%, 9.1 mL, 156 mmol) in EtOH (Aldrich, 100 mL) at refluxing for 2 h. It was cooled down to ambient temperature and the white solid was filtered off to give the title compound (24.2 g, 98%). $^1$H NMR (CDCl$_3$, 300 MHz) δ 2.50-2.76 (m, 2H), 2.85-3.09 (m, 2H), 7.43-7.71 (m, 4H), 8.55 (s, 1H) ppm. MS (DCl/NH$_3$) m/z 253 (M+H)$^+$, 255 (M+H)$^+$, 270 (M+NH$_4$)$^+$, 272 (M+NH$_4$)$^+$.

Example 29B 6-(4-Bromo-Phenyl)-4,5-dihydro-2H-pyridazin-3-one

The product of Example 29A (24.0 g, 95 mmol) was oxidized with bromine (Aldrich, 18.81 g, 6.1 mL, 104.5 mmol) in HOAc (Aldrich, 200 mL) at 100C for 1 h. The brown mixture was then cooled down to ambient temperature. The white solid was filtered off and the filtrate was washed with water (2×20 mL). The solid was collected and dried under vacuum to give the title compound (25.0 g, 100%). $^1$H NMR (CDCl$_3$, 300 MHz) δ 7.07 (d, J=10.2 Hz, 1H), 7.55-7.69 (m, 4H), 7.72 (d, J=9.8 Hz, 1H) ppm. MS (DCl/NH$_3$) m/z 251 (M+H)$^+$, 253 (M+H)$^+$, 268 (M+NH$_4$)$^+$, 270 (M+NH$_4$)$^+$.

Example 29C 3-(4-Bromo-phenyl)-6-chloro-pyridazine

The product of Example 29B (25.0 g, 100 mmol) was stirred in POCl$_3$ (Aldrich, 200 mL) at 100° C. for 18 h. Most of POCl$_3$ was then distilled off (around 150 mL was collected). The residue was then poured into 300 mL of ice/water and stirred vigorously for 1 h. The solid was filtered off. The filtrate was washed with water (2×50 mL) and dried under vacuum to give the title compound (26.2 g, 98%). $^1$H NMR (MeOH-D$_4$, 300 MHz) δ 7.72 (d, J=8.8 Hz, 2H), 7.86 (d, J=8.8 Hz, 1H), 8.02 (d, J=8.8 Hz, 2H), 8.19 (d, J=9.2 Hz, 1H) ppm. MS (DCl/NH$_3$) m/z 269 (M+H)$^+$, 271 (M+H)$^+$, 273 (M+H)$^+$.

Example 29D (3R)-3-[6-(4-Bromo-phenyl)-pyridazin-3-yloxy]-1-aza-bicyclo[2.2.2]octane The product of Example 29C (2.43 g, 9 mmol) was coupled with the product of Example 6B (1.27 g, 10 mmol) using t-BuOK (Aldrich, 1.12 g, 10 mmol) as base in THF (anhydrous, Aldrich, 50 mL) at ambient temperarure for 10 h. After the reaction was complete, it was concentrated under reduced pressure. The residue was dissolved in CHCl$_3$/PrOH (v.10:1, 50 mL) and washed with brine (2×5 mL). The organic solution was concentrated under reduced pressure and the title compound was purified by chromatography (SiO$_2$, CH$_2$Cl$_2$:MeOH:NH$_3$.H$_2$O, 90:10:2, R$_f$, 0.30) as slightly yellow solid (3.30 g, 100%). $^1$H NMR (MeOH-D$_4$, 300 MHz) 1.47-1.66 (m, 1H), 1.66-1.93 (m, 2H), 1.96-2.18 (m, 1H), 2.23-2.42 (m, 1H), 2.71-3.06 (m, 5H), 3.38-3.58 (m, 1H), 5.17-5.47 (m, 1H), 7.28 (d, J=9.2 Hz, 1H), 7.59-7.78 (m, 2H), 7.82-7.99 (m, 2H), 8.06 (d, J=9.2 Hz, 1H) ppm. MS (DCl/NH$_3$) m/z 360 (M+H)$^+$, 362 (M+H)$^+$.

Example 29E

{4-{6-[(3R)-1-Aza-bicyclo[2.2.2]oct-3-yloxy]-pyridazin-3-yl}-phenyl-benzhydrylidene-amine The product of Example 29D (360 mg, 1 mmol) was coupled with benzhydrylideneamine (Aldrich, 270 mg, 1.5 mmol) under the catalysis of Pd$_2$(dba)$_3$ (Aldrich, 18.3 mg, 0.02 mmol) and Xantphos (Strem Chemicals, 36 mg, 0.06 mmol) with t-BuONa (Aldrich, 150 mg, 1.5 mmol) in toluene (anhydrous, Aldrich, 10 mL) at 100° C. for 2 h. The mixture was then cooled down to ambient temperature and diluted with EtOAc (50 mL), washed with water (2×5 mL). The organic solution was concentrated and the title compound was purified by chromatography (SiO$_2$, CH$_2$Cl$_2$: MeOH:NH$_3$.H$_2$O, 90:10:1, R$_f$, 0.4) as a solid (360 mg, yield, 78%). $^1$H NMR (300 MHz, CD$_3$OD) δ 1.45-1.63 (m, 1H), 1.64-1.94 (m, 2H), 1.94-2.13 (m, 1H), 2.23-2.41 (m, 1H), 2.71-3.06 (m, 5H), 3.39-3.55 (m, 1H), 5.10-5.37 (m, 1H), 6.82-6.93 (m, 2H), 7.12-7.23 (m, 3H), 7.25-7.35 (m, 3H), 7.39-7.57 (m, 3H), 7.67-7.74 (m, 2H), 7.74-7.83 (m, 2H), 7.96 (d, J=9.2 Hz, 1H) ppm. MS (DCl/NH$_3$): 461 (M+H)$^+$.

Example 29F

4-{6-[(3R)-1-Aza-bicyclo[2.2.2]oct-3-yloxy]-pyridazin-3-yl}-phenylamine

The product of Example 29E (360 mg, 0.78 mmol) was treated with HCl (aq. 10%, 5 mL) in THF (5 mL) at ambient temperature for 4 h. It was then concentrated and the title compound was purified by chromatography (SiO$_2$, CH$_2$Cl$_2$: MeOH:NH$_3$.H$_2$O, 90:10:1, R$_f$, 0.1) as solid (210 mg, yield, 90%). $^1$H NMR (300 MHz, CD$_3$OD) δ 1.44-1.66 (m, 1H), 1.65-1.94 (m, 2H), 1.95-2.16 (m, 1H), 2.20-2.40 (m, 1H), 2.68-3.06 (m, 5H), 3.37-3.57 (m, 1H), 5.15-5.37 (m, 1H), 6.65-6.89 (m, 2H), 7.18 (d, J=9.5 Hz, 1H), 7.55-7.81 (m, 2H), 7.93 (d, J=9.2 Hz, 1H) ppm. MS (DCl/NH$_3$): 297 (M+H)$^+$.

Example 29G

4-{6-[(3R)-1-Aza-bicyclo[2.2.2]oct-3-yloxy]-pyridazin-3-yl}-phenylamine tri(hydrogen chloride)

The product of Example 29F (50.0 mg, 0.17 mmol) was treated with HCl (Aldrich, 4 M in dioxane, 0.25 mL, 1 mmol) in EtOAc (5 mL) at ambient temperature for 5 hours to give the title compound (55 mg, yield, 81%). $^1$H NMR (300 MHz, CD$_3$OD) δ 1.89-2.25 (m, 3H), 2.29-2.53 (m, 1H), 2.63-2.75 (m, 1H), 3.32-3.61 (m, 5H), 3.97 (dd, J=13.9, 8.5 Hz, 1H), 5.40-5.66 (m, 1H), 7.23-7.37 (m, 2H), 7.60 (d, J=9.2 Hz, 1H), 7.96-8.13 (m, 2H), 8.37 (d, J=9.2 Hz, 1H) ppm. MS (DCl/NH$_3$): 297 (M+H)$^+$. Anal. Calculated for C$_{28}$H$_{28}$N$_3$OI.3.00 HCl.1.36H$_2$O: C, 47.46; H, 6.03; N, 13.02. Found: C, 47.86; H, 5.88; N, 12.58.

Example 30

4-{6-[(3R)-1-Aza-bicyclo[2.2.2]oct-3-yloxy]-pyridazin-3-yl}-2-bromo-phenylamine bis hydrogen chloride)

Example 30A

4-{6-[(3R)-1-Aza-bicyclo[2.2.2]oct-3-yloxy]-pyridazin-3-yl}-2-bromo-phenylamine

The product of Example 29F (150 mg, 0.5 mmol) was treated with HOAc (36 μL, 36 mg, 0.6 mmol) in MeCN (5 mL) at ambient temperature for 5 min. N-bromosuccinimide (Aldrich, 100 mg, 0.55 mol) in MeCN (5 mL) was then added to the above solution at 0° C. and stirred at 0° C. for 1 h. It was then concentrated under reduced pressure. The title compound was purified by preparative HPLC (Xterra™, column, Xterra RP-18 5 μm, 30×100 mm. Eluting Solvent, MeCN/H$_2$O (NH$_4$HCO$_3$, 0.1 M, pH=10) (v. 90/10 to 10/90 over 20 min.) Flow rate, 75 mL/min., uv, 250 nm) (100 mg, yield, 53%). $^1$H NMR (300 MHz, CD$_3$OD) δ 1.45-1.65 (m, 1H), 1.65-1.94 (m, 2H), 1.93-2.16 (m, 1H), 2.19-2.39 (m, 1H), 2.67-3.11 (m, 5H), 3.37-3.54 (m, 1H), 5.18-5.35 (m, 1H), 6.91 (d, J=8.5 Hz, 1H), 7.19 (d, J=9.2 Hz, 1H), 7.70 (dd, J=8.5, 2.0 Hz, 1H), 7.95 (d, J=9.5 Hz, 1H), 8.03 (d, J=2.0 Hz, 1H) ppm. MS (DCl/NH$_3$): 375 (M+H)$^+$, 377 (M+H)$^+$.

Example 30B

4-{6-[(3R)-1-Aza-bicyclo[2.2.2]oct-3-yloxy]-pyridazin-3-yl}-2-bromo-phenylamine bis hydrogen chloride)

The product of Example 30A (20.0 mg, 0.05 mmol) was treated with HCl (Aldrich, 4 M in dioxane, 0.1 mL, 0.4 mmol) in EtOAc (2 mL) at ambient temperature for 1 hour to give the title compound as white solid (20 mg, yield, 91%). $^1$H NMR (300 MHz, CD$_3$OD) δ 1.87-2.26 (m, 3H), 2.27-2.51 (m, 1H), 2.58-2.70 (m, 1H), 3.33-3.61 (m, 5H), 3.95 (dd, J=14.2, 8.5 Hz, 1H), 5.27-5.61 (m, 1H), 6.97 (d, J=8.5 Hz, 1H), 7.54 (d, J=9.5 Hz, 1H), 7.74 (dd, J=8.5, 2.0 Hz, 1H), 8.10 (d, J=2.4 Hz, 1H), 8.27 (d, J=9.5 Hz, 1H) ppm. MS (DCl/NH$_3$): 375 (M+H)$^+$, 377 (M+H)$^+$. Anal. Calculated for C$_{17}$H$_{19}$BrN$_4$O.2.10HCl.0.60H$_2$O: C, 44.13; H, 4.86; N, 12.11. Found: C, 44.38; H, 4.83; N, 11.74.

Example 31

4-{6-[(3R)-1-Aza-bicyclo[2.2.2]oct-3-yloxy]-pyridazin-3-yl}-2,6-dibromo-phenylamine bis(hydrogen chloride)

Example 31A

4-{6-[(3R)-1-Aza-bicyclo[2.2.2]oct-3-yloxy]-pyridazin-3-yl}-2,6-dibromo-phenylamine The product of Example 29F (150 mg, 0.5 mmol) was treated with HOAc (36 µL, 36 mg, 0.6 mmol) in MeCN (5 mL) at ambient temperature for 5 min. N-bromosuccinimide (Aldrich, 100 mg, 0.55 mol) in MeCN (5 mL) was then added to the above solution at 0° C. and stirred at 0° C. for 1 h. It was then concentrated under reduced pressure. The title compound was purified by preparative HPLC (Xterra™, column, Xterra RP-18 5 µm, 30×100 mm. Eluting Solvent, MeCN/H$_2$O(NH$_4$HCO$_3$, 0.1 M, pH=10) (v. 90/10 to 10/90 over 20 min.) Flow rate, 75 mL/min., uv, 250 nm) (70 mg, yield, 31%). $^1$H NMR (300 MHz, CD$_3$OD) δ 1.46-1.65 (m, 1H), 1.65-1.94 (m, 2H), 1.96-2.12 (m, 1H), 2.22-2.37 (m, 1H), 2.70-3.07 (m, 5H), 3.38-3.65 (m, 1H), 5.13-5.41 (m, 1H), 7.21 (d, J=9.5 Hz, 1H), 7.97 (d, J=9.2 Hz, 1H), 8.08 (s, 1H) ppm. MS (DCl/NH$_3$): 453 (M+H)$^+$, 455 (M+H)$^+$, 457 (M+H)$^+$.

Example 31B

4-{6-[(3R)-1-Aza-bicyclo[2.2.2]oct-3-yloxy]-pyridazin-3-yl}-2,6-dibromo-phenylamine bis hydrogen chloride)

The product of Example 30A (70.0 mg, 0.15 mmol) was treated with HCl (Aldrich, 4 M in dioxane, 0.1 mL, 0.4 mmol) in EtOAc (2 mL) at ambient temperature for 1 hour to give the title compound as white solid (40 mg, yield, 51%). $^1$H NMR (300 MHz, CD$_3$OD) δ 1.91-2.25 (m, 5H), 2.26-2.50 (m, 1H), 2.60-2.81 (m, 1H), 3.32-3.61 (m, 5H), 3.96 (dd, J=14.2, 8.1 Hz, 1H), 5.44-5.62 (m, 1H), 7.71 (d, J=9.5 Hz, 1H), 8.12 (s, 2H), 8.41 (d, J=9.5 Hz, 1H) ppm. MS (DCl/NH$_3$): 453 (M+H)$^+$, 455 (M+H)$^+$, 457 (M+H)$^+$. Anal. Calculated for C$_{17}$H$_{18}$Br$_2$N$_4$O.2.00. HCl 1.00H$_2$O: C, 37.46; H, 4.07; N, 10.15. Found: C, 37.13; H, 3.88; N, 10.15.

Example 32

2-({4-[6-[(3R)-1-Aza-bicyclo[2.2.2]oct-3-yloxy]-pyridazin-3-yl}-phenyl}-hydrazono)-propionic acid ethyl ester trifluoroacetate

Example 32A

2-Bromo-1-(4-iodo-phenyl)-ethanone

To the solution of 1-(4-Iodo-phenyl)-ethanone (Aldrich, 125 g, 508 mmol) in glacial acetic acid (600 mL) was added the bromine (Aldrich, 79.3 g, 508 mmol, in 50 mL of acetic acid) and stirred at room temperature for 10 hours. It was concentrated under reduced pressure. The residue was then diluted with ethyl acetate (100 mL) and washed with brine (3×50 mL). The organic solution was concentrated. The title compound was obtained as yellow solid by recrystallization from diethyl ether (150 g, 91%). $^1$H NMR (300 MHz, CDCl$_3$) δ 4.39 (s, 2H), 7.69 (d, J=8.5 Hz, 2H), 7.87 (d, J=8.5 Hz, 2 H) ppm; MS (DCl/NH$_3$) m/z 246 (M–Br)$^+$, 264 (M–Br+NH$_4$)$^+$.

Example 32B

2-[2-(4-Iodo-phenyl)-2-oxo-ethyl]-malonic acid diethyl ester

Under N$_2$, diethyl malonate (Aldrich, 8.0 g, 50 mmol) was treated with sodium hydride (1.2 g, 50 mmol) in dry THF (120 mL) at 0° C. for 30 minute. The solution of the product of Example 32A (15.8 g, 48.6 mmol) in THF (30 mL) was then slowly added at 0° C. and the reaction mixture stirred additional 30 minutes at room temperature. It was quenched with water (10 mL) carefully and diluted with ethyl acetate (200 mL). The mixture was then washed with brine (3×20 mL). The organic solution was concentrated to give the title compound as oil (15 g, 74%). $^1$H NMR (300 MHz, CDCl$_3$) δ 1.25-1.32 (m, J=7.1, 7.1 Hz, 7 H), 3.57 (d, J=7.1 Hz, 2 H), 4.16-4.29 (m, 4 H), 7.69 (d, J=8.5 Hz, 2 H), 7.84 (d, J=8.8 Hz, 2 H) ppm; MS (DCl/NH$_3$) m/z 405 (M+H)$^+$, 422 (M+NH$_4$)$^+$.

Example 32C

2-[2-(4-Iodo-phenyl)-2-oxo-ethyl]-malonic acid

The product of Example 32B (1.0 g, 2.5 mmol) was treated with NaOH solution (1 N, 7.5 ml, 7.5 mmol) in ethanol (5 mL) at 60° C. for 1.5 hours, and then filtered through a Celite pad. The filtrate was concentrated under vacuum and the residue was diluted with water (20 mL), acidified with HCl (6 N) till pH=1. The solid started to precipitate and was collected by filtration, dried under vacuum to give the title compound as white solid (730 mg, 84%). $^1$H NMR (300 MHz, MeOH-D$_4$) δ 3.58 (d, J=7.1 Hz, 2 H), 3.93 (t, J=7.0 Hz, 1 H), 7.75 (d, J=8.5 Hz, 2 H), 7.91 (d, J=8.8 Hz, 2 H) ppm; MS (DCl/NH$_3$) m/z 366 (M+NH$_4$)$^+$.

Example 32D 6-(4-Iodo-phenyl)-4,5-dihydro-2H-pyridazin-3-one

The product of Example 32C (25 g, 71.8 mmol) was treated with hydrazine hydrate (55% aq., 16 mL, ~275 mmol) in ethanol (300 mL) at 78° C. for 60 hours according to the procedure of Example 29A. The title compound was obtained as white solid (20.5 g, 95.1%). ¹H NMR (300 MHz, CDCl₃) δ 2.62 (t, J=8.3 Hz, 2 H), 2.96 (t, J=8.3 Hz, 2 H), 7.45 (d, J=8.5 Hz, 2 H), 7.75 (d, J=8.8 Hz, 2 H), 8.51 (s, 1 H) ppm; MS (DCl/NH₃) m/z 301 (M+H)⁺ 318 (M+NH₄)⁺.

Example 32E 6-(4-Iodo-phenyl)-2H-pyridazin-3-one

The product of Example 32D (20.5 g, 68.3 mmol) was treated with bromine (Aldrich, 12.0 g, 75 mmol) in glacial acetic acid (250 mL) at 100° C. for 1 h. according to the procedure of Example 29B. The title compound was obtained as solid (20.0 g, 98%). ¹H NMR (300 MHz, MeOH-D₄) δ 7.06 (d, J=9.8 Hz, 1 H), 7.65 (d, J=8.8 Hz, 2 H), 7.84 (d, J=8.8 Hz, 2 H), 8.01 (d, J=9.8 Hz, 1 H) ppm; MS (DCl/NH₃) m/z 299 (M+H)⁺.

Example 32F

3-Chloro-6-(4-iodo-phenyl)-pyridazine

The product of Example 32E (20.0 g, 66.7 mmol) was treated with POCl₃ (Aldrich, 200 mL) at 100° for 16 hours according to the procedure of Example 29C. The title compound was obtained as solid (19.2 g, 91%). ¹H NMR (300 MHz, CDCl₃) δ 7.57 (d, J=8.8 Hz, 1 H), 7.76-7.83 (m, 3 H), 7.85-7.91 (m, 2 H) ppm. MS (DCl/NH₃) m/z 317 (M+H)⁺.

Example 32G (R)-3-[6-(4-Iodo-phenyl)-pyridazin-3-yloxy]-1-aza-bicyclo[2.2.2]octane The product of Example 6B (1.27 g, 10 mmol) was coupled with the product of Example 32F (3.16 g, 10 mmol) according to the procedure of Example 29D. The title compound was obtained as solid (3.05 g, 75%). ¹H NMR (300 MHz, MeOH-D₄) δ 1.49-1.63 (m, 1 H) 1.68-1.92 (m, 2 H) 1.98-2.13 (m, 1 H), 2.27-2.35 (m, 1 H), 2.79-3.01 (m, 5 H), 3.41-3.52 (m, 1 H), 5.27-5.35 (m, 1 H), 7.27 (d, J=9.2 Hz, 1 H), 7.75 (d, J=8.8 Hz, 2 H), 7.88 (d, J=8.8 Hz, 2 H), 8.05 (d, J=9.2 Hz, 1 H) ppm. MS (DCl/NH₃) m/z 408 (M+H)⁺.

Example 32H 2-({4-{6-[(3R)-1-Aza-bicyclo[2.2.2]oct-3-yloxy]-pyridazin-3-yl}-phenyl}-hydrazono)-propionic acid ethyl ester trifluoroacetate The product of Example 32G (407 mg, 1 mmol) was coupled with hydrazinecarboxylic acid tert-butyl ester (Aldrich, 158 mg, 1.2 mmol) under the catalysis of CuI (Strem Chemicals, 14.3 mg, 0.075 mmol) with Cs₂CO₃ (Strem Chemicals, 455 mg, 1.4 mmol) in dry DMF (Aldrich, 4 mL) at 80° C. for 16 hours. After the reaction went to completion, it was then colled down to ambient temperature and diluted with ethyl acetate (50 mL), washed with water (2×10 mL). The organic phase was concentrated under vacuum to give crude (R)-N-{4-[6-(1-aza-bicyclo[2.2.2]oct-3-yloxy)-pyridazin-3-yl]-phenyl}-hydrazinecarboxylic acid tert-butyl ester, which was then treated with 2-oxo-propionic acid ethyl ester (Aldrich, 232 mg, 2.0 mmol) under the catalysis of p-toluenesulfonic acid (38 mg, 0.2 mmol) in EtOH (5 mL) at 100° C. for 2 hours. The title compound was purified by preparative HPLC (Gilson, column, Symmetry® C-8 7 μm, 40×100 mm. Eluting Solvent, MeCN/H₂O (with 0.2% v. TFA) (v. 90/10 to 10/90 over 20 min.) Flow rate, 75 mL/min., uv, 250 nm) as solid (25.7 mg, 4.7%). ¹H NMR (300 MHz, MeOH-D₄) δ 1.36 (t, J=7.1 Hz, 3 H), 1.91-2.24 (m, 6 H), 2.32-2.47 (m, 1 H), 2.60-2.69 (m, J=4.1 Hz, 1 H), 3.32-3.55 (m, 5 H), 3.91-4.04 (m, 1 H), 4.30 (q, J=7.1 Hz, 2 H), 5.49-5.58 (m, 1 H), 7.33 (d, J=9.2 Hz, 1 H), 7.46 (d, J=8.8 Hz, 2 H), 7.91 (d, J=9.2 Hz, 2 H), 8.11 (d, J=9.5 Hz, 1 H) ppm. MS (DCl/NH₃) m/z 410 (M+H)⁺. Anal. Calculated for C₂₂H₂₇N₅O₃.1.25 CF₃CO₂H: C, 53.31; H, 5.16; N, 12.69. Found: C, 53.38; H, 5.03; N, 12.68.

Example 33

(R)-N-{4-[6-(1-Aza-bicyclo[2.2.2]oct-3-yloxy)-pyridazin-3-yl]-phenyl}-acetamide trifluoroacetate Example 33A (3R)-3-[(6-chloropyridazin-3-yl)oxy]quinuclidine The product of Example 6B (635 mg, 5 mmol) was coupled with 3,6-dichloropyridazine (Aldrich, 925 mg, 6.25 mmol) according to the procedure of Example 29D. The title compound was purified by chromatography (SiO₂, CH₂Cl₂:MeOH:NH₃.H₂O, 90:10:1, R_f, 0.20) as solid (750 mg, yield, 63%). ¹H NMR (300 MHz, CD₃OD) δ 1.54-1.68 (m, 1H), 1.71-1.95 (m, 2H), 2.00-2.14 (m, 1H), 2.28-2.36 (m, 1H), 2.83-3.08 (m, 5H), 3.44-3.56 (m, 1H), 5.23-5.30 (m, 1H), 7.24 (d, J=9.2 Hz, 1H), 7.66 (d, J=9.2 Hz, 1H) ppm. MS (DCl/NH₃): 240 (M+H)⁺, 242 (M+H)⁺.

Example 33B (R)-N-{4-[6-(1-Aza-bicyclo[2.2.2]oct-3-yloxy)-pyridazin-3-yl]-phenyl}-acetamide trifluoroacetate The product of Example 33A (182 mg, 0.76 mmol) was coupled with N-[4-(4,4,5,5-tetramethyl-[1,3,2]dioxaborolan-2-yl)-phenyl]-acetamide (TCI, 500 mg, 1.9 mmol) under the catalysis of dichlorobis(triphenylphosphine)palladium (II) (Aldrich, 53 mg, 0.076 mmol) and 2-(dicyclohexylphosphino)biphenyl (Strem Chemicals, 6.5 mg, 0.019 mmol) in 1 mL each of ethanol, p-dioxane, and 1 M aq. sodium carbonate at 150° C. at 330 watts for 10 min in an Emry™ Creator microwave. The mixture was cooled to room temperature, filtered through Celite®, and concentrated onto silica. The product was purified by column chromatography (SiO₂, 5% methanol containing 1% NH₄OH—CH₂Cl₂) to provide a free base of the title compound as solid (203 mg, 79%), which was dissolved in methanol (0.8 mL) containing trifluoroacetic acid (75 mg, 51 μL, 0.66 mmol). Diethyl ether (1 mL) was added to precipitate the title compound. ¹H NMR (300 MHz, MeOH-D₄) δ 1.89-2.04 (m, 1 H), 2.05-2.14 (m, 1 H), 2.14-2.18 (m, 1 H), 2.16 (s, 3 H), 2.32-2.46 (m, 1 H), 2.64 (td, J=6.5, 3.6 Hz, 1 H), 3.33-3.53 (m, 6 H), 3.97 (dd, J=13.9, 8.1 Hz, 1 H), 5.51-5.58 (m, 1 H), 7.32 (d, J=9.4 Hz, 1 H), 7.69-7.78 (m, 2 H), 7.91-7.98 (m, 2 H), 8.11 (d, J=9.3 Hz, 1 H) ppm; MS (DCl/NH₃): m/z 339 (M+H)⁺.

Example 34

4-{6-[(3R)-1-Aza-bicyclo[2.2.2]oct-3-yloxy]-pyridazin-3-yl}-2-nitro-phenylamine bis(hydrogen chloride)

Example 34A (4-Bromo-2-nitro-phenyl)-carbamic Acid tert-butyl ester

4-Bromo-2-nitro-phenylamine (Aldrich, 10.8 g, 50 mmol) was treated with di(tert-butyl) dicarbonate (Aldrich, 11.99 g, 55 mmol) in THF (Aldrich, 100 mL) at refluxing for 6 hours. It was then concentrated and the title compound was purified by recrystallization in EtOH as white solid (12.8 g, yield, 81%). $^1$H NMR (300 MHz, MeOH-D$_4$) δ 1.40 (S, 9 H), 7.21 (d, J=8.5 Hz, 1 H), 7.76 (dd, J=8.4, 2.3 Hz, 1 H), 8.21 (d, J=2.1 Hz, 1 H) ppm. MS (DCl/NH$_3$): 334 (M+H)$^+$, 336 (M+H)$^+$.

Example 34B

[2-Nitro-4-(4,4,5,5-tetramethyl-[1,3,2]dioxaborolan-2-yl)-phenyl]-carbamic Acid tert-butyl ester The product of Example 34A (10.05 g, 30 mmol) was coupled with bis(pinacolato)diboron (Aldrich, 9.14 g, 36 mmol) under the catalysis of PdCl$_2$(dppf)$_2$.CH$_2$Cl$_2$ (Aldrich, 490 mg, 0.6 mmol) with KOAc (Aldrich, 6.0 g, 60 mmol) in dioxane (anhydrous, Aldrich, 150 mL) at 80° C. for 10 hours according to the procedure of Example 26A. The title compound was purified by chromatography (SiO$_2$, hexane: EtOAc, 70:30, R$_f$ 0.5) as solid (9.0 g, yield, 83%). $^1$H NMR (300 MHz, CDCl$_3$) δ 1.37 (s, 9 H), 1.38 (s, 12 H), 7.99 (d, J=1.4 Hz, 1 H), 8.02 (d, J=1.4 Hz, 1 H), 8.45 (d, J=1.4 Hz, 1 H) ppm. MS (DCl/NH$_3$): 382 (M+NH$_4$)$^+$.

Example 34C

{4-{6-[(3R)-1-Aza-bicyclo[2.2.2]oct-3-yloxy]-pyridazin-3-yl}-2-nitro-phenyl}-carbamic acid tert-butyl ester The product of Example 33A (240 mg, 1 mmol) was coupled with the product of Example 34B (0.72, 2 mmol) under the catalysis of Pd$_2$(dba)$_3$ (24 mg, 0.025 mmol) and ($^t$Bu$_3$P)$_2$Pd (26 mg, 0.05 mmol) with CsF (Strem Chemicals, 228 mg, 1.5 mmol) in dioxane (8 mL) and DMF (Aldrich, 1 mL) at 80° C. under N$_2$ for 16 hours. After the reaction went to completion, it was cooled down to room temperature and diluted with EtOAc (50 mL), washed with brine (2×10 mL). The organic solution was and concentrated under reduced pressure and the title compound was purified by chromatography (SiO$_2$, EtOAc: MeOH (v. 2% NH$_3$.H$_2$O), 50:50, R$_f$ 0.3) as yellow solid (350 mg, 79%). $^1$H NMR (300 MHz, MeOH-D$_4$) δ 1.40 (s, 9 H), 1.51-1.70 (m, 1 H), 1.70-1.98 (m, 2 H), 2.00-2.23 (m, 1 H), 2.37-2.51 (m, 1 H), 2.71-3.18 (m, 5 H), 3.47-3.69 (m, 1 H), 5.33-5.49 (m, 1 H), 7.30 (d, J=9.2 Hz, 1 H), 7.54 (d, J=8.5 Hz, 1 H), 7.62 (s, 1 H), 8.14 (d, J=9.5 Hz, 1 H), 8.37 (dd, J=8.1, 2.0 Hz, 1 H), 8.80 (d, J=2.0 Hz, 1 H) ppm. MS (DCl/NH$_3$): 442 (M+H)$^+$.

Example 34D

4-{6-[(3R)-1-Aza-bicyclo[2.2.2]oct-3-yloxy]-pyridazin-3-yl}-2-nitro-phenylamine

The product of Example 34C (350 mg, 0.79 mmol) was treated with HCl (Aldrich, 4 M in dioxane, 2 mL, 8 mmol) in EtOH (5 mL) at ambient temperature for 1 h. The mixture was concentrated and the title compound was purified by chromatography (SiO$_2$, EtOAc: MeOH (v. 2% NH$_3$.H$_2$O), 50:50, R$_f$ 0.1) as white solid (250 mg, 93%). $^1$H NMR (300 MHz, MeOH-D$_4$) δ 1.54-1.66 (m, 1 H), 1.72-2.02 (m, 2 H), 2.07-2.24 (m, 1 H), 2.35-2.57 (m, 1 H), 2.79-3.18 (m, 5 H), 3.48-3.69 (m, 1 H), 5.27-5.47 (m, 1 H), 7.10 (d, J=8.8 Hz, 1 H), 7.22 (d, J=9.5 Hz, 1 H), 7.66 (s, 1 H), 7.98 (d, J=9.2 Hz, 1 H), 8.08 (dd, J=9.0, 2.2 Hz, 1 H), 8.68 (d, J=2.4 Hz, 1 H) ppm. MS (DCl/NH$_3$): 342 (M+H)$^+$.

Example 34E

4-{6-[(3R)-1-Aza-bicyclo[2.2.2]oct-3-yloxy]-pyridazin-3-yl}-2-nitro-phenylamine bis(hydrogen chloride)

The product of Example 34D (50 mg, 0.15 mmol) was treated with HCl (Aldrich, 4 M in dioxane, 0.5 mL, 2 mmol) in EtOAc (5 mL) at ambient temperature for 1 h to provide the title compound as yellow solid (50 mg, 83%). $^1$H NMR (300 MHz, MeOH-D$_4$) δ 1.88-2.29 (m, 3 H), 2.30-2.50 (m, 1 H), 2.56-2.74 (m, 1 H), 3.34-3.62 (m, 5 H), 3.97 (dd, J=14.4, 8.3 Hz, 1 H), 5.53 (dd, J=7.8, 3.4 Hz, 1 H), 7.20 (d, J=8.8 Hz, 1 H), 7.72 (d, J=9.5 Hz, 1 H), 7.78 (s, 1 H) 8.01 (dd, J=9.2, 2.4 Hz, 1 H), 8.44 (d, J=9.5 Hz, 1 H), 8.80 (d, J=2.0 Hz, 1 H) ppm. MS (DCl/NH$_3$): 342 (M+H)$^+$. Anal. Calculated for C$_{17}$H$_{19}$N$_5$O$_3$.2.00HCl2.00H$_2$O.0.10 EtOAc: C, 45.62; H, 5.46; N, 15.29. Found: C, 45.90; H, 5.25; N, 14.94.

Example 35

4-{6-[(3R)-1-Aza-bicyclo[2.2.2]oct-3-yloxy]-pyridazin-3-yl}-benzene-1,2-diamine tri(hydrogen chloride)

Example 35A

4-{6-[(3R)-1-Aza-bicyclo[2.2.2]oct-3-yloxy]-pyridazin-3-yl}-benzene-1,2-diamine

The product of Example 34D (200 mg, 0.59 mmol) was hydrogenated under the catalysis of Pd/C (Aldrich, 10 wt. %, 50 mg) in EtOH (10 mL) under hydrogen at ambient temperature for 10 h. After the reaction went to completion, the catalyst was removed through a short column of diatomaceous earth (~2 g) and the filtrate was washed with EtOH (2×5 mL). The ethanol solution was concentrated to give the title compound (180 mg, yield, 98%). $^1$H NMR (500 MHz, CD$_3$-OD) δ 1.58-1.73 (m, 1 H), 1.76-2.00 (m, 2 H), 2.06-2.27 (m, 1 H), 2.29-2.47 (m, 1 H), 2.81-3.20 (m, 5 H), 3.52-3.68 (m, 1 H), 5.11-5.57 (m, 1 H), 6.78 (d, J=8.2 Hz, 1 H), 7.12-7.26 (m, 2H), 7.32 (d, J=2.1 Hz, 1 H), 7.92 (d, J=9.2 Hz, 1 H) ppm. MS (DCl/NH$_3$): 312 (M+H)$^+$.

Example 35B

4-{6-[(3R)-1-Aza-bicyclo[2.2.2]oct-3-yloxy]-pyridazin-3-yl}-benzene-1,2-diamine tri(hydrogen chloride)

The product of Example 35A (50 mg, 0.16 mmol) was treated with HCl (Aldrich, 4 M in dioxane, 0.5 mL, 2 mmol) in EtOAc (5 mL) at ambient temperature for 1 h to provide the title compound as yellow solid (32 mg, 48%). $^1$H NMR (300 MHz, MeOH-D$_4$) δ 1.87-2.27 (m, 3 H), 2.31-2.44 (m, 1 H), 2.64-2.74 (m, 1 H), 3.34-3.56 (m, 3 H), 3.55-3.70 (m, 2 H), 3.85-4.06 (m, 1 H), 5.32-5.67 (m, 1 H), 7.17 (d, J=8.3 Hz, 1 H), 7.84 (d, J=8.6 Hz, 1 H), 7.94 (s, 1 H), 8.00 (d, J=8.9 Hz, 1 H), 8.62 (d, J=8.9 Hz, 1H) ppm. MS (DCl/NH$_3$): 312 (M+H)$^+$. Anal. Calculated for C$_{17}$H$_{21}$N$_5$O.3.38HCl.1.70H$_2$O.0.25 EtOAc: C, 44.37; H, 6.16; N, 14.37. Found: C, 44.05; H, 5.78; N, 13.99.

Example 36

4-{2-[(3R)-1-Aza-bicyclo[2.2.2]oct-3-yloxy]-pyrimidin-5-yl}-2-nitro-phenylamine bis(hydrogen chloride)

Example 36A

{4-{2-[(3R)-1-Aza-bicyclo[2.2.2]oct-3-yloxy]-pyrimidin-5-yl}-2-nitro-phenyl}-carbamic acid tert-butyl ester The product of Example 19A (0.57 g, 2.0 mmol) was coupled with the product of Example 34B (1.50 g, 4 mmol) under the catalysis of Pd$_2$(dba)$_3$ (24 mg, 0.025 mmol) and ($^t$Bu$_3$P)$_2$Pd (26 mg, 0.05 mmol) with CsF (Strem Chemicals, 1.80 g, 12.0 mmol) in dioxane (20 mL) and DMF (Aldrich, 2 mL) at 80° C. under N$_2$ for 16 hours according to the procedure of Example 34C. The title compound was purified by chromatography (SiO$_2$, EtOAc: MeOH (v. 2% NH$_3$.H$_2$O), 50:50, R$_f$, 0.3) as oil (590 mg, 67%). $^1$H NMR (300 MHz, MeOH-D$_4$) δ 1.38 (s, 9 H), 1.46-1.59 (m, 1 H), 1.61-1.73 (m, 1 H), 1.74-1.88 (m, 1 H), 1.95-2.10 (m, 1 H), 2.22-2.33 (m, 1 H), 3.38-3.48 (m, 1 H), 5.15-5.25 (m, 1 H), 7.58 (d, J=8.2 Hz, 1 H), 7.97 (dd, J=8.8, 2.1 Hz, 1 H), 8.56 (d, J=4.9 Hz, 1 H), 8.97 (s, 2 H) ppm. MS (DCl/NH$_3$): 442 (M+H)$^+$.

Example 36B

4-{2-[(3R)-1-Aza-bicyclo[2.2.2]oct-3-yloxy]-pyrimidin-5-yl}-2-nitro-phenylamine

The product of Example 36A (100 mg, 0.23 mmol) was treated with HCl (Aldrich, 4 M in dioxane, 2 mL, 8 mmol) in EtOH (5 mL) at ambient temperature for 1 h. The mixture was concentrated and the title compound was purified by chromatography (SiO$_2$, EtOAc:MeOH (v. 2% NH$_3$.H$_2$O), 50:50, R$_f$, 0.1) as white solid (50 mg, 64%). $^1$H NMR (500 MHz, MeOH-D$_4$) δ 1.47-1.64 (m, 1 H), 1.65-1.78 (m, 1 H), 1.78-1.91 (m, 1 H), 1.96-2.16 (m, 1 H), 2.15-2.38 (m, 1 H), 2.73-3.05 (m, 5 H), 3.35-3.47 (m, 1 H), 4.96-5.28 (m, 1 H), 7.10 (d, J=8.8 Hz, 1 H), 7.68 (dd, J=8.8, 2.1 Hz, 1 H), 8.32 (d, J=2.1 Hz, 1 H), 8.79 (s, 2 H) ppm. MS (DCl/NH$_3$): 342 (M+H)$^+$.

Example 36C

4-{2-[(3R)-1-Aza-bicyclo[2.2.2]oct-3-yloxy]-pyrimidin-5-yl}-2-nitro-phenylamine bis(hydrogen chloride)

The product of Example 36B (50 mg, 0.15 mmol) was treated with HCl (Aldrich, 4 M in dioxane, 0.25 mL, 1 mmol) in EtOAc (5 mL) at ambient temperature for 1 hour to give the title compound as yellow solid. $^1$H NMR (400 MHz, MeOH-D$_4$) δ 1.89-2.25 (m, 3 H), 2.31-2.50 (m, 1 H), 2.55-2.72 (m, 1 H), 3.33-3.53 (m, 5 H), 3.81-3.98 (m, 1 H), 5.28-5.56 (m, 1 H), 7.12 (d, J=8.9 Hz, 1 H), 7.69 (dd, J=8.9, 2.1 Hz, 1 H), 8.34 (d, J=2.1 Hz, 1 H), 8.86 (s, 2 H) ppm. MS (DCl/NH$_3$): 342 (M+H)$^+$. Anal. Calculated for C$_{17}$H$_{19}$N$_5$O$_3$.3.00HCl.0.10H$_2$O.0.06 EtOAc: C, 48.91; H, 5.64; N, 16.54. Found: C, 48.70; H, 5.35; N, 16.17.

Example 37

2-Amino-4-{2-[(3R)-1-aza-bicyclo[2.2.2]oct-3-yloxy]-pyrimidin-5-yl}-phenol bis(hydrogen chloride)

Example 37A

1-Benzyloxy-4-bromo-2-nitro-benzene

4-Bromo-2-nitro-phenol (Aldrich, 2.18 g, 10 mmol) was treated with K$_2$CO$_3$ (Aldrich, 2.76 g, 20 mmol) in DMF (Aldrich, 100 mL) at ambient temperature for 20 min. Benzyl chloride (Aldrich, 1.52 g, 12 mmol) was added. The mixture was stirred at 100° C. for 6 h. It was then poured into ice/water (200 mL) and stirred at ambient temperature for 10 hours. The white solid was filtered and dried to give the title compound (3.0 g, yield, 100%). $^1$H NMR (300 MHz, CDCl$_3$) δ 5.23 (s, 2 H), 7.01 (d, J=9.2 Hz, 1 H), 7.31-7.49 (m, 5 H), 7.58 (dd, J=9.0, 2.5 Hz, 1 H), 7.98 (d, J=2.7 Hz, 1 H) ppm. MS (DCl/NH$_3$): 325 (M+H)$^+$, 327 (M+H)$^+$.

Example 37B

[2-Nitro-4-(4,4,5,5-tetramethyl-[1,3,2]dioxaborolan-2-yl)-phenyl]-carbamic acid tert-butyl ester The product of Example 37A (3.0 g, 10 mmol) was coupled with bis(pinacolato)diboron (Aldrich, 3.04 g, 12 mmol) according to the procedure of Example 28B. The title compound was purified by chromatography (SiO$_2$, hexane: EtOAc, 70:30, R$_f$, 0.5) as a solid (3.05 g, yield, 86%). $^1$H NMR (300 MHz, MEOH-D$_4$) δ 1.34 (s, 12H), 5.30 (s, 2 H), 7.27-7.43 (m, 4 H), 7.42-7.51 (m, 2 H), 7.89 (dd, J=8.3, 1.5 Hz, 1H), 8.09 (d, J=1.7 Hz, 1 H) ppm. MS (DCl/NH$_3$): 373 (M+NH$_4$)$^+$.

Example 37C (3R)-3-[5-(4-Benzyloxy-3-nitro-phenyl)-pyrimidin-2-yloxy]-1-aza-bicyclo[2.2.2]octane The product of Example 19A (1.42 g, 5 mmol) was coupled with the product of Example 37B (2.50 g, 7.0 mmol) according to the procedure of Example 20B. The title compound was purified by chromatography (SiO$_2$, EtOAc: MeOH (v. 2% NH$_3$.H$_2$O), 50:50, R$_f$, 0.3) as solid (1.75 g, 81%). $^1$H NMR (300 MHz, MeOH-D$_4$) δ 1.46-1.61 (m, 1 H), 1.63-1.92 (m, 2 H), 1.97-2.15 (m, 1 H), 2.17-2.33 (m, 1 H), 2.69-3.04 (m, 5 H), 3.35-3.49 (m, 1 H), 5.11-5.22 (m, 1 H), 5.34 (s, 2 H), 7.25-7.55 (m, 5 H), 7.85 (dd, J=8.8, 2.4 Hz, 1 H), 8.13 (d, J=2.0 Hz, 1 H), 8.63 (s, 1 H), 8.82 (s, 2 H) ppm. MS (DCI/NH$_3$): 433 (M+H)$^+$.

Example 37D

2-Amino-4-{2-[(3R)-1-aza-bicyclo[2.2.2]oct-3-yloxy]-pyrimidin-5-yl}-phenol

The product of Example 37C (380 mg, 0.88) was hydrogenated under the catalysis of Pd/C (Aldrich, 10 wt. %, 100 mg) according to the procedure of Example 28E. The title compound was obtained as yellow solid (220 mg, yield, 92%). $^1$H NMR (300 MHz, CD$_3$OD) δ 1.47-1.93 (m, 3 H), 1.95-2.35 (m, 2 H) 2.70-3.05 (m, 5 H), 3.33-3.48 (m, 1 H), 5.04-5.30 (m, J=8.8 Hz, 1 H), 6.72-6.88 (m, 2 H), 6.98 (d, J=1.7 Hz, 1 H), 8.70 (s, 2 H) ppm. MS (DCl/NH$_3$): 313 (M+H)$^+$.

Example 37E

2-Amino-4-{2-[(3R)-1-aza-bicyclo[2.2.2]oct-3-yloxy]-pyrimidin-5-yl}-phenol bis(hydrogen chloride)

The product of Example 37D (50 mg, 0.15 mmol) was treated with HCl (Aldrich, 4 M in dioxane, 0.25 mL, 1 mmol) in EtOAc (5 mL) at ambient temperature for 1 hour to give the title compound as yellow solid. $^1$H NMR (400 MHz, MeOH-D$_4$) δ 1.85-2.32 (m, 3 H), 2.30-2.56 (m, 1 H), 2.56-2.77 (m, 1H), 3.24-3.52 (m, 5 H), 3.79-4.00 (m, 1 H), 5.02-5.72 (m, J=4.1 Hz, 1 H), 5.42 (d, J=4.1 Hz, 1 H), 7.15 (d, J=8.5 Hz, 1H), 7.42-7.77 (m, 3 H), 8.77 (s, 2H) ppm. MS (DCl/NH$_3$): 313 (M+H)$^+$. Anal. Calculated for C$_{17}$H$_{20}$N$_4$O$_2$.2.00 HCl.1.80 H$_2$O.0.10 EtOAc: C, 49.00; H, 6.24; N, 13.14. Found: C, 49.17; H, 5.95; N, 12.83.

Example 38

Determination of Biological Activity

To determine the effectiveness of representative compounds of this invention as α7 nAChRs, the compounds of the invention were evaluated according to the [3H]-methyllycaconitine (MLA) binding assay and considering the [3H]-cytisine binding assay, which were performed as described below.

[3H]-Cytisine Binding

Binding conditions were modified from the procedures described in Pabreza L A, Dhawan, S, Kellar K J, [$^3$H]-Cytisine Binding to Nicotinic Cholinergic Receptors in Brain, Mol. Pharm. 39: 9-12, 1991. Membrane enriched fractions from rat brain minus cerebellum (ABS Inc., Wilmington, Del.) were slowly thawed at 4° C., washed and resuspended in 30 volumes of BSS-Tris buffer (120 mM NaCl/5 mM KCl/2 mM CaCl$_2$/2 mM MgCl$_2$/50 mM Tris-Cl, pH 7.4, 4° C.). Samples containing 100-200 µg of protein and 0.75 nM [3H]-cytisine (30 C$_i$/mmol; Perkin Elmer/NEN Life Science Products, Boston, Mass.) were incubated in a final volume of 500 µL for 75 minutes at 4° C. Seven log-dilution concentrations of each compound were tested in duplicate. Non-specific binding was determined in the presence of 10 µM (−)-nicotine. Bound radioactivity was isolated by vacuum filtration onto prewetted glass fiber filter plates (Millipore, Bedford, Mass.) using a 96-well filtration apparatus (Packard Instruments, Meriden, Conn.) and were then rapidly rinsed with 2 mL of ice-cold BSS buffer (120 mM NaCl/5 mM KCl/2 mM CaCl$_2$/2 mM MgCl$_2$). Packard MicroScint-20® scintillation cocktail (40 µL) was added to each well and radioactivity determined using a Packard TopCount® instrument. The IC$_{50}$ values were determined by nonlinear regression in Microsoft Excel® software. K$_i$ values were calculated from the IC$_{50}$s using the Cheng-Prusoff equation, where K$_i$=IC$_{50}$/1+[Ligand]/K$_D$].

[3H]-Methyllycaconitine (MLA) Binding

Binding conditions were similar to those for [3H]-cytisine binding. Membrane enriched fractions from rat brain minus cerebellum (ABS Inc., Wilmington, Del.) were slowly thawed at 4° C., washed and resuspended in 30 volumes of BSS-Tris buffer (120 mM NaCl, 5 mM KCl, 2 mM CaCl$_2$, 2 mM MgCl$_2$, and 50 mM Tris-Cl, pH 7.4, 22° C.). Samples containing 100-200 µg of protein, 5 nM [3H]-MLA (25 C$_i$/mmol; Perkin Elmer/NEN Life Science Products, Boston, Mass.) and 0.1% bovine serum albumin (BSA, Millipore, Bedford, Mass.) were incubated in a final volume of 500 µL for 60 minutes at 22° C. Seven log-dilution concentrations of each compound were tested in duplicate. Non-specific binding was determined in the presence of 10 µM MLA. Bound radioactivity was isolated by vacuum filtration onto glass fiber filter plates prewetted with 2% BSA using a 96-well filtration apparatus (Packard Instruments, Meriden, Conn.) and were then rapidly rinsed with 2 mL of ice-cold BSS. Packard MicroScint-20® scintillation cocktail (40 µL) was added to each well and radioactivity was determined using a Packard TopCount® instrument. The IC$_{50}$ values were determined by nonlinear regression in Microsoft Excel® software. K$_i$ values were calculated from the IC$_{50}$s using the Cheng-Prusoff equation, where K$_i$=IC$_{50}$/1+[Ligand]/K$_D$].

Compounds of the invention had K$_i$ values of from about 1 nanomolar to about 10 micromolar when tested by the MLA assay, many having a K$_i$ of less than 1 micromolar. [3H]-Cytisine binding values of compounds of the invention ranged from about 50 nanomolar to at least 100 micromolar. The determination of preferred compounds typically considered the K$_i$ value as measured by MLA assay in view of the K$_i$ value as measured by [3H]-cytisine binding, such that in the formula D=K$_{i\ 3H\text{-}cytisine}$/K$_{i\ MLA}$, D is about 50. Preferred compounds typically exhibited greater potency at α7 receptors compared to α4β2 receptors.

Compounds of the invention are α7 nAChRs ligands that modulate function of α7 nAChRs by altering the activity of the receptor. The compounds can be inverse agonists that inhibit the basal activity of the receptor or antagonists that completely block the action of receptor-activating agonists. The compounds also can be partial agonists that partially block or partially activate the α7 nAChR receptor or agonists that activate the receptor.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of the formula (I):

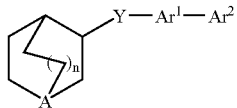

or a pharmaceutically acceptable salt, thereof, wherein:

A is N or N$^+$—O$^-$ n is 0, 1, or 2;

Y is selected from the group consisting of O, S, and —N(R$^1$)—;

Ar$^1$ is a group of the formula:

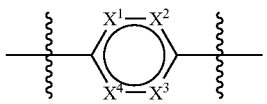

Ar$^2$ is a group of the formula:

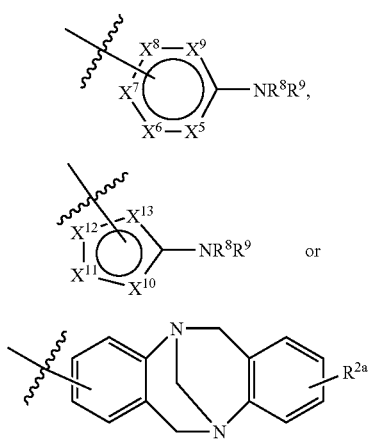

X$^1$, X$^2$, x$^3$, and X$^4$ are each independently selected from the group consisting of N and —C(R$^2$);

one of X$^5$, X$^6$, X$^7$, X$^8$ and X$^9$ is —C and the others are each independently selected from the group consisting of N and —C(R$^5$), and group (b) is attached to Ar$_1$ through one of X$^5$, X$^6$, X$^7$, X$^8$ and X$^9$ that is represented by C;

one of H$^{10}$, X$^{11}$, X$^{12}$, and X$^{13}$ is C and the others are each independently selected from the group consisting of N, —N(R$^1$), O, S and —C(R$^5$) and group (c) is attached to Ar$_1$ through one of X$^{10}$, X$^{11}$, X$^{12}$, and X$^{13}$ that is represented by C;

R$^1$ is hydrogen or alkyl;

R$^2$ at each occurrence is independently selected from the group consisting of hydrogen, halogen, alkyl, —OR$^3$, and —NHR$^4$;

R$^{2a}$ is halogen or alkyl;

R$^3$ and R$^4$ are each independently selected from the group consisting of hydrogen, alkyl, alkylcarbonyl, and arylcarbonyl;

R$^5$ is selected from the group consisting of hydrogen, halogen, nitro, alkyl, aryl, alkylcarbonyl, arylcarbonyl, —OR$^6$ and —NR$^8$R$^9$;

R$^6$ is independently selected from the group consisting of hydrogen, alkyl, alkylcarbonyl, and arylcarbonyl; and R$^8$ and R$^9$ are each independently selected from the group consisting of hydrogen, alkyl, aryl, arylalkyl, cycloalkylalkyl, alkylcarbonyl, —N=C(alkyl)(alkoxycarbonyl), alkoxycarbonyl, arylcarbonyl, aryloxycarbonyl, and alkylsulfonyl.

2. The compound of claim 1, wherein Ar$^1$ is selected from the group consisting of:

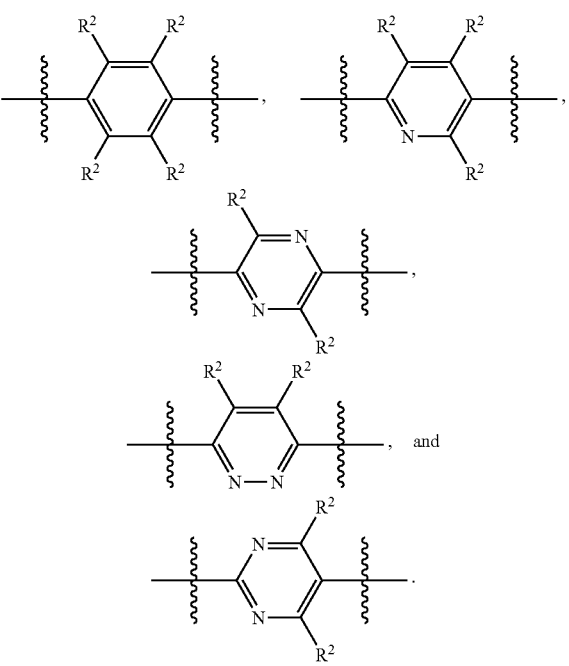

wherein R$^2$ t is as defined in claim 1.

3. The compound of claim 1, wherein Ar$^2$ is selected from the group consisting of:

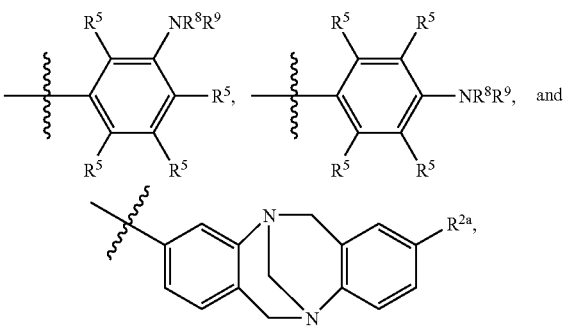

wherein:

R$^{2a}$ is halogen or alkyl;

R$^5$ is selected from the group consisting of hydrogen, halogens nitro, alkyl, aryl, alkylcarbonyl, arylcarbonyl, —OR$^6$ and —NR$^8$R$^9$;

R$^6$ is selected from the group consisting of hydrogen, alkyl, alkylcarbonyl, and arylcarbonyl;

R⁸ and R⁹ are each independently selected from the group consisting of hydrogen, alkyl, benzyl, methanesulfonyl, phenyl, 4-methylphenyl, benzyloxycarbonyl, acetyl, cyclohexylmethyl, tert-butyloxycarbonyl and —N═C(methyl)(ethoxycarbonyl).

4. The compound of claim 3, wherein R⁸ is hydrogen or alkyl; and R⁹ is selected from the group consisting of hydrogen, alkyl, benzyl, methanesulfonyl, phenyl, 4-methylphenyl, benzyloxycarbonyl, acetyl, cyclohexylmethyl, tert-butyloxycarbonyl and —N═C(methyl)(ethoxycarbonyl).

5. The compound of claim 1, or a pharmaceutically acceptable salt, thereof, selected from the group consisting of:

4'-(1-azabicyclo[2.2.2]oct-3-yloxy)-1,1'-biphenyl-3-amine;
4'-[(3R)-1-azabicyclo[2.2.2]oct-3-yloxy]-1,1'-biphenyl-3-amine;
4'-(1-azabicyclo[2.2.2]oct-3-yloxy)-4-methyl-1,1'-biphenyl-3-amine;
4'-[(3R)-1-azabicyclo[2.2.2]oct-3-yloxy]-4-methyl-1,1'-biphenyl-3-amine;
4'-(1-azabicyclo[2.2.2]oct-3-yloxy)-1,1'-biphenyl-4-amine;
4'-[(3R)-1-azabicyclo[2.2.2]oct-3-yloxy]-1,1'-biphenyl-4-amine;
4'-[(3S)-1-azabicyclo[2.2.2]oct-3-yloxy]-1,1'-biphenyl-4-amine;
N-[4'-(1-azabicyclo[2.2.2]oct-3-yloxy)-1,1'-biphenyl-4-yl]-N-methylamine;
N-{4'-[(3R)-1-azabicyclo[2.2.2]oct-3-yloxy]-1,1'-biphenyl-4-yl}-N,N-dimethylamine;
N-[4'-(1-azabicyclo[2.2.2]oct-3-yloxy)-1,1'-biphenyl-4-yl]methanesulfonamide;
N-[4'-(1-azabicyclo[2.2.2]oct-3-yloxy)-1,1'-biphenyl-4-yl]-N-phenylamine;
3-[6-(1-azabicyclo[2.2.2]oct-3-yloxy)pyridin-3-yl]aniline;
4-[5-(1-azabicyclo[2.2.2]oct-3-yloxy)pyrazin-2-yl]aniline;
4-{5-[(3R)-1-azabicyclo[2.2.2]oct-3-yloxy]pyrazin-2-yl}aniline;
4-{5-[(3S)-1-azabicyclo[2.2.2]oct-3-yloxy]pyrazin-2-yl}aniline;
N-{4-[5-(1-azabicyclo[2.2.2]oct-3-yloxy)pyrazin-2-yl]phenyl}-N,N-dimethylamine;
N-{4-[5-(1-azabicyclo[2.2.2]oct-3-yloxy)pyrazin-2-yl]phenyl}acetamide;
4-[2-(1-azabicyclo[2.2.2]oct-3-yloxy)pyrimidin-5-yl]aniline;
4-{2-[(3R)-1-azabicyclo[2.2.2]oct-3-yloxy]pyrimidin-5-yl}aniline;
3-[2-(1-azabicyclo[2.2.2]oct-3-yloxy)pyrimidin-5-yl]aniline;
3-{2-[(3R)-1-azabicyclo[2.2.2]oct-3-yloxy]pyrimidin-5-yl}aniline;
3-{2-[(3S)-1-azabicyclo[2.2.2]oct-3-yloxy]pyrimidin-5-yl}aniline;
5-[2-(1-azabicyclo[2.2.2]oct-3-yloxy)pyrimidin-5-yl]-2-methylaniline;
N-1-azabicyclo[2.2.2]oct-3-yl-1,1'-biphenyl-4,4'-diamine;
4'-(1-oxy-1-aza-bicyclo[2.2.2]oct-3-yloxy)-biphenyl-3-ylamine;
[4'-(1-aza-bicyclo[2.2.2]oct-3-yloxy)-biphenyl-4-yl]-p-tolyl-amine;
[4'-(1-aza-bicyclo[2.2.2]oct-3-yloxy)-biphenyl-4-yl]-cyclohexylmethyl-amine;
2-[4-(1-aza-bicyclo[2.2.2]oct-3-yloxy)-phenyl]-8-iodo-6H,12H-5,11-methano-dibenzo[b,f][1,5]diazocine;
4-{6-[(3R)-1-aza-bicyclo[2.2.2]oct-3-yloxy]-pyridazin-3-yl}-phenylamine;
4-{6-[(3R)-1-aza-bicyclo[2.2.2]oct-3-yloxy]-pyridazin-3-yl}-2-bromo-phenylamine;
4-{6-[(3R)-1-aza-bicyclo[2.2.2]oct-3-yloxy]-pyridazin-3-yl}-2,6-dibromo-phenylamine;
2-({4-{6-[(3R)-1-aza-bicyclo[2.2.2]oct-3-yloxy]-pyridazin-3-yl}-phenyl}-hydrazono)-propionic acid ethyl ester;
(R)-N-{4-[6-(1-aza-bicyclo[2.2.2]oct-3-yloxy)-pyridazin-3-yl]-phenyl}-acetamide;
4-{6-[(3R)-1-aza-bicyclo[2.2.2]oct-3-yloxy]-pyridazin-3-yl}-2-nitro-phenylamine;
4-{6-[(3R)-1-aza-bicyclo[2.2.2]oct-3-yloxy]-pyridazin-3-yl}-benzene-1,2-diamine;
4-{2-[(3R)-1-aza-bicyclo[2.2.2]oct-3-yloxy]-pyrimidin-5-yl}-2-nitro-phenylamine; and
2-amino-4-{2-[(3R)-1-aza-bicyclo[2.2.2]oct-3-yloxy]-pyrimidin-5-yl}-phenol.

6. A pharmaceutical composition comprising a therapeutically effective amount of a compound of claim 1 in combination with a pharmaceutically acceptable carrier.

* * * * *

UNITED STATES PATENT AND TRADEMARK OFFICE
CERTIFICATE OF CORRECTION

| | |
|---|---|
| PATENT NO. | : 7,309,699 B2 |
| APPLICATION NO. | : 11/015158 |
| DATED | : December 18, 2007 |
| INVENTOR(S) | : Jianguo Ji, Tao Li and Ying Wang |

Page 1 of 1

It is certified that error appears in the above-identified patent and that said Letters Patent is hereby corrected as shown below:

Column 70, claim 2
Line 42, "$R_2$ t is as" should read -- $R_2$ is as --

Column 70, claim 3
Line 63, "halogens nitro," should read -- halogen, nitro, --

Signed and Sealed this

Fourteenth Day of April, 2009

JOHN DOLL
*Acting Director of the United States Patent and Trademark Office*